US012686693B2

(12) United States Patent
Yamamoto et al.

(10) Patent No.: US 12,686,693 B2
(45) Date of Patent: Jul. 21, 2026

(54) SILANE-CONTAINING CONDENSED CYCLIC DIPEPTIDE COMPOUND, PRODUCTION METHOD THEREFOR, AND METHOD FOR PRODUCING POLYPEPTIDE COMPOUND USING SAME

(71) Applicant: CHUBU UNIVERSITY EDUCATIONAL FOUNDATION, Aichi (JP)

(72) Inventors: Hisashi Yamamoto, Aichi (JP); Tomohiro Hattori, Aichi (JP)

(73) Assignee: CHUBU UNIVERSITY EDUCATIONAL FOUNDATION, Aichi (JP)

(*) Notice: Subject to any disclaimer, the term of this patent is extended or adjusted under 35 U.S.C. 154(b) by 503 days.

(21) Appl. No.: 18/549,391

(22) PCT Filed: Dec. 6, 2021

(86) PCT No.: PCT/JP2021/044773
§ 371 (c)(1),
(2) Date: Sep. 7, 2023

(87) PCT Pub. No.: WO2022/190486
PCT Pub. Date: Sep. 15, 2022

(65) Prior Publication Data

US 2024/0182517 A1 Jun. 6, 2024

(30) Foreign Application Priority Data

Mar. 9, 2021 (JP) ................................ 2021-037691

(51) Int. Cl.
*C07F 7/18* (2006.01)
*C07K 1/02* (2006.01)

(52) U.S. Cl.
CPC ........... *C07F 7/1896* (2013.01); *C07K 1/026* (2013.01)

(58) Field of Classification Search
None
See application file for complete search history.

(56) References Cited

U.S. PATENT DOCUMENTS

| | | | |
|---|---|---|---|
| 11,370,747 | B2 | 6/2022 | Yamamoto et al. |
| 11,512,108 | B2 | 11/2022 | Yamamoto et al. |
| 2020/0291061 | A1 | 9/2020 | Nagaya et al. |
| 2021/0070690 | A1 | 3/2021 | Yamamoto et al. |
| 2022/0112233 | A1 | 4/2022 | Yamamoto et al. |
| 2022/0306682 | A1 | 9/2022 | Nagaya et al. |

FOREIGN PATENT DOCUMENTS

| | | | |
|---|---|---|---|
| WO | 2010103857 | A | 9/2010 |
| WO | 2017204144 | A | 11/2017 |
| WO | 2018199147 | A | 11/2018 |
| WO | 2019069978 | A | 4/2019 |
| WO | 2019208731 | A | 10/2019 |
| WO | 2018199146 | A | 2/2020 |
| WO | 2020262258 | A | 12/2020 |
| WO | 2021039901 | A | 3/2021 |

OTHER PUBLICATIONS

El-Faham et al., "Peptide Coupling Reagents, More than a Letter Soup", American Chemical Society, Chemical Reviews, 2011, pp. 6557-6602.
Dunetz et al., "Large-Scale Applications of Amide Coupling Reagents for the Synthesis of Pharmaceuticals", American Chemical Society, Organic Process Research & Development, 2016, pp. 140-177.
Figueiredo et al., "Nonclassical Routes for Amide Bond Formation", American Chemical Society, Chemical Reviews, 2016, pp. 12029-12122.
Schnolzer et al., Constructing Proteins by Dovetailing Unprotected Synthetic Peptides: Backbone-Engineered HIV Protease, Science, vol. 256, 1992, pp. 221-225.
Bode et al., "Chemoselective Amide Ligations by Decarboxylative Condesations of N-Alkylhydroxylamines and a-Ketoacids", Angew. Chem. Int., 2006, 45, pp. 1248-1252.
Fuse et al., "Peptide-Chain Elongation Using Unprotected Amino Acids in a Micro-Flow Reactor", Chemistry European Journal, 2019, pp. 15091-15097.
Kurasaki et al., "Isostearyl Mixed Anhydrides for the Preparation of N-Methylated Peptides Using C-Terminally Unprotected N-Methylamino Acids", American Chemical Society, Organic Letters, Oct. 2, 2020, pp. 8039-8043.
Sabatini et al., "Protecting-Group-Free Amidation of Amino Acids using Lewis Acid Catalysts", Chemistry European Journal, 2018, 24, pp. 7033-7043.

(Continued)

*Primary Examiner* — Christina Bradley
(74) *Attorney, Agent, or Firm* — Wenderoth, Lind & Ponack, L.L.P.

(57) ABSTRACT

The present invention provides, as a novel compound that can be utilized for efficient synthesis or the like of a polypeptide comprising various amino acids, a silane-containing condensed cyclic dipeptide compound represented by formula (A).

(A)

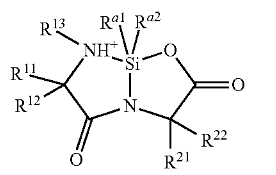

In formula (A), each of $R^{11}$, $R^{12}$, $R^{13}$, $R^{21}$, and $R^{22}$ independently represents a hydrogen atom, a halogen atom, a hydroxyl group, a carboxyl group, a nitro group, a cyano group, or a thiol group, or a monovalent aliphatic hydrocarbon group, aromatic hydrocarbon group, or heterocyclic group that may have one or more substituents; and each of $R^{a1}$ and $R^{a2}$ independently represents a monovalent aliphatic hydrocarbon group or aromatic hydrocarbon group that may have one or more substituents.

15 Claims, No Drawings

(56) References Cited

OTHER PUBLICATIONS

Gericke et al., "Ring-Strain-Formation Lewis Acidity? A Pentacoordinate Silacyclobutane Comprising Exclusively Equatorial Si—C Bonds", American Chemical Society, Organometallics, 2009, 28, pp. 6831-6834.

Lazareva et al., "Trans-Silylation of silatranes and 1, 2-dimethyl-2-azasilatran-3-one by Si-substituted trimethoxysilanes", Tetrahedron Letters, 2000, 41, pp. 4823-4826.

SILANE-CONTAINING CONDENSED CYCLIC DIPEPTIDE COMPOUND, PRODUCTION METHOD THEREFOR, AND METHOD FOR PRODUCING POLYPEPTIDE COMPOUND USING SAME

FIELD

The present invention relates to a novel silane-containing fused ring dipeptide compound and a production method thereof, as well as a method for producing a polypeptide compound using the silane-containing fused ring dipeptide compound.

BACKGROUND

Conventionally, amide compounds represented by peptides have been used in a wide variety of fields, including pharmaceuticals, cosmetics, and functional foods. Development of synthetic methods thereof has been diligently pursued as an important research goal in synthetic chemistry (Non-Patent Literature 1 to 3). However, there are few truly effective catalysts or reactants other than carboxylic acid activators for the amidation reaction, which is the most important reaction in peptide synthesis. Therefore, it is unavoidable to use a reaction mode that forms by-products, and thus, peptide synthesis, which involves repeating multi-stage reactions, is extremely inefficient from the viewpoint of atom economy (atomic yield). The amount of by-products is large, and there are few effective purification means. As a result, the cost of disposal of by-products and purification constitutes most of the necessary costs for peptide synthesis, and is the largest obstacle to development in this field.

In peptide synthesis, which uses amino acids or derivatives thereof as starting materials, it is desirable for the amidation reaction to proceed with high stereoselectivity. Enzyme reactions in the body are examples of highly stereoselective amidation reactions. For example, in the body, peptides are synthesized with extremely high stereoselectivity through sophisticated use of enzymes and hydrogen bonds. However, enzyme reactions are not suitable for mass production, requiring enormous financial and time costs when applied to synthetic chemistry.

In synthetic chemistry, amidation reactions using catalysts have been examined, but in conventional means, the amide bond is formed primarily through the method of activating carboxylic acid, such that racemization occurs quickly, whereby synthesizing a peptide with high stereoselectivity and efficiency is difficult.

According to conventional methods, it is very difficult to link an additional amino acid or derivative to a peptide comprising a plurality of amino acids or derivatives thereof (chemical ligation) or link two or more peptides via amide bonds. As an amidation method for ligation to such peptides, there are known a method for ligation by using an amino acid having a sulfur atom to utilize the high reactivity of the sulfur atom (Non-Patent Literature 4) and a method for ligation by synthesizing an amino acid hydroxyamine to utilize the high reactivity of the hydroxyamine (Non-Patent Literature 5). However, in the former method, it is difficult to synthesize amino acids having a sulfur atom, and in the latter method, hydroxyamine synthesis involving several steps is necessary. Both methods are time-consuming and costly and have a disadvantage in efficiency.

The present inventors have developed, as techniques for synthesizing an amide compound in a highly chemoselective manner: a method of amidating a carboxylic acid/ester compound having a hydroxy group at the β-position in the presence of a specific metal catalyst (Patent Literature 1); a method of using a hydroxyamino/imino compound as an amino acid precursor and amidating it in the presence of a specific metal catalyst, and then reducing them in the presence of a specific metal catalyst (Patent Literature 2); and a method of amidating a carboxylic acid/ester compound in the presence of specific metal catalyst (Patent Literature 3). The present inventors have also developed a technique for highly efficient and selective synthesis of peptides consisting of various amino acid residues by amide reaction of the carboxyl group of an N-terminal protected amino acid/peptide and the amino group of a C-terminal protected amino acid/peptide in the presence of a specific silylating agent and Lewis acid catalyst, followed by deprotection (Patent Literature 4).

In recent years, attempts have been made to synthesize peptides using unprotected amino acids (Patent Literature 6 to Patent Literature 8), but none of them were satisfactory in terms of the types of amino acids available or reaction efficiency.

CITATION LIST

Patent Literature

[Patent Literature 1] WO2017/204144A
[Patent Literature 2] WO2018/199146A
[Patent Literature 3] WO2018/199147A
[Patent Literature 4] WO2019/208731A

Non-Patent Literature

[Non-Patent Literature 1] Chem. Rev., 2011, 111, 6557-6602
[Non-Patent Literature 2] Org. Process Res. Dev., 2016, 20(2), 140-177
[Non-Patent Literature 3] Chem. Rev., 2016, 116, 12029-12122
[Non-Patent Literature 4] Science, 1992, 256, 221-225
[Non-Patent Literature 5] Angew. Chem. Int. Ed., 2006, 45, 1248-1252
[Non-Patent Literature 6] Chem. Eur. J. 2019, 25, 15091
[Non-Patent Literature 7] Org. Lett. 2020, 22, 8039
[Non-Patent Literature 8] Chem. Eur. J. 2018, 24, 7033

SUMMARY

Problem to be Solved

Against this background, an efficient method for synthesizing polypeptides composed of various amino acids has been sought. The present invention has been made in view of this problem.

Means for Solving the Problem

As a result of intensive investigations, the present inventors have found that a silane-containing fused ring dipeptide compound with a novel structure can be obtained via a reaction between a specific silyl dihalide compound and a specific silane compound substituted with a nitrogen-containing heterocyclic group in the presence of an unprotected amino acid, followed by a further reaction with an amino acid ester. The inventors have also found that this fused ring dipeptide compound can be reacted with an N-protected amino acid or peptide and then with a C-protected amino acid or peptide to thereby cause the N-terminal and C-terminal extensions of the cyclic dipeptide proceed in succession, making it possible to efficiently synthesize a polypeptide such as a tetrapeptide. Based on these findings, the inventors have completed the present invention.

Thus, the present invention provides the following aspects.

[Aspect 1]

A silane-containing fused ring dipeptide compound represented by formula (A).

[Chem. 1]

(A)

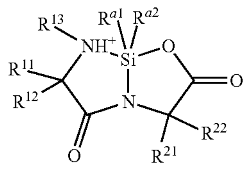

In formula (A), $R^{11}$, $R^{12}$, $R^{13}$, $R^{21}$, and $R^{22}$ represent, independently of each other, a hydrogen atom, halogen atom, hydroxyl group, carboxyl group, nitro group, cyano group, or thiol group, or a monovalent aliphatic hydrocarbon group, aromatic hydrocarbon group, or heterocyclic group that may have one or more substituents, and $R^{a1}$ and $R^{a2}$ represent, independently of each other, a monovalent aliphatic hydrocarbon group or aromatic hydrocarbon group that may have one or more substituents.

[Aspect 2]

A method for producing a silane-containing fused ring dipeptide compound according to Aspect 1, comprising:

(i) causing a reaction between a first silane compound represented by formula (S1) and a second silane compound represented by formula (S2) in the presence of an amino acid represented by formula (R2); and (ii) adding an amino acid ester represented by formula (R2) to the reactant from step (i) to cause a further reaction, thereby preparing the a silane-containing fused ring dipeptide compound represented by formula (A).

[Chem. 2]

(S1)

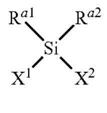

In formula (S1), $R^{a1}$ and $R^{a2}$ each represents the same definition as in formula (A), and $X^1$ and $X^2$ represent, independently of each other, a halogen atom.

[Chem. 3]

(S2)

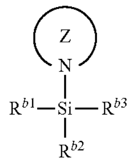

In formula (S2), $R^{b1}$, $R^{b2}$, and $R^{b3}$ represent, independently of each other, a hydrogen atom or halogen atom, or a monovalent aliphatic hydrocarbon group or aromatic hydrocarbon group that may have one or more substituents, and Z represents a 5- to 10-membered heterocyclic group that contain at least one nitrogen atom as a ring-constituting atom and that may have one or more substituents.

[Chem. 4]

(R1)

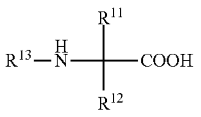

In formula (R1), $R^{11}$, $R^{12}$, and $R^{13}$ represent, independently of each other, the same definition as in formula (A).

[Chem. 5]

(R2)

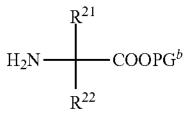

In formula (R2), $R^{21}$ and $R^{22}$, independently of each other, each represent the same definition as in formula (A), and $PG^b$ represents a protecting group for a carboxyl group.

[Aspect 3]

The method according to Aspect 2, wherein the reaction system in step (i) also contains a base and/or wherein the reaction system in step (ii) also contains a Lewis acid catalyst.

[Aspect 4]

A method for producing a polypeptide compound using a silane-containing fused ring dipeptide compound according to Aspect 1, comprising:

causing a reaction between a silane-containing fused ring dipeptide compound represented by formula (A), a protected amino acid or protected peptide compound represented by formula (R3), and an amino acid ester or peptide ester compound represented by formula (R4) to thereby produce a polypeptide compound represented by formula (P1).

[Chem. 6]

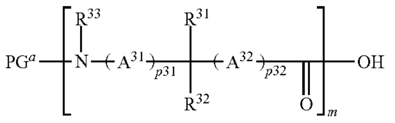

(R3)

In formula (R3), $PG^a$ represents a protecting group for an amino group, $R^{31}$ and $R^{32}$ represent, independently of each other, a hydrogen atom, halogen atom, hydroxyl group, carboxyl group, nitro group, cyano group, or thiol group, or an amino group, monovalent aliphatic hydrocarbon group, monovalent aromatic hydrocarbon group, or monovalent heterocyclic group that may have one or more substituents, $R^{33}$ represents a hydrogen atom, carboxyl group, hydroxyl group, or a monovalent aliphatic hydrocarbon group, aromatic hydrocarbon group, or heterocyclic group that may have one or more substituents and that may be bound to the nitrogen atom via a linking group, or $R^{31}$ and $R^{33}$ may be bound to each other to form, together with the carbon atom to which $R^{31}$ binds and the nitrogen atom to which $R^{33}$ binds, a hetero ring that may have one or more substituents, $A^{31}$ and $A^{32}$ represent, independently of each other, a divalent aliphatic hydrocarbon group containing 1 to 3 carbon atoms that may have one or more substituents, p31 and p32 represent, independently of each other, 0 or 1, m represents an integer of equal to or greater than 1 corresponding to the number of the structure units parenthesized with [ ], provided that when m is equal to or greater than 2, then the two or more structure units in [ ] may be either identical to each other or different from each other.

[Chem. 7]

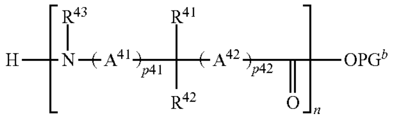

(R4)

In formula (R4), $PG^b$ represents a protecting group for a carboxyl group, $R^{41}$ and $R^{42}$ represent, independently of each other, a hydrogen atom, halogen atom, hydroxyl group, carboxyl group, nitro group, cyano group, or thiol group, or an amino group, monovalent aliphatic hydrocarbon group, monovalent aromatic hydrocarbon group, or monovalent heterocyclic group that may have one or more substituents, $R^{43}$ represents a hydrogen atom, carboxyl group, hydroxyl group, or a monovalent aliphatic hydrocarbon group, aromatic hydrocarbon group, or heterocyclic group that may have one or more substituents and that may be bound to the nitrogen atom via a linking group, or $R^{41}$ and $R^{43}$ may be bound to each other to form, together with the carbon atom to which $R^{41}$ binds and the nitrogen atom to which $R^{43}$ binds, a hetero ring that may have one or more substituents, $A^{41}$ and $A^{42}$ represent, independently of each other, a divalent aliphatic hydrocarbon group containing 1 to 3 carbon atoms that may have one or more substituents, p41 and p42 represent, independently of each other, 0 or 1, represents an integer of equal to or greater than 1 corresponding to the number of the structure units parenthesized with [ ], provided that when n is equal to or greater than 2, then the two or more structure units in [ ] may be either identical to each other or different from each other.

[Chem. 8]

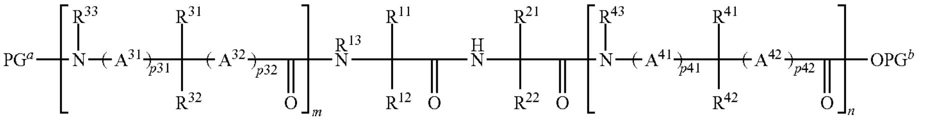

(P1)

In formula (P1), $R^{11}$, $R^{12}$, $R^{13}$, $R^{21}$, and $R^{22}$ each represent the same definition as in formula (A), $PG^a$, $R^{31}$, $R^{32}$, $R^{33}$, $A^{31}$, $A^{32}$, p31, p32, and m each represent the same definition as in formula (R3), and $PG^b$, $R^{41}$, $R^{42}$, $R^{43}$, $A^{41}$, $A^{42}$, p41, p42, and n each represent the same definition as in formula (R4).

[Aspect 5]

The method according to Aspect 4, comprising the steps of:

(i) causing a reaction between the silane-containing fused ring dipeptide compound represented by formula (A) and the protected amino acid or protected peptide compound represented by formula (R3); and (ii) causing a further reaction between the reactant from step (i) and the amino acid ester or peptide ester compound represented by formula (R4) to thereby prepare the polypeptide compound of formula (P1).

[Aspect 6]

The method according to Aspect 4, comprising the steps of:

(i) causing a reaction between the silane-containing fused ring dipeptide compound represented by formula (A) and the amino acid ester or peptide ester compound represented by formula (R4); and (ii) causing a further reaction between the reactant from step (i) and the protected amino acid or protected peptide represented by formula (R3) to thereby prepare the polypeptide compound of formula (P1).

[Aspect 7]

The method according to Aspect 5 or 6, wherein the reaction system in step (i) and/or (ii) contains a base and/or a condensing agent.

[Aspect 8]

The method according to any one of Aspects 4 to 7, further comprising the step of deprotecting the amino-protecting group $PG^a$ and/or the carboxyl-protecting group $PG^b$ in the polypeptide compound of formula (P1).

[Aspect 9]

A method of producing a polypeptide compound using a silane-containing fused ring dipeptide compound according to Aspect 1, comprising:

causing reactions among a silane-containing fused ring dipeptide compound represented by formula (A1), a silane-containing fused ring dipeptide compound represented by formula (A2), a protected amino acid or protected peptide compound represented by formula (R3), and an amino acid ester or peptide ester compound represented by formula (R4) to thereby prepare a polypeptide compound represented by formula (P2).

[Chem. 9]

(A1)

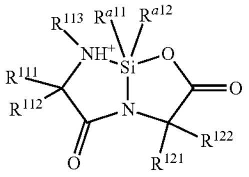

In formula (A1), $R^{111}$, $R^{112}$, $R^{113}$, $R^{121}$, and $R^{122}$ represent, independently of each other, a hydrogen atom, halogen atom, hydroxyl group, carboxyl group, nitro group, cyano group, or thiol group, or a monovalent aliphatic hydrocarbon group, aromatic hydrocarbon group, or heterocyclic group that may have one or more substituents, and $R^{a11}$ and $R^{a12}$ represent, independently of each other, a linear or cyclic aliphatic hydrocarbon group that may have one or more substituents.

[Chem. 10]

(A2)

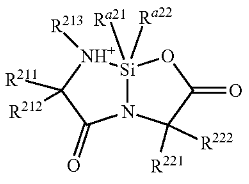

In formula (A2), $R^{211}$, $R^{212}$, $R^{213}$, $R^{221}$, and $R^{222}$ represent, independently of each other, a hydrogen atom, halogen atom, hydroxyl group, carboxyl group, nitro group, cyano group, or thiol group, or a monovalent aliphatic hydrocarbon group, aromatic hydrocarbon group, or heterocyclic group that may have one or more substituents, and $R^{a21}$ and $R^{a22}$ represent, independently of each other, a linear or cyclic aliphatic hydrocarbon group that may have one or more substituents.

[Chem. 11]

(R3)

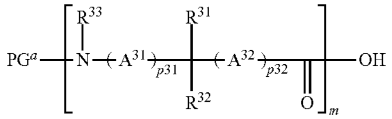

In formula (R3), $PG^a$ represents a protecting group for an amino group, $R^{31}$ and $R^{32}$ represent, independently of each other, a hydrogen atom, halogen atom, hydroxyl group, carboxyl group, nitro group, cyano group, or thiol group, or an amino group, monovalent aliphatic hydrocarbon group, monovalent aromatic hydrocarbon group, or monovalent heterocyclic group that may have one or more substituents, or $R^{31}$ and $R^{32}$ may be bound to each other to form, together with the carbon atom to which $R^{31}$ binds and the nitrogen atom to which $R^{32}$ binds, a hetero ring that may have one or more substituents, $R^{33}$ represents a hydrogen atom, carboxyl group, hydroxyl group, or a monovalent aliphatic hydrocarbon group, aromatic hydrocarbon group, or heterocyclic group that may have one or more substituents and that may be bound to the nitrogen atom via a linking group, $A^{31}$ and $A^{32}$ represent, independently of each other, a divalent aliphatic hydrocarbon group containing 1 to 3 carbon atoms that may have one or more substituents, p31 and p32 represent, independently of each other, 0 or 1, and m represents an integer of equal to or greater than 1 and corresponds to the number of the structure units parenthesized with [ ], provided that when m is equal to or greater than 2, then the two or more structure units in [ ] may be either identical to each other or different from each other.

[Chem. 12]

(R4)

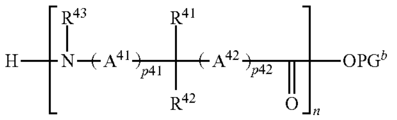

In formula (R4), $PG^b$ represents a protecting group for a carboxyl group, $R^{41}$ and $R^{42}$ represent, independently of each other, a hydrogen atom, halogen atom, hydroxyl group, carboxyl group, nitro group, cyano group, or thiol group, or an amino group, monovalent aliphatic hydrocarbon group, monovalent aromatic hydrocarbon group, or monovalent heterocyclic group that may have one or more substituents, or $R^{41}$ and $R^{42}$ may be bound to each other to form, together with the carbon atom to which $R^{41}$ binds and the nitrogen atom to which $R^{42}$ binds, a hetero ring that may have one or more substituents, $R^{43}$ represents a hydrogen atom, carboxyl group, hydroxyl group, or a monovalent aliphatic hydrocarbon group, aromatic hydrocarbon group, or heterocyclic group that may have one or more substituents and that may be bound to the nitrogen atom via a linking group, $A^{41}$ and $A^{42}$ represent, independently of each other, a divalent aliphatic hydrocarbon group containing 1 to 3 carbon atoms that may have one or more substituents, p41 and p42 represent, independently of each other, 0 or 1, and n represents an integer of equal to or greater than 1 corresponding to the number of the structure units parenthesized with [ ], provided that when n is equal to or greater than 2, then the two or more structure units in [ ] may be either identical to each other or different from each other.

[Chem. 13]

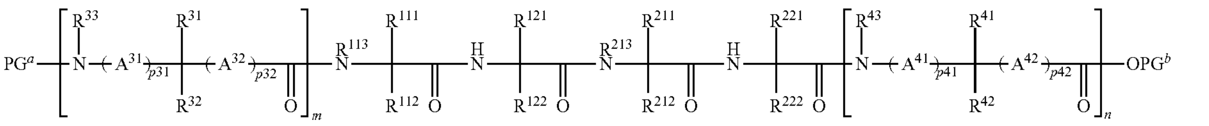

(P2)

In formula (P2), $R^{111}$, $R^{112}$, $R^{113}$, $R^{121}$, and $R^{122}$ each represents the same definition as in formula (A1), $R^{211}$, $R^{212}$, $R^{213}$, $R^{221}$, and $R^{222}$ each the formula (A2) represents the same definition as in the formula (A1), $PG^a$, $R^{31}$, $R^{32}$, $R^{33}$, $A^{31}$, $A^{32}$, p31, p32, and m each represent the same definition as in formula (R3), and $PG^b$, $R^{41}$, $R^{42}$, $R^{43}$, $A^{41}$, $A^{42}$, p41, p42, and n each represent the same definition as in formula (R4).

[Aspect 10]

The method according to Aspect 9, comprising the steps of:

(i) causing a reaction between the silane-containing fused ring dipeptide compound represented by formula (A1) compound and the protected amino acid or protected peptide compound represented by formula (R3);

(ii) causing a further reaction between the reactant from step (i) and the silane-containing fused ring dipeptide compound represented by formula (A2); and (iii) causing a further reaction between the reactant from step (ii) and the amino acid ester or peptide ester compound represented by formula (R4) to thereby prepare the polypeptide compound of formula (P1).

[Aspect 11]

The method according to Aspect 9, comprising the steps of:

(i) causing a reaction between the silane-containing fused ring dipeptide compound represented by formula (A2) and the amino acid ester or peptide ester compound represented by formula (R4);

(ii) causing a further reaction between the reactant from step (i) and the silane-containing fused ring dipeptide compound represented by formula (A1); and (iii) causing a further reaction between the reactant from step (ii) and the protected amino acid or protected peptide compound represented by formula (R3) to thereby prepare the polypeptide compound of formula (P1).

[Aspect 12]

The method according to Aspect 10 or 11, wherein the reaction system in step (i) and/or (ii) and/or (iii) contains a base and/or a condensing agent.

[Aspect 13]

The method according to any one of Aspects 9 to 12, further comprising the step of deprotecting the amino-protecting group $PG^a$ and/or the carboxyl-protecting group $PG^b$ in the polypeptide compound of formula (P2).

Effects

The present invention provides a silane-containing fused ring dipeptide compound having a novel structure and an efficient method for producing polypeptides using this compound.

EMBODIMENTS

The present invention is described hereinafter in detail with reference to specific embodiments thereof. However, the present invention is not limited to the following embodiments and can be carried out in any embodiment that does not deviate from the gist according to the present invention.

I. Overview

The present inventors have found that a silane-containing fused ring dipeptide compound with a novel structure can be obtained via a reaction between a specific silyl dihalide compound and a specific silane compound substituted with a nitrogen-containing heterocyclic group in the presence of an unprotected amino acid, followed by a further reaction with an amino acid ester. This is presumably because a silyl diimidazole having two nitrogen-containing hetero rings is formed in the system, which then causes a 5-membered ring formation reaction with a non-protected amino acid, a coupling reaction with an amino acid ester, hydrolysis of the amino acid ester, and another 5-membered ring formation reaction to proceed in succession. According to the investigations of the present inventors, this reaction proceeds with any combination of amino acids, and the corresponding fused ring dipeptide compound can be obtained in high yield (see Example Group I below). In addition, since both the N- and C-termini of the dipeptide are protected by easily deprotectable silicon, this fused ring dipeptide compound can be easily deprotected and used as a nucleophile or electrophile, making it an extremely useful compound (see Reference Example Group below).

In particular, the present inventors' further analysis has revealed that reacting this fused ring dipeptide compound with an N-protected amino acid and then with a C-protected amino acid leads to the progression of N-terminal and C-terminal elongations of the cyclized dipeptide in succession, enabling efficient one-pot synthesis of polypeptides such as tetrapeptides and pentapeptides. Furthermore, multiple fused ring dipeptide compounds can be used in this synthetic reaction, which makes it possible to synthesize even larger polypeptides such as hexapeptides with high efficiency (see Example Group II below).

In the following description, we will give the following explanations: the definitions of key terms used in this disclosure ([II. Definitions of Terms]); novel silane-containing fused ring dipeptide compounds provided herein (hereinafter also referred to as "fused ring dipeptide compounds according to the present invention") ([III. Fused Ring Dipeptide Compound according to Present Invention]); a method for producing the same using specific silyl dihalide compounds and specific silane compounds substituted with a nitrogen-containing heterocyclic group (hereinafter also referred to as "the production method of the fused ring dipeptide compound according to the present invention") ([IV. Production Method of Fused Ring Dipeptide Compound according to Present Invention]); and a novel method for producing a polypeptide using the fused ring dipeptide compound according to the present invention (hereinafter also referred to as "the polypeptide production method according to the present invention") ([V. Production Method of Polypeptide according to Present Invention]).

II. Definitions of Terms

The term "amino acid" herein refers to a compound having a carboxyl group and an amino group. Unless otherwise specified, the type of an amino acid is not particularly limited. For example, from the viewpoint of optical isomerism, an amino acid may be in the D-form, in the L-form, or in a racemic form. From the viewpoint of the relative positions of the carboxyl group and the amino group, an amino acid may be any of an α-amino acid, β-amino acid, γ-amino acid, δ-amino acid, or ε-amino acid. Examples of amino acids include, but are not limited to, natural amino acids that make up proteins. Examples include valine, leucine, isoleucine, alanine, arginine, glutamine, lysine, aspartic acid, glutamic acid, proline, cysteine, threonine, methionine, histidine, phenylalanine, tyrosine, tryptophan, asparagine, glycine, and serine.

The term "peptide" herein refers to a compound comprising a plurality of amino acids linked together via peptide bonds. Unless otherwise specified, the plurality of amino acid units constituting a peptide may be the same type of amino acid unit or may consist of two or more types of amino acid units. The number of amino acids constituting a peptide is not restricted as long as it is two or more. Examples include 2 (also called "dipeptide"), 3 (also called "tripeptide"), 4 (also called "tetrapeptide"), 5 (also called "pentapeptide"), 6, 7, 8, 9, 10, 15, 20, 30, 40, 50, 100, or more. The term "polypeptide" may also be used to refer to tripeptides and longer peptides.

The term "amino group" herein refers to a functional group represented by any formula of $-NH_2$, $-NRH$, and $-NRR'$ (where R and R' each represent a substituent) obtained by removing hydrogen from ammonia, a primary amine, and a secondary amine, respectively.

Unless otherwise specified, a hydrocarbon group herein may be either aliphatic or aromatic. An aliphatic hydrocarbon group may be in the form of either a chain or a ring. A chain hydrocarbon group may be linear or branched. A cyclic hydrocarbon group may be monocyclic, bridged cyclic, or spirocyclic. The hydrocarbon group may be saturated or unsaturated. In other words, one, two, or more carbon-carbon double and/or triple bonds may be included. Specifically, "hydrocarbon group" represents a concept including an alkyl group, alkenyl group, alkynyl group, cycloalkyl group, cycloalkenyl group, cycloalkynyl group, aryl group, etc. Unless otherwise specified, one, two, or more hydrogen atoms of the hydrocarbon group may be replaced with any substituents and one, two, or more carbon atoms in the hydrocarbon group may be replaced with any heteroatoms corresponding to the valence thereof.

The term "hydrocarbon oxy group" herein refers to a group comprising an oxy group ($-O-$) linked via one bond thereof to the hydrocarbon group as defined above.

The term "hydrocarbon carbonyl group" herein refers to a group comprising a carbonyl group ($-C(=O)-$) linked via one bond thereof to the hydrocarbon group as defined above.

The term "hydrocarbon sulfonyl group" herein refers to a group comprising a sulfonyl group ($-S(=O)_2-$) linked via one bond thereof to the hydrocarbon group as defined above.

A heterocyclic group may be saturated or unsaturated. In other words, it may contain one, two, or more carbon-carbon double and/or triple bonds. A heterocyclic group may be monocyclic, bridged cyclic, or spirocyclic. The heteroatom included in the constituent atoms of the heterocyclic group is not particularly limited, examples thereof including nitrogen, oxygen, sulfur, phosphorus, and silicon.

The term "heterocyclic oxy group" herein refers to a group comprising an oxy group ($-O-$) linked via one bond thereof to the heterocyclic group as defined above.

The term "heterocyclic carbonyl group" herein refers to a group comprising a carbonyl group ($-C(=O)-$) linked via one bond thereof to the heterocyclic group as defined above.

The term "heterocyclic sulfonyl group" herein refers to a group comprising a sulfonyl group ($-S(=O)_2-$) linked via one bond thereof to the heterocyclic group as defined above.

Unless otherwise specified, the term "substituent" herein refers, independently of each other, to any substituent which is not particularly limited so long as the amidation step of the production method according to the present invention proceeds. Examples include, but are not limited to, a halogen atom, hydroxyl group, carboxyl group, nitro group, cyano group, thiol group, sulfonic acid group, amino group, amide group, imino group, imide group, hydrocarbon group, heterocyclic group, hydrocarbon oxy group, hydrocarbon carbonyl group (acyl group), hydrocarbon oxycarbonyl group, hydrocarbon carbonyloxy group, hydrocarbon substitution amino group, hydrocarbon substitution amino carbonyl group, hydrocarbon carbonyl substitution amino group, hydrocarbon substitution thiol group, hydrocarbon sulfonyl group, hydrocarbon oxysulfonyl group, hydrocarbon sulfonyloxy group, heterocyclic oxy group, heterocyclic carbonyl group, heterocyclic oxycarbonyl group, heterocyclic carbonyloxy group, heterocyclic amino group, heterocyclic amino carbonyl group, heterocyclic carbonyl substitution amino group, heterocyclic substitution thiol group, heterocyclic sulfonyl group, heterocyclic oxysulfonyl group, and heterocyclic sulfonyloxy group. The term "substituents" also may include functional groups obtained by substituting any of the aforementioned functional groups with any of the aforementioned functional groups as long as the valence and physical properties thereof permit. When a functional group has one or more substituents, the number of the substituents is not particularly limited as long as the valence and physical properties thereof permit. When the functional group has two or more substituents, they may be identical to each other or different from each other.

The main abbreviations used herein are listed in Table 1 below.

TABLE 1

| Abbreviation | Definition |
|---|---|
| Ac | acetyl |
| acac | acetyl acetonate |
| Alloc | allyoxycarbonyl |
| Bn or Bzl | benzyl |
| Boc | tert-butoxycarbonyl |
| Bu | butyl |
| Bz | benzoyl |
| Cbz | benzyloxycarbonyl |
| Cp | cyclopentadienyl |
| 2,4-DNP | 2,4-dinitrophenyl |
| Et | ethyl |
| Fmoc | 9-fluorenylmethyloxycarbonyl |
| HOBt | 1-hydroxybenzotriazole |
| i-Pr | isopropyl |
| MABR | methylaluminum bis(4-bromo-2,6-di-tert-butylphenoxyde) |
| Me | methyl |
| Ms | mesyl |
| Ns | 2 or 4-nitrobenzenesulfonyl |
| Phth | phthaloyl |
| PMB | paramethoxybenzyl |
| PMPCO | paramethoxybenzoyl |
| Pr | propyl |
| TBAF | tetrabutylammonium fluoride |
| TBDPS | tert-butyl diphenylsilyl |
| TBS | tritert-butylsilyl |
| t-Bu | tert-butyl |
| TES | triethylsilyl |
| Tf | trifluoromethane sulfonyl |
| THF | tetrahydrofuran |
| TIPS | triisopropylsilyl |
| TMS | trimethylsilyl |
| TMS-IM | trimethylsilyl imidazole |
| TMS-OTf | trimethylsilyl trifluoromethanesulfonate |
| Troc | 2,2,2-trichloroethoxy carbonyl |
| Trt | trityl |
| Ts | toluenesulfonyl |
| wscHCl | 1-ethyl-3-(3-dimethylaminopropyl)carbodiimide hydrochloride |

Amino acids and residues thereof may herein be represented by three-letter abbreviations well known to a person skilled in the art. The three-letter abbreviations of major amino acids are shown in the following table.

TABLE 2

| | |
|---|---|
| Ala | Alanine |
| Arg | Arginine |
| Asn | Asparagine |
| Asp | Aspartic acid |
| Cys | Cysteine |
| Gln | Glutamine |
| Glu | glutamic acid |
| Gly | Glycine |
| His | Histidine |
| Ile | Isoleucine |
| Leu | Leucine |
| Lys | Lysine |
| Met | Methionine |
| Phe | Phenylalanine |
| Phg | Phenylglycine |
| Pro | Proline |
| Ser | Serine |
| Thr | Threonine |
| Trp | Tryptophan |
| Tyr | Tyrosine |
| Val | Valine |

β-homoamino acids and residues thereof may herein be represented by "Ho" followed by three-letter abbreviations of corresponding R-amino acids.

III. Fused Ring Dipeptide Compound of Present Invention

An embodiment according to the present invention relates to a novel silane-containing fused ring dipeptide compound represented by formula (A) (hereinafter also referred to as a "fused ring dipeptide compound according to the present invention").

[Chem. 14]

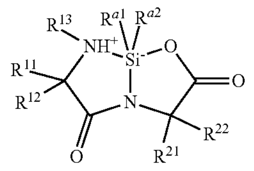

(A)

In formula (A), $R^{11}$, $R^{12}$, $R^{13}$, $R^{21}$, and $R^{22}$ represent, independently of each other, a hydrogen atom, halogen atom, hydroxyl group, carboxyl group, nitro group, cyano group, or thiol group, or a monovalent aliphatic hydrocarbon group, aromatic hydrocarbon group, or heterocyclic group that may have one or more substituents. If these groups have one or more substituents, they may be selected arbitrarily from those detailed earlier. If these groups have one or more substituents, they may be selected arbitrarily from those detailed earlier. The number of substituents is not restricted, but may be 5, 4, 3, 2, 1, or 0.

In formula (A), when $R^{11}$, $R^{12}$, $R^{13}$, $R^{21}$, and/or $R^{22}$ are a monovalent aliphatic hydrocarbon group, aromatic hydrocarbon group, or heterocyclic group that may have one or more substituents, a linking group may intervene between the aliphatic hydrocarbon group, aromatic hydrocarbon group, or heterocyclic group and the carbon atom to which it binds. The linking group may be, independently of each other, selected from, although is not limited to, the structures listed below (where, in the chemical formulae below, A represents, independently of each other, a monovalent aliphatic hydrocarbon group, aromatic hydrocarbon group, or heterocyclic group that may have one or more substituents. When two A's are present in the same group, they may be identical to each other or different from each other.).

[Chem. 15]

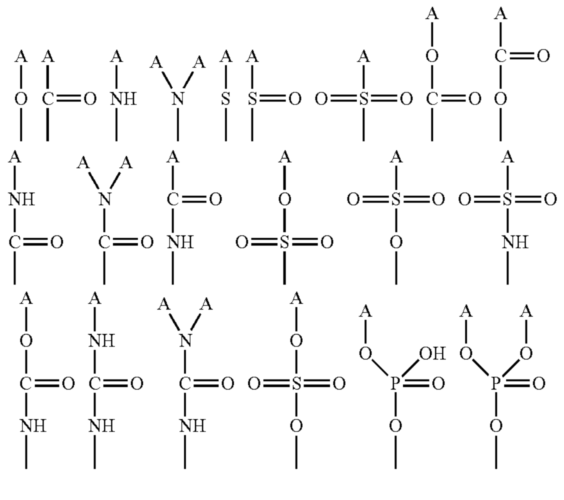

-continued

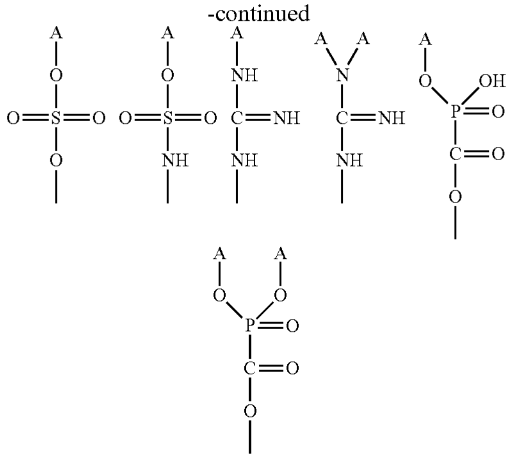

In formula (A), when each of $R^{11}$, $R^{12}$, $R^{13}$, $R^{21}$, and/or $R^{22}$ is an aliphatic hydrocarbon group (that may have one or more substituents), the number of carbon atoms in the aliphatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aliphatic hydrocarbon group, but may be 1 or more in the case of alkyl groups, 2 or more in the case of alkenyl groups or alkynyl groups, and 3 or more, for example 4 or more, or 5 or more in the case of cycloalkyl groups. Specific examples of the number of atoms include 1, 2, 3, 4, 5, 6, 7, 8, 9, 10, 11, 12, 13, 14, 15, 16, 17, 18, 19, or 20.

In formula (A), when each of $R^{11}$, $R^{12}$, $R^{13}$, $R^{21}$, and/or $R^{22}$ is an aromatic hydrocarbon group (that may have one or more substituents), the number of carbon atoms in the aromatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aromatic hydrocarbon group, but may be typically 4 or more, for example 5 or more, or 6 or more. Specific examples of the number of atoms include 4, 5, 6, 7, 8, 9, 10, 11, 12, 13, 14, 15, 16, 17, 18, 19, or 20.

In formula (A), when each of $R^{11}$, $R^{12}$, $R^{13}$, $R^{21}$, and/or $R^{22}$ is a heterocyclic group (that may have one or more substituents), the total number of carbon atoms and hetero atoms in the heterocyclic group (when it has one or more substituents, including the number of atoms in the substituents) may be, although is not particularly limited to, typically 20 or less, 15 or less, 10 or less, 8 or less, or 6 or less. The lower limit thereof depends on the type of the heterocyclic structure, but may be typically 3 or more, for example 4 or more, or 5 or more. Specific examples of the number of atoms include 3, 4, 5, 6, 7, 8, 9, 10, 11, 12, 13, 14, 15, 16, 17, 18, 19, or 20.

Among them, each of $R^{11}$, $R^{12}$, $R^{21}$, and $R^{22}$ in formula (A) may preferably be, independently of each other, a hydrogen atom, hydroxyl group, thiol group, carboxyl group, nitro group, cyano group, or halogen atom, or, that may have one or more substituents, amino group, alkyl group, alkenyl group, alkynyl group, cycloalkyl group, alkoxy group, aryl group, aryloxy group, acyl group, heterocyclic group, or heterocyclic oxy group.

Specific examples of $R^{11}$, $R^{12}$, $R^{13}$, $R^{21}$, and $R^{22}$ in formula (A) may include, although are not limited to, the following.

*Hydrogen atom, hydroxyl group, thiol group, carboxyl group, nitro group, and cyano group;

*Halogen atoms such as fluorine atom, chlorine atom, bromine atom, and iodine atom;

*Alkyl groups such as methyl group, ethyl group, propyl group, isopropyl group, n-butyl group, isobutyl group, tert-butyl group, sec-butyl group, pentyl group, isopentyl group, neopentyl group, hexyl group, heptyl group, octyl group, decyl group, and nonyl group;

*Alkenyl groups such as ethenyl group, propenyl group, allyl group, butenyl group, pentenyl group, hexenyl group, heptenyl group, and octenyl group;

*Alkynyl groups such as propargyl group;

*Cycloalkyl groups such as cyclopropyl group, cyclobutyl group, cyclopentyl group, cyclohexyl group, cycloheptyl group, bicyclooctyl group, and spirooctyl group;

*Alkoxy groups such as methoxy group, ethoxy group, propoxy group, butoxy group, sec-butoxy group, and tert-butoxy group;

*Aryl groups such as phenyl group, benzyl group, tolyl group, naphthyl group, and anthracenyl group;

*Aryloxy groups such as phenyloxy group, benzyloxy group, and naphthyloxy group;

*Acyl groups such as acetyl group, propionyl group, benzoyl group, p-methoxybenzoyl group, and cinnamoyl group;

*Unsubstituted amino group and substitution amino groups such as dimethylamino group, benzylamino group, and triphenylmethylamino group;

*Heterocyclic groups such as furanyl group, thiophenyl group, pyranyl group, pyrrolinyl group, pyrrolyl group, 2,3-dihydro-1H-pyrrolyl group, piperidinyl group, piperazinyl group, homopiperazinyl group, morpholino group, thiomorpholino group, 1,2,4,6-tetrahydro pyridyl group, hexahydro pyrimidyl group, hexahydro pyridazyl group, 1,2,4,6-tetrahydro pyridyl group, 1,2,4,6-tetrahydro pyridazyl group, 3,4-dihydropyridyl group, imidazolyl group, 4,5-dihydro-1H-imidazolyl group, 2,3-dihydro-1H-imidazolyl group, pyrazolyl group, 4,5-dihydro-1H-pyrazolyl group, 2,3-dihydro-1H-pyrazolyl group, oxazolyl group, 4,5-dihydro-1,3-oxazolyl group, 2,3-dihydro-1,3-oxazolyl group, 2,5-dihydro-1,3-oxazolyl group, thiazolyl group, 4,5-dihydro-1,3-thiazolyl group, 2,3-dihydro-1,3-thiazolyl group, 2,5-dihydro-1,3-thiazolyl group, carbazolyl group;

*Heterocyclic oxy groups such as furanyl oxy group, pyrrolyl oxy group, indolyl oxy group, and quinolyl oxy group; and

*Groups derived from any of the groups mentioned above via substitution with 1 or more substituents (e.g., halogens).

Of the groups mentioned above, those having a carboxyl group may or may not have a protective group. Protecting groups for a carboxyl group will be explained later.

In formula (A), $R^{a1}$ and $R^{a2}$ represent, independently of each other, a monovalent aliphatic hydrocarbon group or aromatic hydrocarbon group that may have one or more substituents. If these groups have one or more substituents, they may be selected arbitrarily from those detailed earlier. The number of substituents is not restricted, but may be 5, 4, 3, 2, 1, or 0.

When each of $R^{a1}$ and/or $R^{a2}$ is an aliphatic hydrocarbon group (that may have one or more substituents), the number of carbon atoms in the aliphatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aliphatic hydrocarbon group, but may be 1 or more in the case of alkyl groups, 2 or more in the case of alkenyl groups or alkynyl groups, and 3 or more, for example 4 or more, or 5 or more in the case of cycloalkyl groups. Specific examples of the number of atoms include 1, 2, 3, 4, 5, 6, 7, 8, 9, 10, 11, 12, 13, 14, 15, 16, 17, 18, 19, or 20.

When each of $R^{a1}$ and/or $R^{a2}$ is an aromatic hydrocarbon group (that may have one or more substituents), the number of carbon atoms in the aromatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aromatic hydrocarbon group, but may be typically 4 or more, for example 5 or more, or 6 or more. Specific examples of the number of atoms include 4, 5, 6, 7, 8, 9, 10, 11, 12, 13, 14, 15, 16, 17, 18, 19, or 20.

Among them, each of $R^{a1}$ and $R^{a2}$ may, independently of each other, preferably be an alkyl group, alkenyl group, alkynyl group, cycloalkyl group, or aryl group that may have one or more substituents.

Specific examples of $R^{a1}$ and $R^{a2}$ may include, although are not limited to, the following.

*Alkyl groups such as methyl group, ethyl group, propyl group, isopropyl group, n-butyl group, isobutyl group, tert-butyl group, sec-butyl group, pentyl group, isopentyl group, neopentyl group, hexyl group, heptyl group, octyl group, decyl group, and nonyl group;

*Alkenyl groups such as ethenyl group, propenyl group, allyl group, butenyl group, pentenyl group, hexenyl group, heptenyl group, and octenyl group;

*Alkynyl groups such as propargyl group;

*Cycloalkyl groups such as cyclopropyl group, cyclobutyl group, cyclopentyl group, cyclohexyl group, cycloheptyl group, bicyclooctyl group, and spirooctyl group;

*Aryl groups such as phenyl group, benzyl group, tolyl group, naphthyl group, and anthracenyl group; and The fused ring dipeptide compound according to the present invention has a very characteristic structure in which a dipeptide consisting of two α-amino acid residues cyclizes to form a fused ring with two five-membered rings sharing a silicon atom and a nitrogen atom. In addition, since this compound is protected at both the N- and C-termini of the dipeptide with easily deprotectable silicon atoms, it can be easily deprotected in the presence of an acid or a base, and can be used as either a nucleophilic or electrophilic species, as shown in Reference Examples 1 and 2 below. Furthermore, the fused ring dipeptide compound according to the present invention is stable in air and easy to handle. Therefore, it can be used as a substrate for the peptide production reaction described below and is expected to have a variety of other applications.

IV. Production Method of Fused Ring Dipeptide Compound of Present Invention

An embodiment according to the present invention relates to a method for producing the fused ring dipeptide compound according to the present invention using a specific silyl dihalide compound and a specific silane compound having a nitrogen-containing heterocyclic substituent (the production method of the fused ring dipeptide compound according to the present invention).

The production method of the fused ring dipeptide compound according to the present invention includes at least the following steps.

(i) The step of causing a reaction between a first silane compound represented by formula (S1) and a second silane compound represented by formula (S2) by adding an amino acid represented by formula (R2).

(ii) The step of causing a further reaction between the reactant from step (i) and an amino acid ester represented by formula (R2) to thereby prepare the silane-containing fused ring dipeptide compound represented by formula (A).

*Amino Acid and Amino Acid Ester (Substrate Compound):

The amino acid and the amino acid ester to be used as substrates in the production method of the fused ring dipeptide compound according to the present invention are represented by the following formulae.

[Chem. 16]

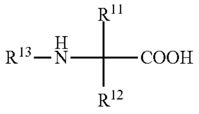

(R1)

[Chem. 17]

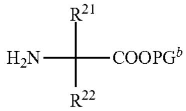

(R2)

$R^{11}$, $R^{12}$, and $R^{13}$ in formula (R1) and $R^{21}$ and $R^{22}$ in formula (R2) each represent, independently of each other, the same definition in formula (A), i.e., a hydrogen atom, halogen atom, hydroxyl group, carboxyl group, nitro group, cyano group, or thiol group, or a monovalent aliphatic hydrocarbon group, aromatic hydrocarbon group, or heterocyclic group that may have one or more substituents, the details of which were explained earlier.

In formula (R2), $PG^b$ represents a protecting group for a carboxyl group. $PG^b$ is not restricted as long as the carboxyl group concerned can be protected so as not to react during a given reaction, and can be deprotected and converted to a carboxyl group after the reaction. The details for the protecting group for a carboxyl group will be explained later.

Examples of the amino acid represented by formula (R1) and the amino acid from which the amino acid ester represented by formula (R2) is derived (i.e., the amino acid having no carboxyl-protecting group $PG^b$) include arbitrary α-amino acids. Specific examples include, although are not limited to, 20α-amino acids that make up biological proteins, i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, as well as ornithine, 2-amino isobutyric acid, methyl alanine, phenylglycine, and cyclohexyl alanine. Other specific examples include amino acids derived from these α-amino acids by substituting their side chains with one or more substituents (e.g., halogens) and/or one or more protecting groups (protecting groups for a carboxyl group and/or an amino group) explained below, for example, t-butyl-substituted asparagine, t-butyl-substituted glutamine, t-butyl-substituted serine, t-butyl-substituted threonine, t-butyl-substituted tryptophan, t-butyl-substituted lysine, Boc-substituted asparagine, Boc-substituted glutamine, Boc-substituted serine, Boc-substituted threonine, Boc-substituted tryptophan, Boc-substituted lysine, t-butyl-substituted aspartic acid, t-butyl-substituted glutamic acid, trityl-substituted asparagine, trityl-substituted glutamine, trityl-substituted histidine, t-butyl-substituted tyrosine, methyl-substituted tyrosine, methyl-substituted threonine, methyl-substituted serine, Cbz-substituted lysine, and Fmoc-substituted lysine. The optical isomerism of these α-amino acids is not restricted, and may be in the L-form, in the D-form, or in a racemic form.

*Protecting Group for a Carboxyl Group:

Examples of protecting groups for a carboxyl group (carboxyl-protecting groups) $PG^b$ to be used in each of the production methods according to the present invention (i.e., the production method of the fused ring dipeptide compound according to the present invention as well as the first and second polypeptide production methods according to the present invention, which will be explained later) include monovalent aliphatic hydrocarbon groups, aromatic hydrocarbon groups, and heterocyclic groups that may have one or more substituents. The details of the substituents, if any, are described above. Specific examples of the number of substituents are 5, 4, 3, 2, 1, or 0.

When the carboxyl-protecting group $PG^b$ is an aliphatic hydrocarbon group, the number of carbon atoms in the aliphatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aliphatic hydrocarbon group, but may be 1 or more in the case of alkyl groups, 2 or more in the case of alkenyl groups or alkynyl groups, 3 or more, for example 4 or more, or 5 or more in the case of cycloalkyl groups. Specific examples of the number of atoms include 1, 2, 3, 4, 5, 6, 7, 8, 9, 10, 11, 12, 13, 14, 15, 16, 17, 18, 19, or 20.

When the carboxyl-protecting group $PG^b$ is an aromatic hydrocarbon group, the number of carbon atoms in the aromatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aromatic hydrocarbon group, but may be typically 4 or more, for example 5 or more, or 6 or more. Specific examples of the number of atoms include 4, 5, 6, 7, 8, 9, 10, 11, 12, 13, 14, 15, 16, 17, 18, 19, or 20.

Specific examples of carboxyl-protecting groups $PG^b$ may include, although are not limited to, the following.

*Alkyl groups such as methyl group, ethyl group, propyl group, isopropyl group, n-butyl group, isobutyl group, tert-butyl group, sec-butyl group, pentyl group, isopentyl group, neopentyl group, hexyl group, heptyl group, octyl group, decyl group, and nonyl group;

*Alkenyl groups such as ethenyl group, propenyl group, allyl group, butenyl group, pentenyl group, hexenyl group, heptenyl group, and octenyl group;

*Alkynyl groups such as propargyl group;

*Cycloalkyl groups such as cyclopropyl group, cyclobutyl group, cyclopentyl group, cyclohexyl group, cycloheptyl group, bicyclooctyl group, and spirooctyl group;

*Aryl and arylalkyl groups such as phenyl, benzyl, tolyl, cumyl, 1,1-diphenylethyl, triphenylmethyl, fluorenyl, naphthyl and anthracenyl groups;

*Heterocyclic groups such as furanyl group, thiophenyl group, pyranyl group, pyrrolinyl group, pyrrolyl group, 2,3-dihydro-1H-pyrrolyl group, piperidinyl group, piperazinyl group, homopiperazinyl group, morpholino group, thiomorpholino group, 1,2,4,6-tetrahydro pyridyl group, hexahydro pyrimidyl group, hexahydro pyridazyl group, 1,2,4,6-tetrahydro pyridyl group, 1,2,4,6-tetrahydro pyridazyl group, 3,4-dihydropyridyl group, imidazolyl group, 4,5-dihydro-1H-imidazolyl group, 2,3-dihydro-1H-imidazolyl group, pyrazolyl group, 4,5-dihydro-1H-pyrazolyl group, 2,3-dihydro-1H-pyrazolyl group, oxazolyl group, 4,5-dihydro-1,3-oxazolyl group, 2,3-dihydro-1,3-oxazolyl group, 2,5-dihydro-1,3-oxazolyl group, thiazolyl group, 4,5-dihydro-1,3-thiazolyl group, 2,3-dihydro-1,3-thiazolyl group, 2,5-dihydro-1,3-thiazolyl group, and carbazolyl group; and

*Silicon-based protective groups such as trimethylsilyl (TMS) group, triethylsilyl (TES) group, triisopropylsilyl (TIPS) group, tri(tert-butyl)silyl (TBS) group, tert-butyldiphenylsilyl (TBDPS) group and tris(trialkylsilyl)silyl group.

According to an embodiment, aryl and arylalkyl groups such as cumyl groups may be preferred as the protecting group $PG^b$ of the carboxyl group of the amino acid ester of formula (R2). In particular, the use of these groups as protective groups $PG^b$ may make it possible to obtain the fused ring dipeptide compound of the present invention in high yield without the use of Lewis acid catalysts. In addition, when the amino acid ester represented by formula (R2) used is an ester of an amino acid which tends to be relatively racemized, such as phenylalanine and cysteine, the use of such an aryl or arylalkyl group as the carboxyl-protecting group $PG^b$ may help suppress racemization and improve the diastereomeric ratio.

*First and Second Silane Compounds:

The production method of the fused ring dipeptide compound according to the present invention is characterized by using two silane compounds in combination, i.e., the first silane compound of formula (S1) and the second silane compound of formula (S2).

The first silane compound is represented by formula (S1).

[Chem. 18]

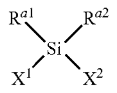

(S1)

In formula (S1), $R^{a1}$ and $R^{a2}$ have the same definition as in formula (A).

In formula (S1), $X^1$ and $X^2$ represent, independently of each other, a halogen atom such as fluorine, chlorine, bromine, and iodine, of which fluorine or chlorine is preferred.

Specific examples of the first silane compounds represented by formula (S1) include, although are not limited to, dimethyl dichlorosilane, methyl ethyl dichlorosilane, diethyl dichlorosilane, methylphenyl dichlorosilane, ethylphenyl dichlorosilane, diphenyl dichlorosilane, dichlorosilacyclobutane, and dichlorosilacyclopentane.

The second silane compound is represented by formula (S2).

[Chem. 19]

(S2)

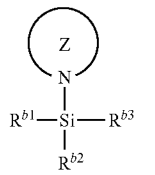

In formula (S2), $R^{b1}$, $R^{b2}$, and $R^{b3}$ represent, independently of each other, a hydrogen atom or halogen atom, or, that may have one or more substituents, aliphatic hydrocarbon group or aromatic hydrocarbon group. If these groups have one or more substituents, they may be selected arbitrarily from those detailed earlier. The number of substituents is not restricted, but may be 5, 4, 3, 2, 1, or 0.

The number of carbon atoms in the aliphatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aliphatic hydrocarbon group, but may be 1 or more in the case of alkyl groups, 2 or more in the case of alkenyl groups or alkynyl groups, 3 or more, for example 4 or more, or 5 or more in the case of cycloalkyl groups. Specific examples of the number of atoms include 1, 2, 3, 4, 5, 6, 7, 8, 9, 10, 11, 12, 13, 14, 15, 16, 17, 18, 19, or 20.

The number of carbon atoms in the aromatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aromatic hydrocarbon group, but may be typically 4 or more, for example 5 or more, or 6 or more. Specific examples of the number of atoms include 4, 5, 6, 7, 8, 9, 10, 11, 12, 13, 14, 15, 16, 17, 18, 19, or 20.

Among them, $R^{b1}$, $R^{b2}$, and $R^{b3}$ may preferably be, independently of each other, an alkyl group, alkenyl group, alkynyl group, cycloalkyl group, or aryl group that may have one or more substituents.

$R^{b1}$, $R^{b2}$, and $R^{b3}$ Specific examples of may include, although are not limited to, the following.

*Alkyl groups such as methyl group, ethyl group, propyl group, isopropyl group, n-butyl group, isobutyl group, tert-butyl group, sec-butyl group, pentyl group, isopentyl group, neopentyl group, hexyl group, heptyl group, octyl group, decyl group, and nonyl group;

*Alkenyl groups such as ethenyl group, propenyl group, allyl group, butenyl group, pentenyl group, hexenyl group, heptenyl group, and octenyl group;

*Alkynyl groups such as propargyl group;

*Cycloalkyl groups such as cyclopropyl group, cyclobutyl group, cyclopentyl group, cyclohexyl group, cycloheptyl group, bicyclooctyl group, and spirooctyl group;

*Aryl groups such as phenyl group, benzyl group, tolyl group, naphthyl group, anthracenyl group;

*Groups derived from any of the groups mentioned above via substitution with 1 or more substituents (e.g., halogens).

In formula (S2), Z represents a 5- to 10-membered (preferably 5-membered, 6-membered, or 10-membered) heterocyclic group that may have one or more substituents and that contains as one or more (preferably 2 to 4, more preferably 2 or 3) nitrogen atoms ring-constituting atoms. When the heterocyclic group has one or more substituents, the types of the substituents are as described above. Preferred among them include alkyl groups (e.g., straight chain or branched chain alkyl groups containing 1 to 10 carbon atoms, which may also be referred to as —R), alkoxy groups (—O—R), amino groups (—$NH_2$), alkylamino groups (—NHR), dialkylamino group (—$NR_2$, where the two alkyl groups R may be either the same or different), thioalkyl groups (—SR), as well as groups derived from these groups via substitution with one or more halogen atoms (e.g., bromine or chlorine atom) で substitution. Specific examples of the number of substituents are 10, 9, 8, 7, 6, 5, 4, 3, 2, 1, or 0. When there are two or more substituents, these may be either identical to each other or different from each other.

Specific examples of the nitrogen-containing heterocyclic groups $Z^c$ include, although are not limited to, pyrrole group, imidazole group, pyrazole group, triazole group (e.g., 1,2,3-triazole group and 1,2,4-triazole group), piperidyl group, piperidinyl group, piperazinyl group, tetrazole group, indole group, and benzimidazole group, as well as groups derived from these groups via substitution with groups mentioned above, such as (2-/3-/4-/5-)methyl imidazole group and (2,3-/2,4-/2,5-)dimethyl imidazole group. Preferred among them include imidazole group, pyrazole group, triazole group, and 2-methyl imidazole group.

Specific examples of the second silane compounds represented by formula (S2) include, although are not limited to, trimethylsilyl imidazole, triethylsilyl imidazole, triisopropylsilyl imidazole, and tri-tert-butyldimethylsilylimidazole.

*Lewis Acid Catalyst:

In the production method of the fused ring dipeptide compound according to the present invention, the reaction system may also contain a Lewis acid catalyst. Carrying out a reaction with a Lewis acid catalyst in the reaction system may lead to various advantages, such as improved reaction yield and stereoselectivity. On the other hand, however, when a Lewis acid catalyst is used, it may be necessary to separate and remove the Lewis acid catalyst from the reaction product. Therefore, it is preferable to determine whether to use a Lewis acid catalyst taking into consideration the purpose of using the production method according to the present invention. In particular, as mentioned above, when an aryl group such as a cumyl group or an arylalkyl group is used as a protective group $PG^b$ of the carboxyl group in the amino acid ester represented by formula (R2), the fused ring dipeptide compound according to the present invention may be obtained in high yield even without using a Lewis acid catalyst.

When a Lewis acid catalyst is used in the production method of the fused ring dipeptide compound according to the present invention, the type of catalyst is not limited, but it may preferably be a metal compound that functions as a Lewis acid. Examples of metal elements constituting the metal compound include various metals belonging to groups 2 through 15 of the periodic table. Examples of such metal elements include boron, magnesium, aluminum, gallium, indium, silicon, calcium, lead, bismuth, mercury, transition metals, and lanthanoid elements. Examples of transition metals include scandium, titanium, vanadium, chromium, manganese, iron, cobalt, nickel, copper, zinc, yttrium, zirconium, niobium, molybdenum, technetium, ruthenium, rhodium, palladium, tin, silver, cadmium, hafnium, tantalum, tungsten, rhenium, osmium, iridium, platinum, gold, and thallium. Examples of lanthanoid elements include lanthanum, cerium, neodymium, samarium, europium, gadolinium, holmium, erbium, thulium, ytterbium. From the viewpoint of excellent reaction acceleration and highly stereoselective production of amide compounds, the metal element may preferably be one or more selected from titanium, zirconium, hafnium, tantalum, niobium, boron, vanadium, tungsten, neodymium, iron, lead, cobalt, copper, silver, palladium, tin, and thallium, more preferably one or more selected from titanium, zirconium, hafnium, tantalum, and niobium. The metal compound may contain one, two or more metal atoms. If the metal compound contains two or more metal atoms, the two or more metal atoms may be either of the same metal element or of different metal elements.

Ligands constituting the metal compound may be selected according to the type of the metal element. Examples of ligands include: substituted or unsubstituted linear- or branched-chain alkoxy groups containing 1 to 10 carbon atoms, such as methoxy group, ethoxy group, propoxy group, butoxy group, trifluoroethoxy group, and trichloroethoxy group; halogen atoms such as fluorine atom, chlorine atom, bromine atom, iodine atom; aryloxy groups having 1 to 10 carbon atoms; acetylacetonate group (acac), acetoxy group (AcO), trifluoromethane sulfonate group (TfO); substituted or unsubstituted linear- or branched-chain alkyl groups having 1 to 10 carbon atoms; phenyl group, oxygen atom, sulfur atom, group —SR (where R represents a substituent exemplified by substituted or unsubstituted hydrocarbon groups containing 1 to 20 carbon atoms), group —NRR' (where R and R', independently of each other, represent a hydrogen atom or a substituent exemplified by substituted or unsubstituted hydrocarbon groups containing 1 to 20 carbon atoms), and cyclopentadienyl (Cp) group.

Preferred metal compounds among these are titanium compounds, zirconium compounds, hafnium compounds, tantalum compounds, or niobium compounds. Examples of these metal compounds are indicated below. Any one of these may be used alone, or two or more may be used together in any combination and ratio.

Examples of titanium compounds include those represented by $TiX^1_4$ (where 4 $X^1$'s, independently of each other, represent any of the ligands exemplified above, provided that 4 $X^1$'s may be the same type of ligand or different from each other.). When $X^1$ is an alkoxy group, it may preferably be a linear- or branched-chain alkoxy group having 1 to 10 carbon atoms, more preferably a linear- or branched-chain alkoxy group having 1 to 5 carbon atoms, still more preferably a linear- or branched-chain alkoxy group having 1 to 4 carbon atoms. When $X^1$ is an aryloxy group, it may preferably be an aryloxy group having 1 to 20 carbon atoms, more preferably an aryloxy group having 1 to 15 carbon atoms, still more preferably an aryloxy group having 1 to 10 carbon atoms. These ligands may have one or more substituents. When $X^1$ is a halogen atom, it may preferably be a chlorine atom or a bromine atom. Preferred examples of titanium compounds include $Ti(OMe)_4$, $Ti(OEt)_4$, $Ti(OPr)_4$, $Ti(Oi\text{-}Pr)_4$, $Ti(OBu)_4$, $Ti(Ot\text{-}Bu)_4$, $Ti(OCH_2CH(Et)Bu)_4$, $CpTiCl_3$, $Cp_2TiCl_2$, $Cp_2Ti(OTf)_2$, $(i\text{-}PrO)_2TiCl_2$, and $(i\text{-}PrO)_3TiCl$.

Examples of zirconium compounds include those represented by $ZrX^2_4$ (where 4 $X^2$'s, independently of each other, represent any of the ligands exemplified above, provided that 4 $X^2$'s may be the same type of ligand or different from each other.). When $X^2$ is an alkoxy group, it may preferably be a linear- or branched-chain alkoxy group having 1 to 10 carbon atoms, more preferably a linear- or branched-chain alkoxy group having 1 to 5 carbon atoms, still more preferably a linear- or branched-chain alkoxy group having 1 to 4 carbon atoms. When $X^2$ is an aryloxy group, it may preferably be an aryloxy group having 1 to 20 carbon atoms, more preferably an aryloxy group having 1 to 15 carbon atoms, still more preferably an aryloxy group having 1 to 10 carbon atoms. These ligands may have one or more substituents. When $X^2$ is a halogen atom, it may preferably be a chlorine atom or a bromine atom. Preferred examples of zirconium compounds include $Zr(OMe)_4$, $Zr(OEt)_4$, $Zr(OPr)_4$, $Zr(Oi\text{-}Pr)_4$, $Zr(OBu)_4$, $Zr(Ot\text{-}Bu)_4$, $Zr(OCH_2CH(Et)Bu)_4$, $CpZrCl_3$, $Cp_2ZrCl_2$, $Cp_2Zr(OTf)_2$, $(i\text{-}PrO)_2ZrCl_2$, and $(i\text{-}PrO)_3ZrCl$.

Examples of hafnium compounds include those represented by $HfX^3_4$ (where 4 $X^3$'s, independently of each other, represent any of the ligands exemplified above, provided that 4 $X^3$'s may be the same type of ligand or different from each other.). When $X^3$ is an alkoxy group, it may preferably be a linear- or branched-chain alkoxy group having 1 to 10 carbon atoms, more preferably a linear- or branched-chain alkoxy group having 1 to 5 carbon atoms, still more preferably a linear- or branched-chain alkoxy group having 1 to 4 carbon atoms. When $X^3$ is an aryloxy group, it may preferably be an aryloxy group having 1 to 20 carbon atoms, more preferably an aryloxy group having 1 to 15 carbon atoms, still more preferably an aryloxy group having 1 to 10 carbon atoms. These ligands may have one or more substituents. When $X^3$ is a halogen atom, it may preferably be a chlorine atom or a bromine atom. Preferred examples of hafnium compounds include $HfCp_2Cl_2$, $HfCpCl_3$, and $HfCl_4$.

Examples of tantalum compounds include those represented by $TaX^4_5$ (where 5 $X^4$'s, independently of each other, represent any of the ligands exemplified above, provided that 5 $X^4$'s may be the same type of ligand or different from each other.). When $X^4$ is an alkoxy group, it may preferably be a linear- or branched-chain alkoxy group having 1 to 10 carbon atoms, more preferably a linear- or branched-chain alkoxy group having 1 to 5 carbon atoms, still more preferably a linear- or branched-chain alkoxy group having 1 to 4 carbon atoms. When $X^4$ is an aryloxy group, it may preferably be an aryloxy group having 1 to 20 carbon atoms, more preferably an aryloxy group having 1 to 15 carbon atoms, still more preferably an aryloxy group having 1 to 10 carbon atoms. These ligands may have one or more substituents. When $X^4$ is a halogen atom, it may preferably be a chlorine atom or a bromine atom. Preferred examples of tantalum compounds include tantalum alkoxide compounds (e.g., compounds in which $X^4$ is an alkoxy group) such as $Ta(OMe)_5$, $Ta(OEt)_5$, $Ta(OBu)_5$, $Ta(NMe_2)_5$, $Ta(acac)(OEt)_4$, $TaCl_5$, $TaCl_4(THF)$, and $TaBr_5$. Other examples are those in which $X^4$ is an oxygen, such as $Ta_2O_5$.

Examples of niobium compounds include those represented by $NbX^5_5$ (where 5 $X^5$'s, independently of each other, represent any of the ligands exemplified above, provided that 5 $X^5$'s may be the same type of ligand or different from each other.). When $X^5$ is an alkoxy group, it may preferably be a linear- or branched-chain alkoxy group having 1 to 10 carbon atoms, more preferably a linear- or branched-chain alkoxy group having 1 to 5 carbon atoms, still more preferably a linear- or branched-chain alkoxy group having 1 to 4 carbon atoms. When $X^5$ is an aryloxy group, it may preferably be an aryloxy group having 1 to 20 carbon atoms, more preferably an aryloxy group having 1 to 15 carbon atoms, still more preferably an aryloxy group having 1 to 10 carbon atoms. These ligands may have one or more substituents. When $X^5$ is a halogen atom, it may preferably be a chlorine atom or a bromine atom. Preferred examples of niobium compounds include niobium alkoxide compounds (e.g., compounds in which $X^5$ is an alkoxy group) such as $NbCl_4$(THF), $NbCl_5$, $Nb(OMe)_5$, and $Nb(OEt)_5$. Other examples are those in which $X^5$ is an oxygen, such as $Nb_2O_5$.

The Lewis acid catalyst may be loaded on a carrier. There are no particular restrictions on the carrier on which the Lewis acid catalyst is to be loaded, and any known carrier can be used. Also, any known method can be used to load the Lewis acid catalyst on the carrier.

*Base:

In the production method of the fused ring dipeptide compound according to the present invention, a base may be coexisted in the system from the viewpoint of increasing reaction efficiency. The type of base is not restricted, and any base that is known to improve reaction efficiency can be used. Examples of such bases include amines having 1 to 4 linear or branched-chain alkyl groups with 1 to 10 carbons, such as tetrabutylammonium fluoride (TBAF), triethylamine ($Et_3N$), diisopropylamine ($i\text{-}Pr_2NH$), and diisopropylethylamine ($i\text{-}Pr_2EtN$). Any one of these may be used alone, or two or more may be used together in any combination and ratio.

*Other Ingredients:

In the production method of the fused ring dipeptide compound according to the present invention, any other ingredients may coexist in the system in addition to the amino acid represented by formula (R1) and the amino acid ester represented by formula (R2) used as substrates, the first silane compound of formula (S1) and the second silane compound of formula (S2), as well as the Lewis acid catalyst and the base which may be optionally used. Examples of other ingredients may include, although are not limited to, iodine, trimethylsilyl chloride, trimethylsilyl bromide, and trimethylsilyl iodide. Any one of these may be used alone, or two or more may be used together in any combination and ratio.

From the viewpoint of increasing reaction efficiency, the reaction may be carried out in a solvent. Examples of solvents include, although are not limited to, aqueous solvents and organic solvents. Examples of organic solvents may include, although are not limited to: aromatic hydrocarbons such as toluene and xylene; eters such as pentane, petroleum ether, tetrahydrofuran (THF), 1-methyl tetrahydrofuran (1-MeTHF), diisopropyl ether ($i\text{-}Pr_2O$), diethyl ether ($Et_2O$), and cyclopentylmethyl ether (CPME); nitrogen-containing organic solvents acetonitrile (MeCN); chlorine-containing organic solvents such as dichloromethane (DCM); esters such as ethyl acetate (AcOEt); and organic acids such as acetic acids. Any one of these solvents may be used alone, or two or more may be used together in any combination and ratio.

*Reaction Procedure:

The production method of the fused ring dipeptide compound according to the present invention includes: as step (i), contacting one of the substrates, i.e., the amino acid represented by formula (R1), with the first silane compound of formula (S1) and the second silane compound of formula (S2) to cause a reaction; and as step (ii), adding the other substrate, the amino acid ester represented by formula (R2), to the reaction system to cause a further reaction. This reaction procedure leads to the formation of the fused ring dipeptide compound according to the present invention. Although the reaction mechanism has not been cleared, it is presumed that the first silane compound of formula (S1) and the second silane compound of formula (S2) form silyl diimidazole having two nitrogen-containing hetero rings in the system, which then causes a 5-membered ring formation reaction with the non-protected amino acid represented by formula (R1), a coupling reaction with the amino acid ester represented by formula (R2), hydrolysis of the amino acid ester, and another 5-membered ring formation reaction to proceed in succession.

The timing for adding other optionally-used components, such as an Lewis acid catalyst and a base, to the reaction system is not restricted, and any of them can be added at any timing. However, when a Lewis acid catalyst is used, it is preferable to add it to the system at the start of step (ii). When a base is used, it is preferable to add it to the system at the start of step (i). When the reaction is carried out using a solvent, the components may be mixed in the solvent and brought into contact with each other.

*Ratios of the Amounts of the Ingredients Used:

In the production method of the fused ring dipeptide compound according to the present invention, the amount of each component used is not limited, but is preferably as follows.

The amount ratio between the amino acid represented by formula (R1) and the amino acid ester represented by formula (R2) are not restricted, but relative to 1 mol of the amino acid represented by formula (R1), the amino acid ester represented by formula (R2) may be used in an amount within the range of 0.05 mol or more, or 0.1 mol or more, or 0.2 mol or more, or 0.3 mol or more, or 0.4 mol or more, and 10 mol or less, or 5 mol or less, or 4 mol or less, or 3 mol or less, or 2 mol or less. It is preferred to use the amino acid represented by formula (R1) in a larger amount than that of the amino acid ester represented by formula (R2), from the viewpoint of increasing the reaction efficiency. Specifically, relative to 1 mol of the amino acid represented by formula (R1), the amino acid ester represented by formula (R2) may be used in an amount of approximately 0.5 mol. Needless to say, with respect to the target production amount of the fused ring dipeptide compound of formula (A) of the present invention to be manufactured, it is necessary to use at least 1 mol each of the amino acid represented by formula (R1) and the amino acid ester represented by formula (R2) as substrates.

The amounts of the first silane compound of formula (S1) and the second silane compound of formula (S2) used are not restricted, as long as they are used in amounts that can induce the formation reaction of the fused ring dipeptide compound of formula (A) from the amino acid of formula (R1) and the amino acid ester of formula (R2) through implementation of the production method according to the present invention. For example, relative to 1 mol of the amino acid represented by formula (R1), the first silane compound of formula (S1) may be used in an amount within the range of 0.1 mol or more, or 0.2 mol or more, or 0.3 mol or more, or 0.4 mol or more, or 0.5 mol or more, and 20 mol or less, or 15 mol or less, or 10 mol or less, or 8 mol or less, or 6 mol or less, or 4 mol or less, or 2 mol or less. Likewise, relative to 1 mol of the amino acid represented by formula (R1), the second silane compound of formula (S2) may be used in an amount within the range of 0.2 mol or more, or 0.4 mol or more, or 0.6 mol or more, or 0.8 mol or more, or 1.0 mol or more, and 40 mol or less, or 30 mol or less, or 20 mol or less, or 15 mol or less, or 10 mol or less, or 6 mol or less, or 4 mol or less. When two or more first silane compounds of formula (S1) are used, the total amount of the two or more first silane compounds of formula (S1) may satisfy the aforementioned ranges. When two or more second silane compound of formula (S2) are used, the total amount of the two or more second silane compound of formula (S2) may satisfy the aforementioned ranges.

When a base is used, the amount of the base used is not restricted, but relative to 1 mol of the amino acid represented by formula (R1), the base may be used in an amount within the range of 0.2 mol or more, or 0.4 mol or more, or 0.6 mol or more, or 0.8 mol or more, or 1.0 mol or more, and 40 mol or less, or 30 mol or less, or 20 mol or less, or 15 mol or less, or 10 mol or less, or 6 mol or less, or 4 mol or less.

When a Lewis acid catalyst is used, the amount of the Lewis acid catalyst used is not restricted, but relative to 100 mol % of the amino acid represented by formula (R1), the Lewis acid catalyst may be used in an amount within the range of typically 0.1 mol % or more, for example 0.2 mol % or more, or 0.3 mol % or more, and typically 30 mol % or less, for example 20 mol % or less, or 15 mol % or less.

*Reaction Conditions:

The conditions for the amidation reaction in the production method according to the present invention are not limited as long as the reaction proceeds, although examples of the conditions for each reaction step are described below.

First, when the amino acid of formula (R1) as one of the substrates is brought into contact with the first silane compound of formula (S1) and the second silane compound of formula (S2) at step (i), the reaction conditions are not restricted as long as the reaction proceeds, but may be as follows.

The reaction temperature at step (i) is not restricted as long as the reaction proceeds, but may be 0° C. or more, or 10° C. or more, or 20° C. or more, and 100° C. or less, or 80° C. or less, or 60° C. or less.

The reaction pressure at step (i) is also not limited as long as the reaction proceeds, and the reaction may be carried out under reduced, normal, or pressurized pressure, but may typically be carried out under normal pressure.

The reaction atmosphere at step (i) is also not limited as long as the reaction proceeds, but the reaction may be carried out under an atmosphere of inert gas such as argon or nitrogen.

The reaction time of step (i) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

On the other hand, the amino acid ester represented by formula (R2) as the other substrate is added to the reaction system to cause a further reaction at step (ii), the reaction conditions are also not limited as long as the reaction proceeds, but may be as follows.

The reaction temperature at step (ii) is not restricted as long as the reaction proceeds, but may be 0° C. or more, or 10° C. or more, or 20° C. or more, and 100° C. or less, or 80° C. or less, or 60° C. or less.

The reaction pressure at step (ii) is also not limited as long as the reaction proceeds, and the reaction may be carried out under reduced, normal, or pressurized pressure, but may typically be carried out under normal pressure.

The reaction atmosphere at step (ii) is also not limited as long as the reaction proceeds, but the reaction may be carried out under an atmosphere of inert gas such as argon or nitrogen.

The reaction time of step (ii) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

Each of step (i) and step (ii) may be carried out in a sequential manner (batch) or in a continuous manner (flow). Details of specific procedures for implementing a sequential method (batch method) and a continuous method (flow method) are well-known in the art. Step (i) and step (ii) may be performed consecutively in one pod.

*Post-Treatments (e.g., Purification and Recovery):

The fused ring dipeptide compound according to the present invention obtained by the production method mentioned above may be subjected to various post-treatments. For example, the resulting fused ring dipeptide compound according to the present invention can be isolated and purified according to conventional methods such as column chromatography and recrystallization. Also, the resulting fused ring dipeptide compound according to the present invention may be subjected directly, or after isolation or purification, to the polypeptide production method according to the present invention explained below to thereby produce a polypeptide.

V. Production Method of Polypeptide According to Present Invention

The fused ring dipeptide compound according to the present invention can be used in a variety of reactions, but they are particularly suitable for use in the production of polypeptides. Methods for producing a polypeptide using the fused ring dipeptide compound according to the present invention (the polypeptide production methods according to the present invention) include two embodiments (these embodiments may also be referred to as "the first polypeptide production method according to the present invention" and "the second polypeptide production method according to the present invention"). However, polypeptide production methods using the fused ring dipeptide compound according to the present invention are not limited to these two embodiments.

(1) First Polypeptide Production Method:

The first polypeptide production method according to the present invention is a method in which one molecule of the fused ring dipeptide compound of the present invention is used to produce one molecule of the polypeptide compound, and includes causing reactions among a silane-containing fused ring dipeptide compound represented by formula (A), a protected amino acid or protected peptide compound represented by formula (R3), and an amino acid ester or peptide ester compound represented by formula (R4) to produce a polypeptide compound represented by formula (P1).

*Silane-Containing Fused Ring Dipeptide Compound (Substrate Compound):

The first polypeptide production method according to the present invention includes using, as a substrate, the silane-containing fused ring dipeptide compound represented by formula (A) (the fused ring dipeptide compound according to the present invention), the details of which were detailed above.

*Protected Amino Acid/Peptide and Amino Acid/Peptide Ester (Substrate Compounds):

The first polypeptide production method according to the present invention includes using, as substrates, a protected amino acid or protected peptide and an amino acid ester or peptide ester, which are represented by formulae (R3) and (R4), respectively.

[Chem. 20]

(R3)

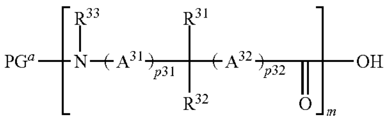

[Chem. 21]

(R4)

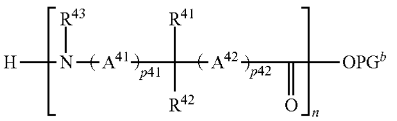

In formulae (R3) and (R4), $R^{31}$, $R^{32}$, $R^{41}$, and $R^{42}$ represent, independently of each other, a hydrogen atom, halogen atom, hydroxyl group, carboxyl group, nitro group, cyano group, or thiol group, or an amino group, monovalent aliphatic hydrocarbon group, monovalent aromatic hydrocarbon group, or monovalent heterocyclic group that may have one or more substituents. The details of the substituents, if any, are described above. Specific examples of the number of substituents are 5, 4, 3, 2, 1, or 0.

In formulae (R3) and (R4), when each of $R^{31}$, $R^{32}$, $R^{41}$, and/or $R^{42}$ is a monovalent aliphatic hydrocarbon group, aromatic hydrocarbon group, or heterocyclic group that may have one or more substituents, a linking group may intervene between the aliphatic hydrocarbon group, aromatic hydrocarbon group, or heterocyclic group and the carbon atom to which it binds. The linking group may be, independently of each other, selected from, although is not limited to, the structures listed below (where, in the chemical formulae below, A represents, independently of each other, a monovalent aliphatic hydrocarbon group, aromatic hydrocarbon group, or heterocyclic group that may have one or more substituents. When two A's are present in the same group, they may be identical to each other or different from each other.).

[Chem. 22]

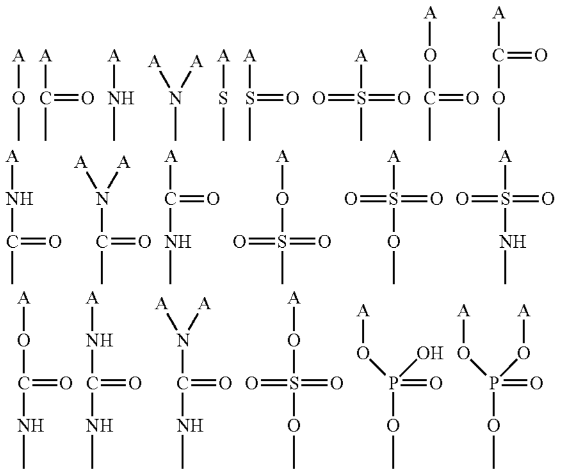

-continued

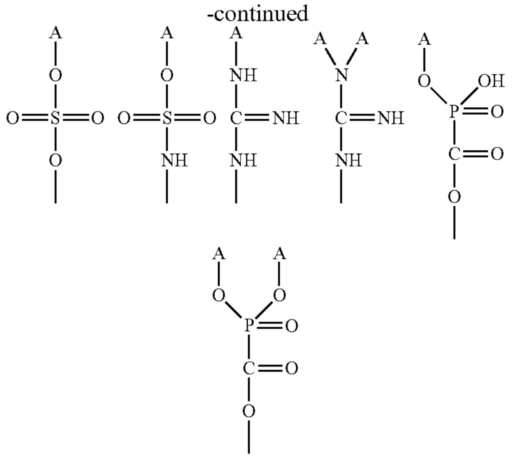

In formulae (R3) and (R4), when each of $R^{31}$, $R^{32}$, $R^{41}$, and/or $R^{42}$ is an aliphatic hydrocarbon group, the number of carbon atoms in the aliphatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aliphatic hydrocarbon group, but may be 1 or more in the case of alkyl groups, 2 or more in the case of alkenyl groups or alkynyl groups, 3 or more, for example 4 or more, or 5 or more in the case of cycloalkyl groups. Specific examples of the number of atoms include 1, 2, 3, 4, 5, 6, 7, 8, 9, 10, 11, 12, 13, 14, 15, 16, 17, 18, 19, or 20.

In formulae (R3) and (R4), when each of $R^{31}$, $R^{32}$, $R^{41}$, and/or $R^{42}$ is an aromatic hydrocarbon group, the number of carbon atoms in the aromatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aromatic hydrocarbon group, but may be typically 4 or more, for example 5 or more, or 6 or more. Specific examples of the number of atoms include 4, 5, 6, 7, 8, 9, 10, 11, 12, 13, 14, 15, 16, 17, 18, 19, or 20.

In formulae (R3) and (R4), when each of $R^{31}$, $R^{32}$, $R^{41}$, and/or $R^{42}$ is a heterocyclic group, the total number of carbon atoms and hetero atoms in the heterocyclic group (when it has one or more substituents, including the number of atoms in the substituents) may be, although is not particularly limited to, typically 20 or less, 15 or less, 10 or less, 8 or less, or 6 or less. The lower limit thereof depends on the type of the heterocyclic structure, but may be typically 3 or more, for example 4 or more, or 5 or more. Specific examples of the number of atoms include 3, 4, 5, 6, 7, 8, 9, 10, 11, 12, 13, 14, 15, 16, 17, 18, 19, or 20.

Each of $R^{31}$, $R^{32}$, $R^{41}$, and $R^{42}$ in formulae (R3) and (R4) may preferably be, independently of each other, a hydrogen atom, hydroxyl group, thiol group, carboxyl group, nitro group, cyano group, or halogen atom, or, that may have one or more substituents, amino group, alkyl group, alkenyl group, cycloalkyl group, alkoxy group, aryl group, aryloxy group, acyl group, heterocyclic group, or heterocyclic oxy group.

Specific examples of $R^{31}$, $R^{32}$, $R^{41}$, and $R^{42}$ in formulae (R3) and (R4) may include, although are not limited to, the following.

*Hydrogen atom, hydroxyl group, thiol group, carboxyl group, nitro group, and cyano group;

*Halogen atoms such as fluorine atom, chlorine atom, bromine atom, and iodine atom;

*Alkyl groups such as methyl group, ethyl group, propyl group, isopropyl group, n-butyl group, isobutyl group, tert-butyl group, sec-butyl group, pentyl group, isopentyl group, neopentyl group, hexyl group, heptyl group, octyl group, decyl group, and nonyl group;

*Alkenyl groups such as ethenyl group, propenyl group, allyl group, butenyl group, pentenyl group, hexenyl group, heptenyl group, and octenyl group;

*Alkynyl groups such as propargyl group;

*Cycloalkyl groups such as cyclopropyl group, cyclobutyl group, cyclopentyl group, cyclohexyl group, cycloheptyl group, bicyclooctyl group, and spirooctyl group;

*Alkoxy groups such as methoxy group, ethoxy group, propoxy group, butoxy group, sec-butoxy group, and tert-butoxy group;

*Aryl groups such as phenyl group, benzyl group, tolyl group, naphthyl group, and anthracenyl group;

*Aryloxy groups such as phenyloxy group, benzyloxy group, and naphthyloxy group;

*Acyl groups such as acetyl group, propionyl group, benzoyl group, p-methoxybenzoyl group, and cinnamoyl group;

*Unsubstituted amino group and substitution amino groups such as dimethylamino group, benzylamino group, and triphenylmethylamino group;

*Heterocyclic groups such as furanyl group, thiophenyl group, pyranyl group, pyrrolinyl group, pyrrolyl group, 2,3-dihydro-1H-pyrrolyl group, piperidinyl group, piperazinyl group, homopiperazinyl group, morpholino group, thiomorpholino group, 1,2,4,6-tetrahydro pyridyl group, hexahydro pyrimidyl group, hexahydro pyridazyl group, 1,2,4,6-tetrahydro pyridyl group, 1,2,4,6-tetrahydro pyridazyl group, 3,4-dihydropyridyl group, imidazolyl group, 4,5-dihydro-1H-imidazolyl group, 2,3-dihydro-1H-imidazolyl group, pyrazolyl group, 4,5-dihydro-1H-pyrazolyl group, 2,3-dihydro-1H-pyrazolyl group, oxazolyl group, 4,5-dihydro-1,3-oxazolyl group, 2,3-dihydro-1,3-oxazolyl group, 2,5-dihydro-1,3-oxazolyl group, thiazolyl group, 4,5-dihydro-1,3-thiazolyl group, 2,3-dihydro-1,3-thiazolyl group, 2,5-dihydro-1,3-thiazolyl group, carbazolyl group; and

*Heterocyclic oxy groups such as furanyl oxy group, pyrrolyl oxy group, indolyl oxy group, and quinolyl oxy group.

In formulae (R3) and (R4), $R^{33}$ and $R^{43}$ represent, independently of each other, a hydrogen atom, carboxyl group, or hydroxyl group, or, that may have one or more substituents, monovalent hydrocarbon group or heterocyclic group. The details of the substituents, if any, are described above. Specific examples of the number of substituents are 5, 4, 3, 2, 1, or 0.

In formulae (R3) and (R4), when each of $R^{33}$ and/or $R^{43}$ is a monovalent aliphatic hydrocarbon group, aromatic hydrocarbon group, or heterocyclic group that may have one or more substituents, a linking group may intervene between the aliphatic hydrocarbon group, aromatic hydrocarbon group, or heterocyclic group and the nitrogen atom to which it binds. The linking group may be, independently of each other, selected from, although is not limited to, the structures listed below (where, in the chemical formulae below, A represents, independently of each other, a monovalent aliphatic hydrocarbon group, aromatic hydrocarbon group, or heterocyclic group that may have one or more substituents. When two A's are present in the same group, they may be identical to each other or different from each other.).

[Chem. 23]

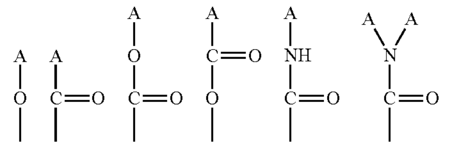

In formulae (R3) and (R4), when each of $R^{33}$ and/or $R^{43}$ is an aliphatic hydrocarbon group, the number of carbon atoms in the aliphatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aliphatic hydrocarbon group, but may be 1 or more in the case of alkyl groups, 2 or more in the case of alkenyl groups or alkynyl groups, 3 or more, for example 4 or more, or 5 or more in the case of cycloalkyl groups. Specific examples of the number of atoms include 1, 2, 3, 4, 5, 6, 7, 8, 9, 10, 11, 12, 13, 14, 15, 16, 17, 18, 19, or 20.

In formulae (R3) and (R4), when each of $R^{33}$ and/or $R^{43}$ is an aromatic hydrocarbon group, the number of carbon atoms in the aromatic hydrocarbon group (when it has one or more substituents, including the number of atoms in the substituents) may be, although is not particularly limited to, typically 20 or less, 15 or less, 10 or less, 8 or less, or 6 or less. The lower limit thereof depends on the type of the aromatic hydrocarbon group, but may be typically 4 or more, for example 5 or more, or 6 or more. Specific examples of the number of atoms include 4, 5, 6, 7, 8, 9, 10, 11, 12, 13, 14, 15, 16, 17, 18, 19, or 20.

In formulae (R3) and (R4), when each of $R^{33}$ and/or $R^{43}$ is a heterocyclic group, the total number of carbon atoms and hetero atoms in the heterocyclic group (when it has one or more substituents, including the number of atoms in the substituents) may be, although is not particularly limited to, typically 20 or less, 15 or less, 10 or less, 8 or less, or 6 or less. The lower limit thereof depends on the type of the heterocyclic structure, but may be typically 3 or more, for example 4 or more, or 5 or more. Specific examples of the number of atoms include 3, 4, 5, 6, 7, 8, 9, 10, 11, 12, 13, 14, 15, 16, 17, 18, 19, or 20.

Each of $R^{33}$ and/or $R^{43}$ in formulae (R3) and (R4) may preferably be, independently of each other, a hydrogen atom, hydroxyl group, or carboxyl group, or, that may have one or more substituents, alkyl group, alkenyl group, cycloalkyl group, alkoxy group, aryl group, aryloxy group, acyl group, heterocyclic group, or heterocyclic oxy group.

Specific examples of $R^{33}$ and/or $R^{43}$ in formulae (R3) and (R4) may include, although are not limited to, the following.

*Hydrogen atom, hydroxyl group, thiol group, carboxyl group, nitro group, and cyano group;

*Halogen atoms such as fluorine atom, chlorine atom, bromine atom, and iodine atom;

*Alkyl groups such as methyl group, ethyl group, propyl group, isopropyl group, n-butyl group, isobutyl group, tert-butyl group, sec-butyl group, pentyl group, isopentyl group, neopentyl group, hexyl group, heptyl group, octyl group, decyl group, and nonyl group;

*Alkenyl groups such as ethenyl group, propenyl group, allyl group, butenyl group, pentenyl group, hexenyl group, heptenyl group, and octenyl group;
*Alkynyl groups such as propargyl group;
*Cycloalkyl groups such as cyclopropyl group, cyclobutyl group, cyclopentyl group, cyclohexyl group, cycloheptyl group, bicyclooctyl group, and spirooctyl group;
*Alkoxy groups such as methoxy group, ethoxy group, propoxy group, butoxy group, sec-butoxy group, and tert-butoxy group;
*Aryl groups such as phenyl group, benzyl group, tolyl group, naphthyl group, and anthracenyl group;
*Aryloxy groups such as phenyloxy group, benzyloxy group, and naphthyloxy group;
*Acyl groups such as acetyl group, propionyl group, benzoyl group, p-methoxybenzoyl group, and cinnamoyl group;
*Unsubstituted amino group and substitution amino groups such as dimethyl amino group, benzyl amino group, and triphenylmethyl amino group;
*Heterocyclic groups such as furanyl group, thiophenyl group, pyranyl group, pyrrolinyl group, pyrrolyl group, 2,3-dihydro-1H-pyrrolyl group, piperidinyl group, piperazinyl group, homopiperazinyl group, morpholino group, thiomorpholino group, 1,2,4,6-tetrahydro pyridyl group, hexahydro pyrimidyl group, hexahydro pyridazyl group, 1,2,4,6-tetrahydro pyridyl group, 1,2,4,6-tetrahydro pyridazyl group, 3,4-dihydropyridyl group, imidazolyl group, 4,5-dihydro-1H-imidazolyl group, 2,3-dihydro-1H-imidazolyl group, pyrazolyl group, 4,5-dihydro-1H-pyrazolyl group, 2,3-dihydro-1H-pyrazolyl group, oxazolyl group, 4,5-dihydro-1,3-oxazolyl group, 2,3-dihydro-1,3-oxazolyl group, 2,5-dihydro-1,3-oxazolyl group, thiazolyl group, 4,5-dihydro-1,3-thiazolyl group, 2,3-dihydro-1,3-thiazolyl group, 2,5-dihydro-1,3-thiazolyl group, carbazolyl group; and
*Heterocyclic oxy groups such as furanyl oxy group, pyrrolyl oxy group, indolyl oxy group, and quinolyl oxy group.

Alternatively, in formula (R3), $R^{31}$ and $R^{33}$ may be bound to each other to form, together with the carbon atom to which $R^{31}$ binds and the nitrogen atom to which $R^{33}$ binds, a hetero ring that may have one or more substituents. Likewise, in formula (R4), $R^{41}$ and $R^{43}$ may be bound to each other to form, together with the carbon atom to which $R^{41}$ binds and the nitrogen atom to which $R^{43}$ binds, a hetero ring that may have one or more substituents. The details of the substituents, if any, are described above. Specific examples of the number of substituents are 5, 4, 3, 2, 1, or 0.

The total number of carbon atoms and hetero atoms in the heterocyclic group (when it has one or more substituents, including the number of atoms in the substituents) may be typically 20 or less, 15 or less, 10 or less, 8 or less, or 6 or less. The lower limit thereof depends on the type of the heterocyclic structure, but may be typically 3 or more, for example 4 or more, or 5 or more. Specific examples of the number of atoms include 3, 4, 5, 6, 7, 8, 9, 10, 11, 12, 13, 14, 15, 16, 17, 18, 19, or 20.

Examples of such hetero rings include, but are not limited to, pyrrolinyl group, pyrrolyl group, 2,3-dihydro-1H-pyrrolyl group, piperidinyl group, piperazinyl group, homopiperazinyl group, morpholino group, thiomorpholino group, 1,2,4,6-tetrahydro pyridyl group, hexahydro pyrimidyl group, hexahydro pyridazyl group, 1,2,4,6-tetrahydro pyridyl group, 1,2,4,6-tetrahydro pyridazyl group, 3,4-dihydropyridyl group, imidazolyl group, 4,5-dihydro-1H-imidazolyl group, 2,3-dihydro-1H-imidazolyl group, pyrazolyl group, 4,5-dihydro-1H-pyrazolyl group, 2,3-dihydro-1H-pyrazolyl group, oxazolyl group, 4,5-dihydro-1,3-oxazolyl group, 2,3-dihydro-1,3-oxazolyl group, 2,5-dihydro-1,3-oxazolyl group, thiazolyl group, 4,5-dihydro-1,3-thiazolyl group, 2,3-dihydro-1,3-thiazolyl group, and 2,5-dihydro-1,3-thiazolyl group.

In formulae (R3) and (R4), $A^{31}$, $A^{32}$, $A^{41}$, and $A^{42}$ represent, independently of each other, a divalent aliphatic hydrocarbon group containing 1 to 3 carbon atoms that may have one or more substituents. Specific Examples include, although are not limited to, methylene group, ethylene group, propylene group, and isopropylene group, as well as groups derived from these groups via substitution with one or more substituents mentioned above. Specific examples of the number of substituents are 3, 2, 1, or 0.

In formulae (R3) and (R4), p31, p32, p41, and p42 represent, independently of each other, 0 or Is.

In formulae (R3) and (R4), m and n represent, independently of each other, an integer being equal to or more than 1, and corresponds to the number of the structure units parenthesized with [ ]. In other words, m represents the number of amino acid units parenthesized with [ ] in formula (R3). When m is 1, the compound of formula (R3) is a protected amino acid, while when m is 2 or more, the compound of formula (R3) is a protected peptide. Likewise, n represents the number of amino acid units parenthesized with [ ] in formula (R4). When n is 1, the compound of formula (R4) is a protected amino acid, while when n is 2 or more, the compound of formula (R4) is a protected peptide. The upper limit of each of m and n is not particularly limited so long as the amidation step proceeds, but may preferably be, for example, 100 or less, 80 or less, 60 or less, 50 or less, 40 or less, 30 or less, 20 or less, 15 or less, 12 or less, or 10 or less. Examples of each of m and n, independently of each other, include 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, and 100.

In formula (R3), $PG^{a}$ represents a protecting group for an amino group. $PG^{a}$ is not restricted as long as the amino group concerned can be protected so as not to react during a given reaction, and can be deprotected and converted to an amino group after the reaction. The details for the protecting group for an amino group will be explained later.

In formula (R4), $PG^{b}$ represents a protecting group for a carboxyl group. $PG^{b}$ is not restricted as long as the carboxyl group concerned can be protected so as not to react during a given reaction, and can be deprotected and converted to a carboxyl group after the reaction. The details for the protecting group for a carboxyl group were explained above.

*Protecting Group for an Amino Group:

Various protecting groups for an amino group (carboxyl-protecting groups) $PG^{b}$ to be used in each of the production methods according to the present invention (i.e., the production method of the fused ring dipeptide compound according to the present invention as well as the first and second polypeptide production methods according to the present invention) are known to the art. Examples include a monovalent aliphatic hydrocarbon group or aromatic hydrocarbon group that may have one or more substituents or a monovalent heterocyclic group that may have one or more substituents. Preferred among them include a monovalent aliphatic hydrocarbon group or aromatic hydrocarbon group that may have one or more substituents. However, the aliphatic hydrocarbon group, aromatic hydrocarbon group, or heterocyclic group and the nitrogen atom of the amino group it protects (the nitrogen atom to which $PG^a$ binds in formula (R3)). The linking group may be, independently of each other, selected from, although is not limited to, the following groups (where, in the chemical formulae below, A represents, independently of each other, a monovalent aliphatic hydrocarbon group, aromatic hydrocarbon group, or heterocyclic group that may have one or more substituents. When two A's are present in the same group, they may be identical to each other or different from each other.).

[Chem. 24]

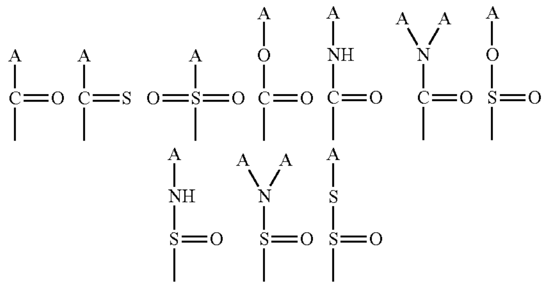

The number of carbons in the amino-protecting group $PG^a$ may be typically 1 or more, or 3 or more, and typically 20 or less, or 15 or less.

Among them, the amino-protecting group $PG^a$ may preferably be one or more selected from the group consisting of monovalent aliphatic hydrocarbon or aromatic hydrocarbon groups, acyl groups, hydrocarbon oxycarbonyl groups, hydrocarbon sulfonyl groups and amides that may have one or more substituents.

Specific examples of the amino-protective group $PG^1$ are listed below. Incidentally, an amino-protective group may be referred to either by the name of the functional group excluding the nitrogen atom of the amino group to which it binds or by the name of the group including the nitrogen atom to which it binds. The following list includes either or both of these names for each protective group.

Examples of unsubstituted or substituted hydrocarbon groups includes: alkyl groups such as methyl group, ethyl group, and propyl group; alkenyl groups such as ethenyl group, propenyl group, and allyl group; alkynyl groups such as propargyl group; cycloalkyl groups such as cyclopropyl group, cyclobutyl group, cyclopentyl group, and cyclohexyl group; aryl groups such as phenyl group, benzyl group, p-methoxybenzyl group, tolyl group, and triphenylmethyl group (Troc group); and substituted hydrocarbon groups such as cyanomethyl group. The number of carbon atoms may typically be 1 or more, or 3 or more, and typically 20 or less, or 15 or less.

Examples of unsubstituted or substituted acyl groups includes: benzoyl group (Bz), o-methoxybenzoyl group, 2,6-dimethoxy benzoyl group, p-methoxybenzoyl group (PMPCO), cinnamoyl group, and phthaloyl group (Phth).

Examples of unsubstituted or substituted hydrocarbon oxycarbonyl groups includes: tert-butoxycarbonyl group (Boc), benzyloxycarbonyl group (Cbz or Z), methoxycarbonyl group, ethoxycarbonyl group, 2-(trimethylsilyl) ethoxycarbonyl group, 2-phenyl ethoxycarbonyl group, 1-(1-adamanthyl)-1-methylethoxycarbonyl group, 1-(3,5-di-t-butylphenyl)-1-methylethoxycarbonyl group, vinyloxycarbonyl group, allyloxycarbonyl group (Alloc), N-hydroxypiperidinyloxycarbonyl group, p-methoxybenzyloxycarbonyl group, p-nitrobenzyloxycarbonyl group, 2-(1,3-dithianyl) methoxycarbonyl, m-nitrophenoxycarbonyl group, 3,5-dimethoxybenzyloxycarbonyl group, o-nitrobenzyloxycarbonyl group, 2,2,2-trichloroethoxycarbonyl group (Troc), and 9-fluorenylmethyloxycarbonyl group (Fmoc).

Examples of unsubstituted or substituted hydrocarbon sulfonyl groups includes: methane sulfonyl group (Ms), toluenesulfonyl group (Ts), and 2- or 4-nitro benzene sulfonyl (Ns) group.

Examples of unsubstituted or substituted amide groups includes: acetamide, o-(benzoyloxymethyl)benzamide, 2-[(t-butyl-diphenyl-siloxy)methyl]benzamide, 2-toluenesulfonamide, 4-toluenesulfonamide, 2-nitro benzene sulfonamide, 4-nitro benzene sulfonamide, tert-butylsulfinyl amide, 4-toluenesulfonamide, 2-(trimethylsilyl)ethane sulfonamide, and benzyl sulfonamide.

In terms of deprotection methods, the protective group $PG^a$ may be deprotected by, e.g., at least one of the following methods: deprotection by hydrogenation, deprotection by weak acid, deprotection by fluorine ion, deprotection by one-electron oxidizing agent, deprotection by hydrazine, and deprotection by oxygen.

Preferred examples of the amino protective group $PG^a$ include mesyl group (Ms), tert-butoxycarbonyl group (Boc), benzyl group (Bn or Bzl), benzyloxycarbonyl group (Cbz), benzoyl group (Bz), p-methoxybenzyl group (PMB), 2,2,2-trichloroethoxycarbonyl group (Troc), allyloxycarbonyl group (Alloc), 2,4-dinitrophenyl group (2,4-DNP), phthaloyl group (Phth), p-methoxybenzoyl group (PMPCO), cinnamoyl group, toluenesulfonyl group (Ts), 2- or 4-nitrobenzenesulfonyl group (Ns), cyanomethyl group, and 9-fluorenylmethyloxycarbonyl group (Fmoc). These protective groups are preferred because, as mentioned above, they can easily protect the amino group and can be removed under relatively mild conditions.

More preferable examples of the amino protective group $PG^a$ include mesyl group (Ms), tert-butoxycarbonyl group (Boc), benzyloxycarbonyl group (Cbz), benzyl group (Bn), p-methoxybenzyl group (PMB), 2,2,2-trichloroethoxycarbonyl group (Troc), allyloxycarbonyl group (Alloc), p-methoxybenzoyl group (PMPCO), benzoyl group (Bz), cyanomethyl group, cinnamoyl group, 2- or 4-nitrobenzenesulfonyl group (Ns), toluenesulfonyl group (Ts), phthaloyl group (Phth), 2,4-dinitrophenyl group (2,4-DNP), and 9-fluorenylmethyloxycarbonyl group (Fmoc).

Even more preferable examples of the amino protective group $PG^a$ include mesyl group (Ms), tert-butoxycarbonyl group (Boc), benzyloxycarbonyl group (Cbz), benzyl group (Bn), p-methoxybenzyl group (PMB), 2,2,2-trichloroethoxycarbonyl group (Troc), allyloxycarbonyl group (Alloc), p-methoxybenzoyl group (PMPCO), benzoyl group (Bz), cyanomethyl group, and cinnamoyl group.

In step (i) and/or (ii) above, the reaction system may contain a condensing agent and/or an anti-racemization agent.

The method may also include the step of deprotecting the amino-protecting group $PG^a$ and/or carboxyl-protecting group $PG^b$ of the polypeptide compound of formula (P1).

*Condensing Agent and Anti-Racemization Agent:

In order to improve the reaction efficiency to form the peptide, the first peptide production method of the present invention may involve the use of a condensing agent coexisting in the system. The type of condensing agent is not restricted, and any known condensing agent that is known to improve condensation reaction efficiency can be used. Examples of condensing agents include the following. Any one of these may be used alone, or two or more may be used together in any combination and ratio.

*Carbodiimide condensing agents: 1-[3-(dimethylamino) propyl]-3-ethyl carbodiimide (wsc, edc), hydrochloric acid 1-ethyl-3-(3-dimethylaminopropyl)carbodiimide (wscHCl, edcHCl), N,N'-dicyclohexyl carbodiimide (DCC), and N,N'-diisopropyl carbodiimide (DIC).

*Phosphonium condensing agents: 1H-benzotriazole-1-yloxytris(dimethylamino) phosphonium hexafluorophosphate (BOP), 1H-benzotriazol-1-yloxytripyrrolidino phosphonium hexafluorophosphate (PyBOP), (7-azabenzotriazole-1-yloxy)tripyrrolidino phosphonium hexafluorophosphate (PyAOP), chlorotripyrrolidino phosphonium hexafluorophosphate (PyCloP), bromotris(dimethylamino)phosphonium hexafluorophosphate (Brop), and 3-(diethoxyphosphoryloxy)-1,2,3-benzotriazin-4(3H)-one (DEPBT).

*Imidazole condensing agents: N,N'-carbonyldiimidazole (CDI) and 1,1'-carbonyldi(1,2,4-triazole) (CDT).

*Uronium condensing agents: O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), O—(N-succinimidyl)-N,N,N',N'-tetramethyluronium tetrafluoroborate (TSTU).

*Triazine condensing agents: 4-(4,6-dimethoxy-1,3,5-triazin-2-yl)-4-methylmorpholinium chloride, n hydrate (DMT-MM).

When a condensing agent is used, it may be combined with an anti-racemization agent from the viewpoint of preventing racemization during the peptide formation reaction. The type of anti-racemization agent is not limited, and any anti-racemization agents known to prevent racemization during the condensation reaction can be used. Examples of anti-racemization agents include 1-hydroxybenzotriazole (HOBt), 1-hydroxy-7-azabenzo triazole (HOAt), N-hydroxysuccinimide (HOSu), and N,N'-disuccinimidyl carbonate (DSC). Any one of these may be used alone, or two or more may be used together in any combination and ratio.

*Base:

In the first peptide production method of the present invention, a base may be coexisted in the system from the viewpoint of increasing reaction efficiency. The type of base is not restricted, and any base that is known to improve reaction efficiency can be used. Examples of such bases include amines having 1 to 4 linear or branched-chain alkyl groups with 1 to 10 carbons, such as tetrabutylammonium fluoride (TBAF), triethylamine ($Et_3N$), diisopropylamine ($i\text{-}Pr_2NH$), and diisopropylethylamine ($i\text{-}Pr_2EtN$), as well as inorganic bases such as cesium fluoride. Any one of these may be used alone, or two or more may be used together in any combination and ratio.

*Other Ingredients:

In the first peptide production method of the present invention, in addition to the silane-containing fused ring dipeptide compound represented by formula (A), the protected amino acid or protected peptide represented by formula (R3), and the amino acid ester or peptide ester represented by formula (R4) as substrates, as well as the base, the condensing agent, and the anti-racemization agent as optional components, any other ingredients may coexist in the system. Examples of other ingredients may include, although are not limited to, conventional catalysts that can be used for amidation reaction, as well as silane compounds and phosphorus compounds. Any one of these may be used alone, or two or more may be used together in any combination and ratio.

Examples of catalysts include: various Lewis acid catalysts explained for the production method of the fused ring dipeptide compound according to the present invention, such as titanium compounds, zirconium compounds, hafnium compounds, tantalum compounds, and niobium compounds; methylaluminum bis(4-bromo-2,6-di-tert-butylphenoxyde (MABR), trimethylsilyl trifluoromethanesulfonate (TMS-OTf), and methylaluminum bis(2,6-di-tert-butylphenoxyde (MAD). Any one of these may be used alone, or two or more may be used together in any combination and ratio.

Examples of silane compounds include: various tris{halo-(preferably fluorine-)substituted alkyl}silanes such as $HSi(OCH(CF_3)_2)_3$, $HSi(OCH_2CF_3)_3$, $HSi(OCH_2CF_2CF_2H)_3$, $HSi(OCH_2CF_2CF_2CF_2CF_2H)_3$; as well as trimethylsilyl trifluoromethanesulfonate(TMS-OTf), 1-(trimethylsilyl)imidazole (TMSIM), dimethyl ethylsilyl imidazole (DMESI), dimethyl isopropylsilyl imidazole (DMIPSI), 1-(tert-butyl dimethylsilyl)imidazole (TBSIM), 1-(trimethylsilyl)triazole, 1-(tert-butyl dimethylsilyl)triazole, dimethylsilyl imidazole, dimethylsilyl (2-methyl)imidazole, trimethyl bromosilane (TMBS), trimethyl chlorosilane (TMCS), N-methyl-Ntrimethylsilyl trifluoroacetamide (MSTFA), N,O-bis (trimethylsilyl)trifluoroacetamide (BSTFA), N,O-bis (trimethylsilyl)acetamide (BSA), N-(trimethylsilyl) dimethyl amine (TMSDMA), N-(tert-butyl dimethylsilyl)-N-methyl trifluoroacetamide (MTBSTFA), and hexamethyldisilazane (HMDS). Any one of these may be used alone, or two or more may be used together in any combination and ratio.

Examples of phosphorus compounds include: phosphine compounds such as trimethyl phosphine, triethyl phosphine, tripropyl phosphine, trimethyloxyphosphine, triethyloxyphosphine, tripropyloxyphosphine, triphenyl phosphine, trinaphthyl phosphine, triphenyloxyphosphine, tris(4-methylphenyl)phosphine, tris(4-methoxy phenyl)phosphine, tris (4-fluorophenyl)phosphine, tris(4-methylphenyloxy) phosphine, tris(4-methoxy phenyloxy)phosphine, and tris(4-fluorophenyloxy)phosphine; phosphate compounds such as trimethyl phosphate, triethyl phosphate, tripropyl phosphate, trimethyloxyphosphate, triethyloxyphosphate, tripropyloxyphosphate, triphenyl phosphate, trinaphthyl phosphate, triphenyloxyphosphate, tris(4-methylphenyl)phosphate, tris(4-methoxy phenyl)phosphate, tris(4-fluorophenyl)phosphate, tris(4-methylphenyloxy)phosphate, tris(4-methoxy phenyloxy)phosphate, and tris(4-fluorophenyloxy)phosphate; multivalent phosphine compounds or multivalent phosphate compounds such as 2,2'-bis(diphenylphosphino)-1,1'-binaphthyl (BINAP) and 5,5'-bis(diphenylphosphino)-4,4'-bi-1,3-benzodioxole (SEGPHOS). Any one of these may be used alone, or two or more may be used together in any combination and ratio.

From the viewpoint of increasing reaction efficiency, the reaction may be carried out in a solvent. Examples of solvents include, although are not limited to, aqueous solvents and organic solvents. Examples of organic solvents may include, although are not limited to: aromatic hydrocarbons such as toluene and xylene; eters such as pentane, petroleum ether, tetrahydrofuran (THF), 1-methyl tetrahydrofuran (1-MeTHF), diisopropyl ether ($i\text{-}Pr_2O$), diethyl ether ($Et_2O$), and cyclopentylmethyl ether (CPME); nitrogen-containing organic solvents acetonitrile (MeCN); chlorine-containing organic solvents such as dichloromethane (DCM); esters such as ethyl acetate (AcOEt); and organic acids such as acetic acids. Any one of these solvents may be used alone, or two or more may be used together in any combination and ratio.

*Reaction Procedure:

In the first peptide production method of the present invention, the fused ring dipeptide compound of formula (A), the protected amino acid or protected peptide compound of formula (R3), and the amino acid ester or peptide ester represented by formula (R4) are reacted. In this reaction, the ring of the amino acid residue on the left side of the fused ring dipeptide compound of formula (A) is opened and linked to the protected amino acid or peptide of formula (R3) at its N-terminus, while the ring of the amino acid residue on the right side of the fused ring dipeptide compound of formula (A) is opened and linked to the protective amino acid or peptide of formula (R4) at its C-terminus, thus forming the polypeptide compound of formula (P1).

In the first peptide production method of the present invention, the order of mixing each substrate compound is not limited as long as the above reaction occurs. Examples include, although are not limited to, the following two embodiments.

According to the first embodiment, as step (i), the silane-containing fused ring dipeptide compound represented by formula (A) is reacted with the protected amino acid or protected peptide represented by formula (R3), and then as step (ii), the amino acid ester or peptide ester represented by formula (R4) is added to the reaction system to cause a further reaction. In this embodiment, at step (i), the ring in the amino acid residue on the left side of the fused ring dipeptide compound of formula (A) is opened, and its N-terminal is linked to the protected amino acid or protected peptide represented by formula (R3). Then, at step (ii), the ring in the amino acid residue on the right side of the fused ring dipeptide compound of formula (A) is opened, and its C-terminal is linked to the protected amino acid or protected peptide of formula (R4), whereby the polypeptide compound of formula (P1) is formed.

According to the second embodiment, as step (i), the silane-containing fused ring dipeptide compound represented by formula (A) is reacted with the amino acid ester or peptide ester represented by formula (R4), and then as step (ii), the protected amino acid or protected peptide represented by formula (R3) is added to the reaction system to cause a further reaction. In this embodiment, at step (i), the ring in the amino acid residue on the right side of the fused ring dipeptide compound of formula (A) is opened, and its C-terminal is linked to the protected amino acid or protected peptide of formula (R4). And then, at step (ii), the ring in the amino acid residue on the left side of the fused ring dipeptide compound of formula (A) is opened, and its N-terminal is linked to the protected amino acid or protected peptide represented by formula (R3), whereby the polypeptide compound of formula (P1) is formed.

The timing for adding other optional components, such as the condensing agent and the base, to the reaction system is not restricted, and any of them can be added at any time. However, when the condensing agent and/or base is used, it may preferably be added to the system at the start of step (i) and/or step (ii) in both the first and second embodiments. when the anti-racemization agent is used in addition to the condensing agent, it may preferably be added to the system together with the condensing agent. When the reaction is carried out using a solvent, the other components may be mixed in the solvent and brought into contact with each other.

*Ratios of the Amounts of the Ingredients Used:

In the first peptide production method of the present invention, the amount of each component used is not limited, but may preferably be as follows.

The amount ratio of the fused ring dipeptide compound of formula (A) to the protected amino acid or protected peptide represented by formula (R3) is not restricted, but relative to 1 mol of the fused ring dipeptide compound of formula (A), the protected amino acid or protected peptide represented by formula (R3) may be added in an amount of within the range of 0.1 mol or more, or 0.2 mol or more, or 0.3 mol or more, or 0.4 mol or more, or 0.5 mol or more, and 20 mol or less, or 15 mol or less, or 10 mol or less, or 8 mol or less, or 6 mol or less, or 4 mol or less, or 2 mol or less.

The amount ratio of the fused ring dipeptide compound of formula (A) to the amino acid ester or peptide ester represented by formula (R4) is not restricted, but relative to 1 mol of the fused ring dipeptide compound of formula (A), the amino acid ester or peptide ester represented by formula (R4) may be added in an amount of within the range of 0.1 mol or more, or 0.2 mol or more, or 0.3 mol or more, or 0.4 mol or more, or 0.5 mol or more, and 20 mol or less, or 15 mol or less, or 10 mol or less, or 8 mol or less, or 6 mol or less, or 4 mol or less, or 2 mol or less.

Needless to say, with respect to the target production amount of the polypeptide compound of formula (P1) to be manufactured, it is necessary to use at least 1 mol each of the fused ring dipeptide compound of formula (A), the protected amino acid or protected peptide represented by formula (R3), and the amino acid ester or peptide ester represented by formula (R4) as substrates.

When the base is used, its amount used is not restricted, but relative to 1 mol of the fused ring dipeptide compound of formula (A), the base may be used in an amount of within the range of 0.2 mol or more, or 0.4 mol or more, or 0.6 mol or more, or 0.8 mol or more, or 1.0 mol or more, and 40 mol or less, or 30 mol or less, or 20 mol or less, or 15 mol or less, or 10 mol or less, or 6 mol or less, or 4 mol or less. When the base is added in a plurality of steps, it is preferable to add an amount of the base within the above range in each step.

When the condensing agent is used, its amount used is not restricted, but relative to 1 mol of the fused ring dipeptide compound of formula (A), the condensing agent may be used in an amount of within the range of 0.2 mol or more, or 0.4 mol or more, or 0.6 mol or more, or 0.8 mol or more, or 1.0 mol or more, and 40 mol or less, or 30 mol or less, or 20 mol or less, or 15 mol or less, or 10 mol or less, or 6 mol or less, or 4 mol or less. When the condensing agent is added in a plurality of steps, it is preferable to add an amount of the condensing agent within the above range in each step.

When the anti-racemization agent is used in addition to the condensing agent, its amount used is not restricted, but relative to 1 mol of the fused ring dipeptide compound of formula (A), the anti-racemization agent may be used in an amount of within the range of 0.2 mol or more, or 0.4 mol or more, or 0.6 mol or more, or 0.8 mol or more, or 1.0 mol or more, and 40 mol or less, or 30 mol or less, or 20 mol or less, or 15 mol or less, or 10 mol or less, or 6 mol or less, or 4 mol or less. When the anti-racemization agent is added in a plurality of steps, it is preferable to add an amount of the condensing agent within the above range in each step.

*Reaction Conditions:

In the first peptide production method of the present invention, the reaction conditions are not restricted as long as the reaction proceeds, but may be exemplified for each of the first and second embodiments as follows.

In the case of the first embodiment, when the silane-containing fused ring dipeptide compound represented by formula (A) is reacted with the protected amino acid or protected peptide represented by formula (R3) at step (i), the reaction conditions are not restricted as long as the reaction proceeds, but may be as follows.

The reaction temperature at step (i) is not restricted as long as the reaction proceeds, but may be 0° C. or more, or 10° C. or more, or 20° C. or more, and 100° C. or less, or 80° C. or less, or 60° C. or less.

The reaction pressure at step (i) is also not limited as long as the reaction proceeds, and the reaction may be carried out under reduced, normal, or pressurized pressure, but may typically be carried out under normal pressure.

The reaction atmosphere at step (i) is also not limited as long as the reaction proceeds, but the reaction may be carried out under an atmosphere of inert gas such as argon or nitrogen.

The reaction time of step (i) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

Next, when the amino acid ester or peptide ester represented by formula (R4) is added to the reaction system at step (ii), the reaction conditions are also not limited as long as the reaction proceeds, but may be as follows.

The reaction temperature at step (ii) is not restricted as long as the reaction proceeds, but may be 0° C. or more, or 10° C. or more, or 20° C. or more, and 100° C. or less, or 80° C. or less, or 60° C. or less.

The reaction pressure at step (ii) is also not limited as long as the reaction proceeds, and the reaction may be carried out under reduced, normal, or pressurized pressure, but may typically be carried out under normal pressure.

The reaction atmosphere at step (ii) is also not limited as long as the reaction proceeds, but the reaction may be carried out under an atmosphere of inert gas such as argon or nitrogen.

The reaction time of step (ii) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

In the case of the second embodiment, when a silane-containing fused ring dipeptide compound represented by formula (A) is reacted with the amino acid ester or peptide ester represented by formula (R4) at step (i), the reaction conditions are not restricted as long as the reaction proceeds, but may be as follows.

The reaction temperature at step (i) is not restricted as long as the reaction proceeds, but may be 0° C. or more, or 10° C. or more, or 20° C. or more, and 100° C. or less, or 80° C. or less, or 60° C. or less.

The reaction pressure at step (i) is also not limited as long as the reaction proceeds, and the reaction may be carried out under reduced, normal, or pressurized pressure, but may typically be carried out under normal pressure.

The reaction atmosphere at step (i) is also not limited as long as the reaction proceeds, but the reaction may be carried out under an atmosphere of inert gas such as argon or nitrogen.

The reaction time of step (i) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

Next, when the protected amino acid or protected peptide represented by formula (R3) is added to the reaction system to cause a further reaction at step (ii), the reaction conditions are also not limited as long as the reaction proceeds, but may be as follows.

The reaction temperature at step (ii) is not restricted as long as the reaction proceeds, but may be 0° C. or more, or 10° C. or more, or 20° C. or more, and 100° C. or less, or 80° C. or less, or 60° C. or less.

The reaction pressure at step (ii) is also not limited as long as the reaction proceeds, and the reaction may be carried out under reduced, normal, or pressurized pressure, but may typically be carried out under normal pressure.

The reaction atmosphere at step (ii) is also not limited as long as the reaction proceeds, but the reaction may be carried out under an atmosphere of inert gas such as argon or nitrogen.

The reaction time of step (ii) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

In both the first and second embodiments, each of steps (i) and (ii) may be carried out in a sequential manner (batch) or in a continuous manner (flow). Details of specific procedures for implementing a sequential method (batch method) and a continuous method (flow method) are well known in the art. Step (i) and step (ii) may be performed consecutively in one pod.

*Polypeptide (Target Compound):

The target compound finally produced in the first polypeptide production method according to the present invention is a polypeptide compound represented by formula (P1).

[Chem. 25]

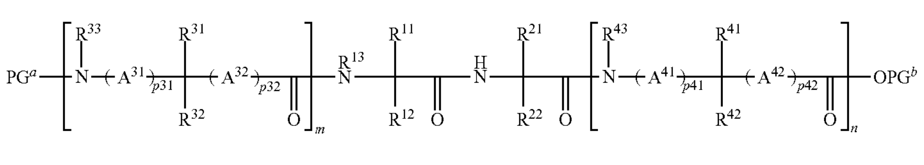

(P1)

In formula (P1), $R^{11}$, $R^{12}$, $R^{13}$, $R^{21}$, and $R^{22}$ each represent the same definition as in formula (A), $PG^a$, $R^{31}$, $R^{32}$, $R^{33}$, $A^{31}$, $A^{32}$, p31, p32, and m each represent the same definition as in formula (R3), and $PG^b$, $R^{41}$, $R^{42}$, $R^{43}$, $A^{41}$, $A^{42}$, p41, p42, and n each represent the same definition as in formula (R4).

The compound of formula (P1) is a polypeptide compound whose number of amino acid residues is m+n+2. Specifically, when the compound of formula (R3) is a protected amino acid and the compound of formula (R4) is an amino acid ester (i.e., when m and n are both 1), the resulting compound of formula (P1) is a polypeptide compound whose number of amino acid residues is m+n+2=4, i.e., a tetrapeptide compound. When the compound of formula (R3) is a protected dipeptide and the compound of formula (R4) is an amino acid ester (i.e., when m is 2 and n is 1), or when the compound of formula (R3) is a protected amino acid and the compound of formula (R4) is a dipeptide ester (i.e., when m is 1 and n is 2), the resulting compound of formula (P1) is a polypeptide compound whose number of amino acid residues is m+n+2=5, i.e., a pentapeptide compound. When the compound of formula (R3) is a protected dipeptide and the compound of formula (R4) is a dipeptide ester (i.e., when m is 2 and n is 2), the resulting compound of formula (P1) is a polypeptide compound whose number of amino acid residues is m+n+2=6, i.e., a hexapeptide compound. Thus, it is possible to control the number of amino acid residues in the polypeptide compound of formula (P1) (m+n+2) by adjusting the number of amino acid residues in each of the substrates of formulae (R3) and (R4) (m and n).

The polypeptide compound of formula (P1) obtained by the production method mentioned above may be subjected to various post-treatments. Examples of post-treatments include isolation and purification of the polypeptide compound of formula (P1) and deprotection of the amino-protecting group $PG^a$ and/or the carboxyl-protecting group $PG^b$. The post-treatment will be explained later.

(2) Second Polypeptide Production Method:

The second polypeptide production method according to the present invention is a method in which two molecules of the fused ring dipeptide compound of the present invention is used to produce one molecule of the polypeptide compound, and includes at least steps (i) to (iii) below.

(i) The step of causing a reaction between the silane-containing fused ring dipeptide compound represented by formula (A1) the protected amino acid or protected peptide represented by formula (R3).

(ii) The step of causing a further reaction between the reactant from step (i) and the silane-containing fused ring dipeptide compound represented by formula (A2).

(iii) The step of causing a further reaction between the reactant from step (ii) and the amino acid ester or peptide ester represented by formula (R4) to thereby prepare a polypeptide compound represented by formula (P1).

*Silane-Containing Fused Ring Dipeptide Compound (Substrate Compound):

The silane-containing fused ring dipeptide compound to be used in the second polypeptide production method according to the present invention substrate compound is the same as the silane-containing fused ring dipeptide compound represented by formula (A) (the fused ring dipeptide compound according to the present invention), except that two molecules of silane-containing fused ring dipeptide compounds are used for the synthesis of one molecule of target polypeptide. In order to distinguish these two molecules of silane-containing fused ring dipeptide compound, they are represented by formula (A1) and formula (A2).

[Chem. 26]

(A1)

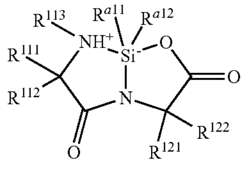

-continued

[Chem. 27]

(A2)

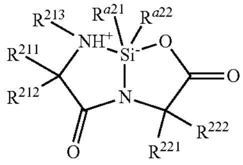

$R^{111}$, $R^{112}$, $R^{113}$, $R^{121}$, and $R^{122}$ in formula (A1) and $R^{211}$, $R^{212}$, $R^{213}$, $R^{221}$, and $R^{222}$ in formula (A2) have, independently of each other, the same definitions as those of $R^{11}$, $R^{12}$, $R^{21}$, and $R^{22}$ in formula (A), respectively. $R^{a11}$ and $R^{a12}$ in formula (A1) and $R^{a21}$ and $R^{a22}$ in formula (A2) have, independently of each other, the same definitions as those of $R^{a1}$ and $R^{a2}$ in formula (A), respectively. The details thereof were explained above.

*Protected Amino Acid/Peptide and Amino Acid/Peptide Ester (Substrates):

The protected amino acid or protected peptide and the amino acid ester or peptide ester to be used in the second polypeptide production method according to the present invention as substrates are the compound represented by formulae (R3) and (R4), as in the first polypeptide production method according to the present invention. The details thereof were explained above.

*Condensing Agent:

In the second peptide production method of the present invention, from the viewpoint of increasing the peptide formation reaction efficiency, a condensing agent may coexist in the system. When a condensing agent is used, an anti-racemization agent may also be used in combination. The details of the condensing agent and the anti-racemization agent were explained for the first peptide production method of the present invention above.

*Base:

In the second peptide production method of the present invention, from the viewpoint of increasing the reaction efficiency, a base may coexist in the system. The details of the base were explained for the first peptide production method of the present invention above.

*Other Ingredients:

In the second peptide production method of the present invention, in addition to the silane-containing fused ring dipeptide compounds represented by formulae (A1) and (A2), the protected amino acid or protected peptide represented by formula (R3), and the amino acid ester or peptide ester represented by formula (R4) as substrates, as well as the base, the condensing agent, and the anti-racemization agent as optional components, other ingredients may coexist. Examples include catalysts, silane compounds, and phosphorus compounds. The details of other ingredient were explained for the first peptide production method of the present invention above.

From the viewpoint of increasing reaction efficiency, the reaction may be carried out in a solvent. The details of the solvent were explained for the first peptide production method of the present invention above.

*Reaction Procedure:

In the second peptide production method of the present invention, the fused ring dipeptide compounds of formulae (A1) and (A2), the protected amino acid or protected peptide compound of formula (R3), and the amino acid ester or peptide ester represented by formula (R4) are reacted. In this reaction, the ring in the amino acid residue on the right side of the fused ring dipeptide compound of formula (A1) and the ring in the amino acid residue on the left side of the fused ring dipeptide compound of formula (A2) are both opened, and the C-terminal of the former amino acid residue is linked to the N-terminal of the latter amino acid residue. Next, the ring in the amino acid residue on the left side of the fused ring dipeptide compound of formula (A1) is opened, and its N-terminal is linked to the protected amino acid or protected peptide represented by formula (R3). Then, the ring in the amino acid residue on the right side of the fused ring dipeptide compound of formula (A2) is opened and linked to the protected amino acid or protected peptide of formula (R4), whereby the polypeptide compound of formula (P2) is formed.

In the second peptide production method of the present invention, the order of mixing each substrate compound is not limited as long as the above reaction occurs. Examples include, although are not limited to, the following two embodiments.

In the first embodiment, as step (i), the silane-containing fused ring dipeptide compound represented by formula (A1) is reacted with the protected amino acid or protected peptide represented by formula (R3). Next, as step (ii), the silane-containing fused ring dipeptide compound represented by formula (A2) is added to the reaction system to cause a further reaction, and as step (iii), the amino acid ester or peptide ester represented by formula (R4) is added to the reaction system to cause a further reaction. According to this embodiment, in step (i), the ring in the amino acid residue on the left side of the fused ring dipeptide compound of formula (A1) is opened, and its N-terminal is linked to the protected amino acid or protected peptide represented by formula (R3). Next, in step (ii), the ring in the amino acid residue on the right side is the fused ring dipeptide compound of formula (A1) and the ring in the amino acid residue on the left side of the fused ring dipeptide compound of formula (A2) are both opened, and the C-terminal of the former amino acid residue is linked to the N-terminal of the latter amino acid residue. Then, in step (iii), the fused ring dipeptide compound of formula (A2) the ring in the amino acid residue on the right side is opened, the protected amino acid or protected peptide of formula (R4), whereby the polypeptide compound of formula (P2) is formed.

In the second embodiment, as step (i), the silane-containing fused ring dipeptide compound represented by formula (A2) is reacted with the amino acid ester or peptide ester represented by formula (R4). Next, as step (ii), the silane-containing fused ring dipeptide compound represented by formula (A1) is added to the reaction system to cause a further reaction, and as step (iii), the protected amino acid or protected peptide represented by formula (R3) is added to the reaction system to cause a further reaction. According to this embodiment, in step (i), the fused ring dipeptide compound of formula (A2) the ring in the amino acid residue on the right side is opened, the protected amino acid or protected peptide of formula (R4). Next, in step (ii), the fused ring dipeptide compound of formula (A1) the ring in the amino acid residue on the right side and the ring in the amino acid residue on the left side of the fused ring dipeptide compound of formula (A2) are both opened, and the C-terminal of the former amino acid residue is linked to the N-terminal of the latter amino acid residue. Then, in step (iii), the fused ring dipeptide compound of formula (A1) the ring in the amino acid residue on the left side is opened, and its N-terminal is linked to the protected amino acid or protected peptide represented by formula (R3), whereby the polypeptide compound of formula (P1) is formed.

The timing for adding other optional components, such as the condensing agent and the base, to the reaction system is not restricted, and any of them can be added at any time. However, when the condensing agent and/or base is used, it may preferably be added to the system at the start of step (i) and/or step (ii) and/or step (iii) in both the first and second embodiments. when the anti-racemization agent is used in addition to the condensing agent, it may preferably be added to the system together with the condensing agent. When the reaction is carried out using a solvent, the other components may be mixed in the solvent and brought into contact with each other.

*Ratios of the Amounts of the Ingredients Used:

In the second peptide production method of the present invention, the amount of each component used is not limited, but may preferably be as follows.

The amount ratio between the fused ring dipeptide compound of formula (A1) and the fused ring dipeptide compound of formula (A2) is not restricted, but relative to 1 mol of the fused ring dipeptide compound of formula (A1), the fused ring dipeptide compound of formula (A2) may be used in an amount of within the range of 0.1 mol or more, or 0.2 mol or more, or 0.3 mol or more, or 0.4 mol or more, or 0.5 mol or more, and 20 mol or less, or 15 mol or less, or 10 mol or less, or 8 mol or less, or 6 mol or less, or 4 mol or less, or 2 mol or less.

The amount ratio between the fused ring dipeptide compound of formula (A1) and the protected amino acid or protected peptide represented by formula (R3) is not restricted, but relative to 1 mol of the fused ring dipeptide compound of formula (A1), the protected amino acid or protected peptide represented by formula (R3) may be used in an amount of within the range of 0.1 mol or more, or 0.2 mol or more, or 0.3 mol or more, or 0.4 mol or more, or 0.5 mol or more, and 20 mol or less, or 15 mol or less, or 10 mol or less, or 8 mol or less, or 6 mol or less, or 4 mol or less, or 2 mol or less.

The amount ratio between the fused ring dipeptide compound of formula (A1) and the amino acid ester or peptide ester represented by formula (R4) is not restricted, but relative to 1 mol of the fused ring dipeptide compound of formula (A1), the amino acid ester or peptide ester represented by formula (R4) may be used in an amount of within the range of 0.1 mol or more, or 0.2 mol or more, or 0.3 mol or more, or 0.4 mol or more, or 0.5 mol or more, and 20 mol or less, or 15 mol or less, or 10 mol or less, or 8 mol or less, or 6 mol or less, or 4 mol or less, or 2 mol or less.

Needless to say, with respect to the target production amount of the polypeptide compound of formula (P2) to be manufactured, it is necessary to use at least 1 mol each of the fused ring dipeptide compound of formula (A), the protected amino acid or protected peptide represented by formula (R3), and the amino acid ester or peptide ester represented by formula (R4) as substrates.

When the base is used, its amount used is not restricted, but relative to 1 mol of the fused ring dipeptide compound of formula (A1), the base may be used in an amount of within the range of 0.2 mol or more, or 0.4 mol or more, or 0.6 mol or more, or 0.8 mol or more, or 1.0 mol or more, and 40 mol or less, or 30 mol or less, or 20 mol or less, or 15 mol or less, or 10 mol or less, or 6 mol or less, or 4 mol or less. When the base is added in a plurality of steps, it is preferable to add an amount of the base within the above range in each step.

When the condensing agent is used, its amount used is not restricted, but relative to 1 mol of the fused ring dipeptide compound of formula (A1), the condensing agent may be used in an amount of within the range of 0.2 mol or more, or 0.4 mol or more, or 0.6 mol or more, or 0.8 mol or more, or 1.0 mol or more, and 40 mol or less, or 30 mol or less, or 20 mol or less, or 15 mol or less, or 10 mol or less, or 6 mol or less, or 4 mol or less. When the condensing agent is added in a plurality of steps, it is preferable to add an amount of the condensing agent within the above range in each step.

When the anti-racemization agent is used in addition to the condensing agent, its amount used is not restricted, but relative to 1 mol of the fused ring dipeptide compound of formula (A1), the anti-racemization agent may be used in an amount of within the range of 0.2 mol or more, or 0.4 mol or more, or 0.6 mol or more, or 0.8 mol or more, or 1.0 mol or more, and 40 mol or less, or 30 mol or less, or 20 mol or less, or 15 mol or less, or 10 mol or less, or 6 mol or less, or 4 mol or less. When the anti-racemization agent is added in a plurality of steps, it is preferable to add an amount of the anti-racemization agent within the above range in each step.

*Reaction Conditions:

In the second peptide production method of the present invention, the reaction conditions are not restricted as long as the reaction proceeds, but may be exemplified for each of the first and second embodiments as follows.

In the case of the first embodiment, when the silane-containing fused ring dipeptide compound represented by formula (A1) is reacted with the protected amino acid or protected peptide represented by formula (R3) at step (i), the reaction conditions are not restricted as long as the reaction proceeds, but may be as follows.

The reaction temperature at step (i) is not restricted as long as the reaction proceeds, but may be 0° C. or more, or 10° C. or more, or 20° C. or more, and 100° C. or less, or 80° C. or less, or 60° C. or less.

The reaction pressure at step (i) is also not limited as long as the reaction proceeds, and the reaction may be carried out under reduced, normal, or pressurized pressure, but may typically be carried out under normal pressure.

The reaction atmosphere at step (i) is also not limited as long as the reaction proceeds, but the reaction may be carried out under an atmosphere of inert gas such as argon or nitrogen.

The reaction time of step (i) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

When the silane-containing fused ring dipeptide compound represented by formula (A2) is reacted with the protected amino acid or protected peptide represented by formula (R3) at step (ii), the reaction conditions are not restricted as long as the reaction proceeds, but may be as follows.

The reaction temperature at step (ii) is not restricted as long as the reaction proceeds, but may be 0° C. or more, or 10° C. or more, or 20° C. or more, and 100° C. or less, or 80° C. or less, or 60° C. or less.

The reaction pressure at step (ii) is also not limited as long as the reaction proceeds, and the reaction may be carried out under reduced, normal, or pressurized pressure, but may typically be carried out under normal pressure.

The reaction atmosphere at step (ii) is also not limited as long as the reaction proceeds, but the reaction may be carried out under an atmosphere of inert gas such as argon or nitrogen.

The reaction time of step (ii) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

When the amino acid ester or peptide ester represented by formula (R4) is added to the reaction system to cause a further reaction at step (iii), the reaction conditions are not restricted as long as the reaction proceeds, but may be as follows.

The reaction temperature at step (iii) is not restricted as long as the reaction proceeds, but may be 0° C. or more, or 10° C. or more, or 20° C. or more, and 100° C. or less, or 80° C. or less, or 60° C. or less.

The reaction pressure at step (iii) is also not limited as long as the reaction proceeds, and the reaction may be carried out under reduced, normal, or pressurized pressure, but may typically be carried out under normal pressure.

The reaction atmosphere at step (iii) is also not limited as long as the reaction proceeds, but the reaction may be carried out under an atmosphere of inert gas such as argon or nitrogen.

The reaction time of step (iii) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

Next, in the case of the second embodiment, when the silane-containing fused ring dipeptide compound represented by formula (A2) is reacted with the protected amino acid or protected peptide represented by formula (R4) at step (i), the reaction conditions are not restricted as long as the reaction proceeds, but may be as follows.

The reaction temperature at step (i) is not restricted as long as the reaction proceeds, but may be 0° C. or more, or 10° C. or more, or 20° C. or more, and 100° C. or less, or 80° C. or less, or 60° C. or less.

The reaction pressure at step (i) is also not limited as long as the reaction proceeds, and the reaction may be carried out under reduced, normal, or pressurized pressure, but may typically be carried out under normal pressure.

The reaction atmosphere at step (i) is also not limited as long as the reaction proceeds, but the reaction may be carried out under an atmosphere of inert gas such as argon or nitrogen.

The reaction time of step (i) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

Next, when the silane-containing fused ring dipeptide compound represented by formula (A1) is added to the reaction system to cause a further reaction in step (ii), the reaction conditions are also not limited as long as the reaction proceeds, but may be as follows.

The reaction temperature at step (ii) is not restricted as long as the reaction proceeds, but may be 0° C. or more, or 10° C. or more, or 20° C. or more, and 100° C. or less, or 80° C. or less, or 60° C. or less.

The reaction pressure at step (ii) is also not limited as long as the reaction proceeds, and the reaction may be carried out under reduced, normal, or pressurized pressure, but may typically be carried out under normal pressure.

The reaction atmosphere at step (ii) is also not limited as long as the reaction proceeds, but the reaction may be carried out under an atmosphere of inert gas such as argon or nitrogen.

The reaction time of step (ii) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

Then, when the protected amino acid or protected peptide represented by formula (R3) is added to the reaction system to cause a further reaction in step (iii), the reaction conditions are also not limited as long as the reaction proceeds, but may be as follows.

The reaction temperature at step (iii) is not restricted as long as the reaction proceeds, but may be 0° C. or more, or 10° C. or more, or 20° C. or more, and 100° C. or less, or 80° C. or less, or 60° C. or less.

The reaction pressure at step (iii) is also not limited as long as the reaction proceeds, and the reaction may be carried out under reduced, normal, or pressurized pressure, but may typically be carried out under normal pressure.

The reaction atmosphere at step (iii) is also not limited as long as the reaction proceeds, but the reaction may be carried out under an atmosphere of inert gas such as argon or nitrogen.

The reaction time of step (iii) is also not limited as long as the reaction proceeds. However, in order for the reaction to proceed sufficiently and efficiently, the reaction time may be 10 minutes or more, or 20 minutes or more, or 30 minutes or more, and for 80 hours or less, or for 60 hours or less, or for 50 hours or less.

In both the first and second embodiments, each of steps (i) and (ii) and (iii) may be carried out in a sequential manner (batch) or in a continuous manner (flow). Details of specific procedures for implementing a sequential method (batch method) and a continuous method (flow method) are well known in the art. Steps (i) and (ii) and/or steps (ii) and (ii) may be performed consecutively in one pod.

*Polypeptide (Target Compound):

The target compound finally produced in the second polypeptide production method according to the present invention is a polypeptide compound represented by formula (P2).

protected amino acid and the compound of formula (R4) is an amino acid ester (i.e., when m and n are both 1), the resulting compound of formula (P2) is a polypeptide compound whose number of amino acid residues is m+n+4=6, i.e., a hexapeptide compound. When the compound of formula (R3) is a protected dipeptide and the compound of formula (R4) is an amino acid ester (i.e., when m is 2 and n is 1), or when the compound of formula (R3) is a protected amino acid and the compound of formula (R4) is a dipeptide ester (i.e., when m is 1 and n is 2), the resulting compound of formula (P2) is a polypeptide compound whose number of amino acid residues is m+n+4=7, i.e., a heptapeptide compound. Thus, it is possible to control the number of amino acid residues in the polypeptide compound of formula (P2) (m+n+4) by adjusting the number of amino acid residues in each of the substrates of formulae (R3) and (R4) (m and n).

The polypeptide compound of formula (P2) obtained by the production method mentioned above may be subjected to various post-treatments. Examples of post-treatments include isolation and purification of the polypeptide compound of formula (P2) and deprotection of the amino-protecting group $PG^a$ and/or the carboxyl-protecting group $PG^b$. The post-treatment will be explained later.

(3) Others:

The polypeptide compound of formula (P1) or formula (P2) obtained by the production method mentioned above may be subjected to various post-treatments.

For example, the polypeptide compound of formula (P1) or formula (P2) obtained by the production method mentioned above can be isolated and purified according to conventional methods such as column chromatography and recrystallization.

In addition, the polypeptide compound of formula (P1) or formula (P2) obtained by the production method mentioned above can be subjected to deprotection of the amino group protected by the protecting group $PG^a$. The method of deprotecting the amino group protected by $PG^1$ is not particularly restricted, and various methods can be used depending on the type of protecting group $PG^1$. Examples include deprotection by hydrogenation, deprotection by weak acids, deprotection by fluorine ions, deprotection by one-electron oxidants, deprotection by hydrazine, and deprotection by oxygen. The deprotection by hydrogenation may be carried out by, e.g.; (a) a method of causing

[Chem. 28]

(P2)

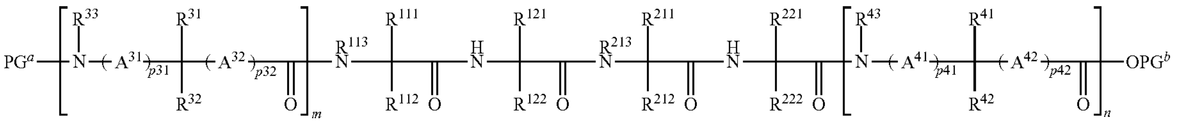

In formula (P2), $R^{111}$, $R^{112}$, $R^{113}$, $R^{121}$, and $R^{122}$ each represent the same definition as in formula (A1), $R^{211}$, $R^{212}$, $R^{213}$, $R^{221}$, and $R^{222}$ each represent the same definition as in formula (A2), $PG^a$, $R^{31}$, $R^{32}$, $R^{33}$, $A^{31}$, $A^{32}$, p31, p32, and m each represent the same definition as in formula (R3), $PG^b$, $R^{41}$, $R^{42}$, $R^{43}$, $A^{41}$, $A^{42}$, p41, p42, and n each represent the same definition as in formula (R4).

The compound of formula (P2) is a polypeptide compound whose number of amino acid residues is m+n+4. Specifically, when the compound of formula (R3) is a deprotection in the presence of hydrogen gas using a metal catalyst such as palladium, palladium-carbon, palladium hydroxide, palladium-carbon hydroxide, etc., as a reduction catalyst; and (b) a method of causing deprotection in the presence of a metal catalyst such as palladium, palladium-carbon, palladium hydroxide, palladium-carbon hydroxide, etc., using a hydrotreating reductant such as sodium borohydride, lithium aluminum hydride, lithium borohydride, diborane, etc.

Likewise, the polypeptide compound of formula (P1) or formula (P2) obtained by the production method mentioned above can be subjected to deprotection of the carboxyl group protected by the protecting group $PG^b$. The method of deprotecting the carboxyl group protected by $PG^2$ is not particularly restricted, and various methods can be used depending on the type of protecting group $PG^2$. Examples include deprotection by hydrogenation, deprotection by bases, and deprotection by weak acids. In the case of deprotection with a base, a strong base such as lithium hydroxide, sodium hydroxide, potassium hydroxide, etc. can be used.

In addition, the polypeptide compound of formula (P1) or formula (P2) obtained by the production method mentioned above may be used (after deprotection if necessary) as a protected peptide of formula (R3) and/or a peptide ester of formula (R4) again for the first or second peptide production method of the present invention. Alternatively, the polypeptide compound of formula (P1) or formula (P2) obtained by the production method mentioned above may be subjected (after deprotection if necessary) to other conventionally known amidation or peptide production methods. Thus, a polypeptide compound of formula (P1) or formula (P2) can be linked to other amino acids or peptides by amide bonding to elongate the amino acid residues and synthesize larger polypeptides. Polypeptides of any number of amino acid residues and amino acid sequences can in principle be synthesized by sequentially repeating these steps.

The present inventors have filed the following prior patent applications relating to amidation reactions for linking amino acids or peptides and methods for producing polypeptides thereby. It is possible to perform the various polypeptide production methods of the present invention in combination with the amidation reactions and polypeptide production methods described in these earlier patent applications as appropriate and/or to modify the amidation reactions and polypeptide production methods described in these prior patent applications as appropriate, taking into account the conditions of these prior patent applications. The descriptions of these earlier patent applications are incorporated herein by reference in their entirety.

(1) WO2017/204144 (May 22, 2017)

(2) WO2018/199146 (Apr. 25, 2018)

(3) WO2018/199147 (Apr. 25, 2018)

(4) WO2019/208731 (Apr. 25, 2019)

(5) PCT/JP2020/040951 (Oct. 30, 2020)

(6) PCT/JP2020/040960 (Oct. 30, 2020)

(7) PCT/JP2021/002306 (Jan. 22, 2021)

EXAMPLES

The present invention will be described in more detail below with reference to examples. However, the present invention should in no way be bound by the following examples, and can be implemented in any form within the scope that does not depart from the purpose of the invention. Amino acids described below that have optical isomers shall refer to the L-form, unless otherwise specified.

Example Group I: Preparation of Fused Ring Dipeptide Compounds

*General Synthesis Procedure I(1):

[Chem. 29]

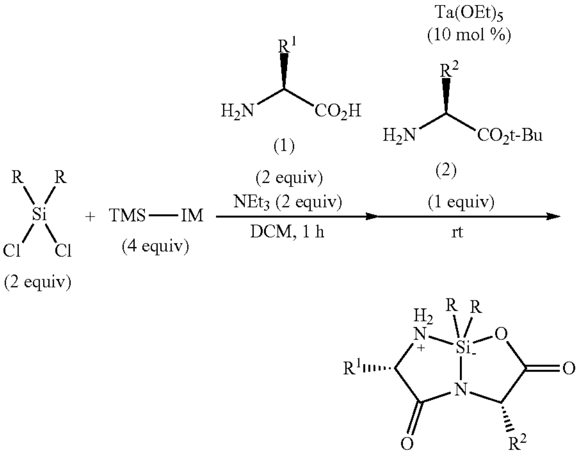

A test tube with a volume of 16 mL is charged with a stirrer bar, a non-protected amino acid (2 equivalents), silyl dichloride (2 equivalents), trimethylsilylimidazole (TMS-IM, 146.7 μL, 4 equivalents), and triethylamine (70 μL, 2 equivalents), as well as dichloromethane (DCM), and the mixture is agitated at room temperature for one hour. The test tube is then placed in a glove box, and tantalum ethoxide (6.5 μL, 10 mol %) and amino acid tert-butyl ester (0.25 mmol) are added to the mixture, which is agitated at room temperature or at 50° C. for 24 hours. After reaction, the mixture is diluted with chloroform (4.50 mL), and the product is isolated by silica gel column chromatography to obtain the target compound.

*General Synthesis Procedure I(2):

[Chem. 30]

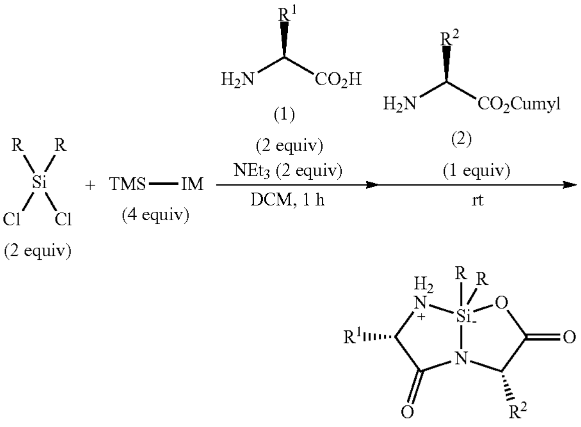

A test tube with a volume of 16 mL is charged with a stirrer bar, a non-protected amino acid (2 equivalents), silyl dichloride (2 equivalents), trimethylsilyl imidazole (TMS-IM, 146.7 μL, 4 equivalents), and triethyl amine (70 μL, 2 equivalents), as well as dichloromethane (DCM), and the mixture is agitated at room temperature for one hour. The test tube is then placed in a glove box, and an amino acid cumyl ester (0.25 mmol) is added to the mixture, which is agitated at room temperature for 24 hours (without using a Lewis acid catalyst such as tantalum ethoxide). After reaction, the mixture is diluted with chloroform (4.50 mL), and the product is isolated by silica gel column chromatography to obtain the target compound.

The amino acid cumyl esters used in the reaction can be synthesized by the following procedure, referring to, e.g., Roesner et al, Chem. Sci., 2019, 10:2465-2472. A test tube is charged with 2-phenyl-2-propanol (2.2 equivalents) and sodium hydroxide (0.5 equivalents), as well as diethyl ether, and the mixture is agitated at 0° C. to at room temperature for one hour to cause a reaction. Trichloroacetonitrile (2 equivalents) is then added to the test tube, and the mixture is agitated at 0° C. to at room temperature for 3 hours to cause a further reaction. After filtering out the solids with diethyl ether on filter paper, the solvent is removed under reduced pressure. Then, the mixture is combined with 1 equivalent of a Fmoc-protected amino acid, which is derived from the amino acid corresponding to the desired amino acid cumyl ester by protecting the amino group with a Fmoc group, and reacted in dichloromethane at room temperature overnight with stirring to obtain a Fmoc-protected amino acid cumyl ester. Finally, diethylamine (2 equivalents) is added to the mixture to cause a reaction in dichloromethane at room temperature for 1 hour to deprotect the Fmoc group to obtain the desired amino acid cumyl ester.

*Example I(1): Synthesis of Using Fused Ring Dipeptide Compound —Si(Me)$_2$-Phe-Ala-

[Chem. 31]

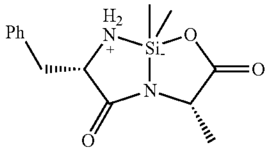

According to General Synthesis Procedure I (1), L-phenylalanine (82.6 mg, 0.500 mmol), dimethyl dichlorosilane (59.8 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at room temperature for 24 hours. After the reaction, the product was isolated by column chromatography with ethyl acetate/hexane (4/1), whereby the title compound was obtained as white solid with a yield of 86% (62.8 mg). The diastereomer ratio was >17:1.

*Example I(2): Synthesis of Using Fused Ring Dipeptide Compound —Si(Me,Ph)-Phe-Ala-

[Chem. 32]

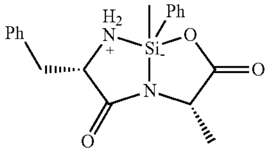

According to General Synthesis Procedure I (1), L-phenylalanine (82.6 mg, 0.500 mmol), dichloromethylphenyl silane (80.5 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at room temperature for 24 hours. After the reaction, the product was isolated by column chromatography with ethyl acetate/hexane (4/1), whereby the title compound was obtained as white solid with a yield of 48% (42.5 mg). The diastereomer ratio was >20:1.

*Example I(3): Synthesis of Using Fused Ring Dipeptide Compound —Si(Ph)$_2$-Phe-Ala-

[Chem. 33]

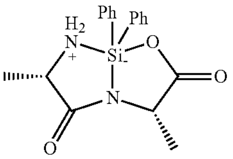

According to General Synthesis Procedure I (1), L-phenylalanine (82.6 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at room temperature for 24 hours. After the reaction, the product was isolated by column chromatography with ethyl acetate/hexane (4/1), whereby the title compound was obtained as white solid with a yield of 91% (77.4 mg). The diastereomer ratio was >20:1.

*Example I(4): Synthesis of Using Fused Ring Dipeptide Compound —$Si(Ph)_2$-Val-Ala-

[Chem. 34]

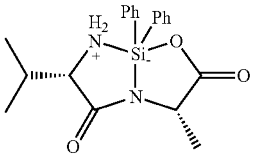

According to General Synthesis Procedure I (1), L-valine (58.6 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol) and L-alanine tert-butyl ester (36.3 mg, 0.250 mmol) were added to the mixture, which was agitated at 50° C. for 24 hours. After the reaction, the product was isolated by column chromatography with ethyl acetate/hexane (3/2), whereby the title compound was obtained as white solid with a yield of 83% (76.4 mg). The diastereomer ratio was >20:1.

*Example I(5): Synthesis of Using Fused Ring Dipeptide Compound —$Si(Ph)_2$-Ile-Ala-

[Chem. 35]

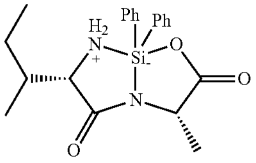

According to General Synthesis Procedure I (1), L-isoleucine (65.6 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at 50° C. for 24 hours. After the reaction, the product was isolated by column chromatography with ethyl acetate/hexane (1/1), whereby the title compound was obtained as white solid with a yield of 76% (72.6 mg). The diastereomer ratio was >20:1.

*Example I(6): Synthesis of Using Fused Ring Dipeptide Compound —$Si(Ph)_2$-Leu-Ala-

[Chem. 36]

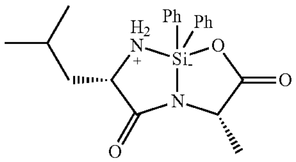

According to General Synthesis Procedure I (1), L-leucine (65.6 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at 50° C. for 24 hours. After the reaction, the product was isolated by column chromatography with ethyl acetate/hexane (1/1), whereby the title compound was obtained as white solid with a yield of 85% (81.2 mg). The diastereomer ratio was >20:1.

*Example I(7): Synthesis of Using Fused Ring Dipeptide Compound —$Si(Ph)_2$-Ser(t-Bu)-Ala-

[Chem. 37]

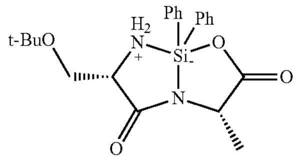

According to General Synthesis Procedure I (1), O-tert-butyl-L-serine (80.6 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at room temperature for 24 hours. After the reaction, the product was isolated by column chromatography with ethyl acetate/hexane (3/2), whereby the title compound was obtained as white solid with a yield of 92% (94.8 mg). The diastereomer ratio was >20:1.

*Example I(8): Synthesis of Using Fused Ring Dipeptide Compound —$Si(Ph)_2$-Thr(t-Bu)-Ala-

[Chem. 38]

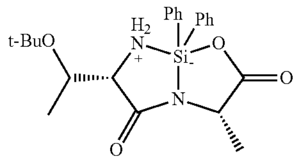

According to General Synthesis Procedure I (1), O-tert-butyl-L-threonine (87.6 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at room temperature for 24 hours. After the reaction, the product was isolated by column chromatography with ethyl acetate/hexane (3/2), whereby the title compound was obtained as white solid with a yield of 91% (97.0 mg). The diastereomer ratio was >20:1.

*Example I(9): Synthesis of Using Fused Ring Dipeptide Compound —Si(Ph)$_2$-Met-Ala-

[Chem. 39]

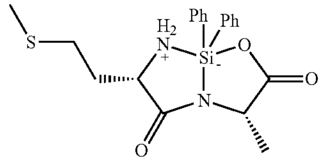

According to General Synthesis Procedure I (1), L-methionine (74.6 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at 50° C. for 24 hours. After the reaction, the product was isolated by column chromatography with ethyl acetate/hexane (3/2), whereby the title compound was obtained as white solid with a yield of 92% (92.0 mg). The diastereomer ratio was >20:1.

*Example I(10): Synthesis of Using Fused Ring Dipeptide Compound —Si(Ph)$_2$-Lys(Boc)-Ala-

[Chem. 40]

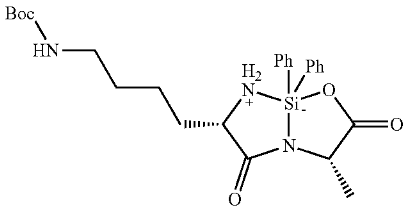

According to General Synthesis Procedure I (1), $N^{\varepsilon}$-Boc-L-lysine (123 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at room temperature for 24 hours. After the reaction, the product was isolated by column chromatography with ethyl acetate/hexane (3/2), whereby the title compound was obtained as white solid with a yield of 88% (109 mg). The diastereomer ratio was >20:1.

*Example I(11): Synthesis of Using Fused Ring Dipeptide Compound —Si(Ph)$_2$-Tyr(t-Bu)-Ala-

[Chem. 41]

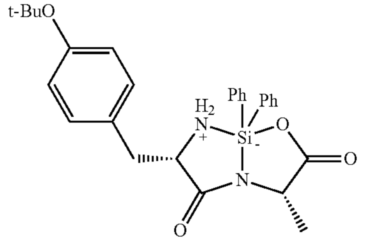

According to General Synthesis Procedure I (1), O-tert-butyl-L-tyrosine (119 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at room temperature for 24 hours. After the reaction, the product was isolated by column chromatography with ethyl acetate/hexane (1/1), whereby the title compound was obtained as white solid with a yield of 90% (110 mg). The diastereomer ratio was >20:1.

*Example I(12): Synthesis of Using Fused Ring Dipeptide Compound —Si(Ph)$_2$-Trp(Boc)-Ala-

[Chem. 42]

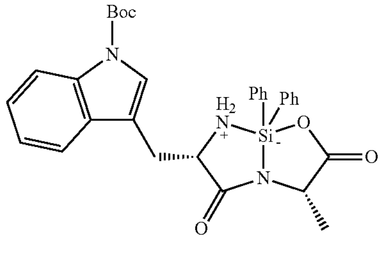

According to General Synthesis Procedure I (1), $N^1$—Boc-L-tryptophan (152 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at room temperature for 24 hours. After the reaction, the product was isolated by column chromatography with ethyl acetate/hexane (1/1), whereby the title compound was obtained as white solid with a yield of 81% (112 mg). The diastereomer ratio was >20:1.

*Example I(13): Synthesis of Using Fused Ring Dipeptide Compound —Si(Ph)$_2$-Asp(t-Bu)-Ala-

[Chem. 43]

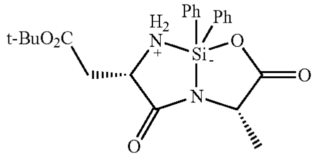

According to General Synthesis Procedure I (1), L-aspartic acid 4-tert-butyl (94.6 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at room temperature for 24 hours. After the reaction, the product was isolated by column chromatography with ethyl acetate/hexane (1/1), whereby the title compound was obtained as white solid with a yield of 95% (105 mg). The diastereomer ratio was >20:1.

*Example I(14): Synthesis of Using Fused Ring Dipeptide Compound —Si(Ph)$_2$-Glu(t-Bu)-Ala-

[Chem. 44]

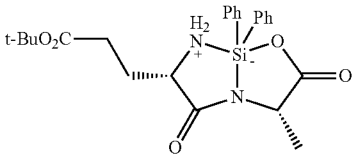

According to General Synthesis Procedure I (1), L-glutamic acid 5-tert-butyl (102 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at room temperature for 24 hours. After the reaction, the product was isolated by column chromatography with ethyl acetate/hexane (1/1), whereby the title compound was obtained as white solid with a yield of 93% (105 mg). The diastereomer ratio was >20:1.

*Example I(15): Synthesis of Using Fused Ring Dipeptide Compound —Si(Ph)$_2$-Aib-Gly-

[Chem. 45]

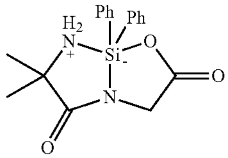

According to General Synthesis Procedure I (1), 2-amino isobutyric acid (51.6 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), glycine tert-butyl ester (32.8 mg, 0.250 mmol) were added to the mixture, which was agitated at room temperature for 24 hours. After the reaction, the product was isolated by column chromatography with ethyl acetate/hexane (1/1), whereby the title compound was obtained as colorless solid with a yield of 84% (71.4 mg).

*Example I(16): Synthesis of Using Fused Ring Dipeptide Compound —Si(Ph)$_2$-Ala-Val-

[Chem. 46]

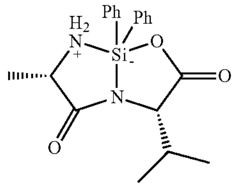

According to General Synthesis Procedure I (1), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-valine tert-butyl ester (43.3 mg, 0.250 mmol) were added to the mixture, which was agitated at room temperature for 24 hours. After the reaction, the product was isolated by column chromatography with ethyl acetate/hexane (1/1), whereby the title compound was obtained as white solid with a yield of 81% (74.6 mg). The diastereomer ratio was >20:1.

*Example I(17): Synthesis of Using Fused Ring Dipeptide Compound —Si(Ph)$_2$-Ala-Ser(t-Bu)-

[Chem. 47]

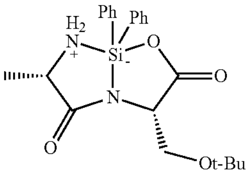

According to General Synthesis Procedure I (1), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), O-tert-butyl-L-serine tert-butyl ester (54.3 mg, 0.250 mmol) were added to the mixture, which was agitated at room temperature for 24 hours. After the reaction, the product was isolated by column chromatography with ethyl acetate/hexane (3/2), whereby the title compound was obtained as white solid with a yield of 91% (93.8 mg). The diastereomer ratio was >20:1.

*Example I(18): Synthesis of Using Fused Ring Dipeptide Compound —$Si(Ph)_2$-Ala-Thr(t-Bu)-

[Chem. 48]

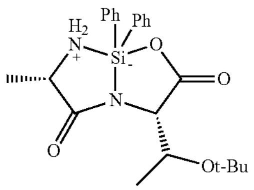

According to General Synthesis Procedure I (1), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), O-tert-butyl-L-threonine tert-butyl ester (57.8 mg, 0.250 mmol) were added to the mixture, which was agitated at room temperature for 24 hours. After the reaction, the product was isolated by column chromatography with ethyl acetate/hexane (2/1), whereby the title compound was obtained as white solid with a yield of 90% (95.9 mg). The diastereomer ratio was >20:1.

*Example I(19): Synthesis of Using Fused Ring Dipeptide Compound —$Si(Ph)_2$-Ala-Met-

[Chem. 49]

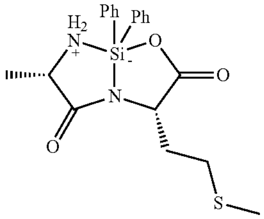

According to General Synthesis Procedure I (1), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-methionine tert-butyl ester (51.3 mg, 0.250 mmol) were added to the mixture, which was agitated at room temperature for 24 hours. After the reaction, the product was isolated by column chromatography with ethyl acetate/hexane (3/2), whereby the title compound was obtained as white solid with a yield of 93% (93.0 mg). The diastereomer ratio was >20:1.

*Example I(20): Synthesis of Using Fused Ring Dipeptide Compound —$Si(Ph)_2$-Ala-Lys(Boc)-

[Chem. 50]

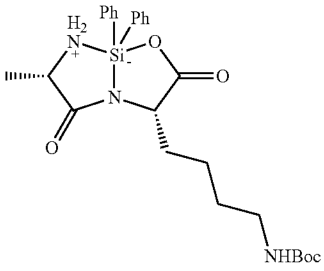

According to General Synthesis Procedure I (1), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), $N^{\varepsilon}$-Boc-L-lysine tert-butyl ester (75.6 mg, 0.250 mmol) were added to the mixture, which was agitated at room temperature for 24 hours. After the reaction, the product was isolated by column chromatography with ethyl acetate/hexane (2/1), whereby the title compound was obtained as white solid with a yield of 87% (108 mg). The diastereomer ratio was >20:1.

*Example I(21): Synthesis of Using Fused Ring Dipeptide Compound —$Si(Ph)_2$-Ala-Glu(t-Bu)-

[Chem. 51]

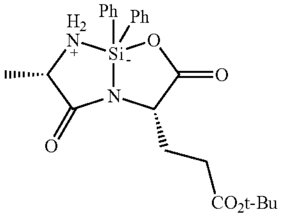

According to General Synthesis Procedure I (1), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-glutamic acid di tert-butyl ester (64.8 mg, 0.250 mmol) were added to the mixture, which was agitated at room temperature for 24 hours. After the reaction, the product was isolated by column chromatography with ethyl acetate/hexane (3/2), whereby the title compound was obtained as white solid with a yield of 93% (106 mg). The diastereomer ratio was >20:1.

*Example I(22): Synthesis of Using Fused Ring Dipeptide Compound —Si(Ph)$_2$-MeAla-Ala-

[Chem. 52]

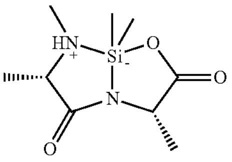

According to General Synthesis Procedure I (1), N-methyl-L-alanine (51.6 mg, 0.500 mmol), dimethyl dichlorosilane (59.8 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), L-alanine tert-butyl ester (36.3 mg, 0.250 mmol) were added to the mixture, which was agitated at room temperature for 24 hours. After the reaction, the product was isolated by column chromatography with ethyl acetate, whereby the title compound was obtained as white solid with a yield of 84% (48.3 mg). The diastereomer ratio was >20:1.

*Example I(23): Synthesis of Using Fused Ring Dipeptide Compound —Si(Ph)$_2$-Ala-Phe-(1)

[Chem. 53]

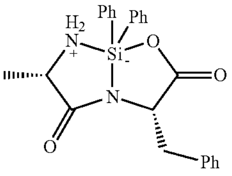

According to General Synthesis Procedure I (1), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), phenylalanine tert-butyl ester (55.3 mg, 0.250 mmol) were added to the mixture, which was agitated at room temperature for 24 hours. After the reaction, the product was isolated by column chromatography with ethyl acetate, whereby the title compound was obtained as white solid with a yield of 91% (94.6 mg). The diastereomer ratio was approximately 4:1.

*Example I(24): Synthesis of Using Fused Ring Dipeptide Compound —Si(Ph)$_2$-Ala-Phe-(2)

[Chem. 54]

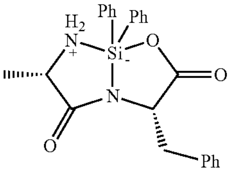

In accordance with General Synthesis Procedure I(2), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and phenylalanine cumyl ester (70.8 mg, 0.250 mmol) were added to the mixture, which was agitated at room temperature for 24 hours. After the reaction, the product was isolated by column chromatography with ethyl acetate, whereby the title compound was obtained as white solid with a yield of 93% (96.8 mg). The diastereomer ratio was >20:1.

*Example I(25): Synthesis of Using Fused Ring Dipeptide Compound —Si(Ph)$_2$-Ala-Tyr(t-Bu)-

[Chem. 55]

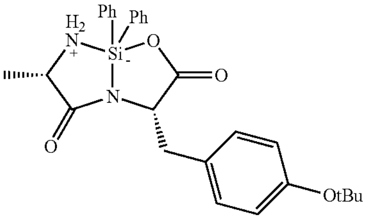

In accordance with General Synthesis Procedure I(2), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and (tert-butyl)tyrosine cumyl ester (88.8 mg, 0.250 mmol) were added to the mixture, which was agitated at room temperature for 24 hours. After the reaction, the product was isolated by column chromatography with ethyl acetate, whereby the title compound was obtained as white solid with a yield of 95% (116 mg). The diastereomer ratio was >20:1.

*Example I(26): Synthesis of Using Fused Ring Dipeptide Compound —Si(Ph)$_2$-Ala-Phg-

[Chem. 56]

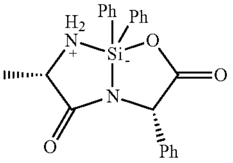

In accordance with General Synthesis Procedure I(2), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and phenylglycine cumyl ester (67.3 mg, 0.250 mmol) were added to the mixture, which was agitated at room temperature for 24 hours. After the reaction, the product was isolated by column chromatography with ethyl acetate, whereby the title compound was obtained as white solid with a yield of 97% (97.5 mg). The diastereomer ratio was >20:1.

*Example I(27): Synthesis of Using Fused Ring Dipeptide Compound —$Si(Ph)_2$-Ala-Cys(Trt)-(1)

[Chem. 57]

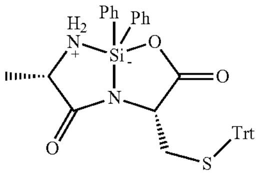

According to General Synthesis Procedure I (1), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and tantalum ethoxide (6.5 μL, 0.0250 mmol), S-trityl cysteine tert-butyl ester (105 mg, 0.250 mmol) were added to the mixture, which was agitated at room temperature for 24 hours. After the reaction, the product was isolated by column chromatography with ethyl acetate, whereby the title compound was obtained as white solid with a yield of 85% (131 mg). The diastereomer ratio was approximately 4:1.

*Example I(28): Synthesis of Using Fused Ring Dipeptide Compound —$Si(Ph)_2$-Ala-Cys(Trt)-(2)

[Chem. 58]

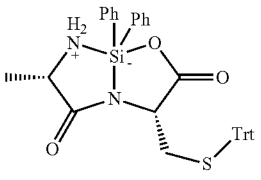

In accordance with General Synthesis Procedure I(2), L-alanine (44.5 mg, 0.500 mmol), dichlorodiphenyl silane (104 μL, 0.500 mmol), TMS-IM (147 μL, 1.00 mmol) and triethyl amine (70.0 μL, 0.500 mmol) were agitated in DCM for one hour. The test tube was then transferred into the glove box, and S-trityl cysteine cumyl ester (120 mg, 0.250 mmol) were added to the mixture, which was agitated at room temperature for 24 hours. After the reaction, the product was isolated by column chromatography with ethyl acetate, whereby the title compound was obtained as white solid with a yield of 91% (140 mg). The diastereomer ratio was >20:1.

Referential Example Group: Reactions of Fused Ring Dipeptide Compounds and Aryl Compounds

*Referential Example (1): Synthesis of Using Fused Ring Dipeptide Compound —$Si(Ph)_2$-Ala-Ala- and Reaction with Benzyl Bromide

[Chem. 59]

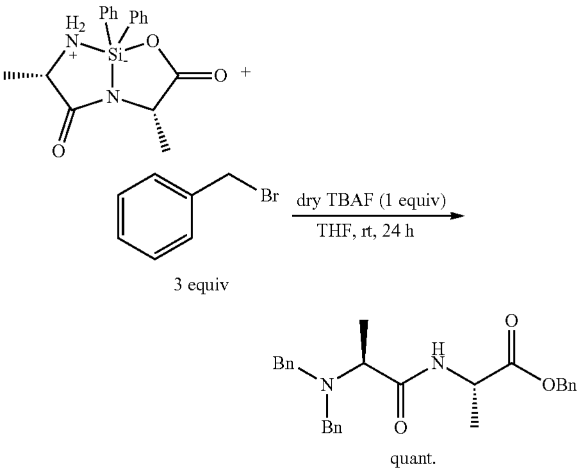

A test tube with a volume of 20 mL was charged with a stirrer bar, a fused ring dipeptide compound (0.25 mmol), TBAF (1 mol/Lin THF) (750 μL, 3.0 equivalents) and benzyl bromide (89 μL, 3.0 equivalents), and THF, and the mixture was agitated at room temperature for 24 hours. After the reaction, the mixture was diluted with chloroform (4.50 mL), and the product was isolated by silica gel column chromatography, whereby the target compound was obtained.

*Referential Example (2): Synthesis of Using Fused Ring Dipeptide Compound —$Si(Ph)_2$-Ala-Ala- and Reaction with Benzyl Amine

[Chem. 60]

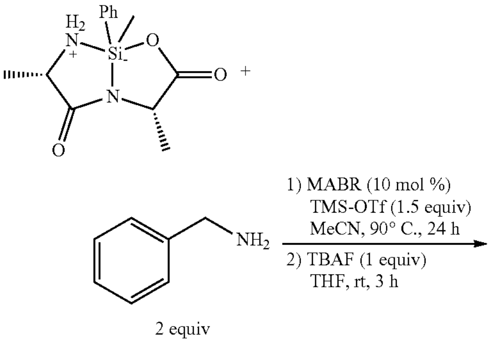

-continued

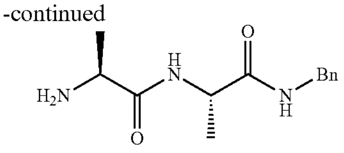

89%

A test tube with a volume of 20 mL was charged with a stirrer bar, a fused ring dipeptide compound (0.25 mmol), methylaluminum bis(4-bromo-2,6-di-tert-butylphenoxyde (MABR: in THF 1 mol/L) (25 μL, 10 mol %), TMS-OTf (67.7 μL, 1.5 equivalents) and benzyl amine (55 μL, 2.0 equivalents), as well as acetonitrile, and the mixture was agitated at 90° C. After 24 hours, TBAF (1 mol/L in THF) (250 μL, 1.0 equivalents) was added to the mixture, which was agitated for 3 hours at room temperature. After the reaction, the mixture was diluted with chloroform (4.50 mL), and the product was isolated by silica gel column chromatography, whereby the target compound was obtained.

Example Group II: Synthesis of Tetra/Penta/Hexapeptides Using Fused Ring Dipeptide Compounds

*General Synthesis Procedure II(1):

[Chem. 61]

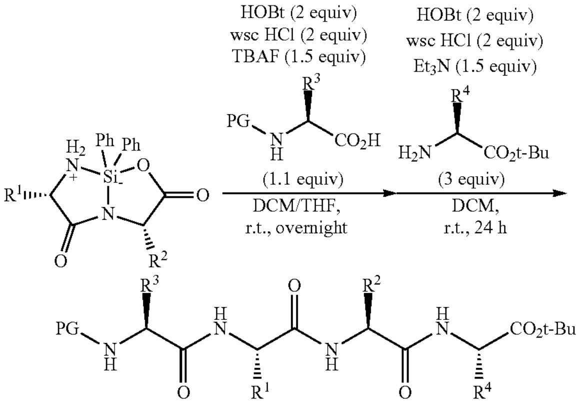

A test tube with a volume of 20 mL is charged with a stirrer bar, a fused ring dipeptide compound (0.25 mmol), TBAF (1 mol/L in THF) (375 μL, 1.5 equivalents), wscHCl (95.9 mg·2 equivalents), HOBt (67.6 mg, 2 equivalents), and N-protected amino acid (1.1 equivalents) as well as DCM, and the mixture is agitated at room temperature overnight. Thereafter, amino acid tert-butyl ester (3 equivalents), wscHCl (95.9 mg·2 equivalents), HOBt (67.6 mg, 2 equivalents), triethyl amine (53 μL, 1.5 equivalents) and DCM (1.00 mL) are added to the test tube, and the mixture is agitated at room temperature for 24 hours. After the reaction, the mixture is diluted with chloroform (4.50 mL), and the product is isolated by silica gel column chromatography, whereby the target compound is obtained.

*General Synthesis Procedure II(2):

[Chem. 62]

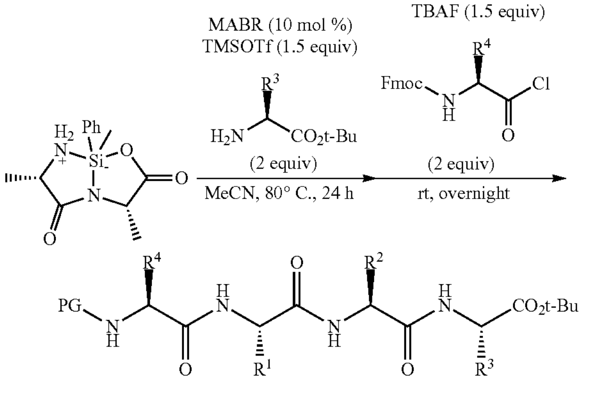

A test tube with a volume of 20 mL was charged with a stirrer bar, a fused ring dipeptide compound (0.25 mmol), trimethylsilyl trifluoromethanesulfonate (TMS-OTf) (1 mol/L in THF) (67.8 μL, 1.5 equivalents), methyl aluminum bis(4-bromo-2,6-di-tert-butylphenoxyde (MABR)hexane solution (12.5 μL, 10 mol %), and an amino acid tert-butyl ester (2 equivalents), as well as acetonitrile (MeCN), and the mixture is heated at 80° C. and agitated for 24 hours. Thereafter, the mixture in the test tube is combined with an amino acid whose amino group has been protected with a Fmoc group and whose carboxyl group has been converted into a carbonyl chloride group (2 equivalents) and TBAF (1 mol/L in THF) (500 μL, 2 equivalents), and agitated at room temperature overnight. After the reaction, the mixture is diluted with chloroform (4.50 mL), and the product is isolated by silica gel column chromatography, whereby the target compound is obtained.

*Example II(1): Synthesis of Tetrapeptide Cbz-Ala-Ala-Ala-Ala-Ot-Bu Using Fused Ring Dipeptide Compound —$Si(Ph)_2$-Ala-Ala-

[Chem. 63]

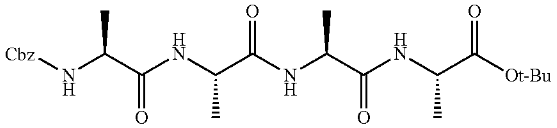

According to General Synthesis Procedure II(1), fused ring dipeptide compound —$Si(Ph)_2$-L-Ala-L-Ala-(85.0 mg, 0.250 mmol), Cbz-alanine (61.4 mg, 0.275 mmol), TBAF (1 mol/L in THF) (375 μL, 0.375 mmol), wscHCl (95.9 mg·0.500 mmol), and HOBt (67.6 mg, 0.500 mmol) in THF were agitated under nitrogen atmosphere overnight at room temperature. Thereafter, alanine tert-butyl ester (109 mg, 0.750 mmol), wscHCl (95.9 mg·0.500 mmol), HOBt (67.6 mg, 0.500 mmol), triethyl amine (52.4 μL, 0.375 mmol), and DCM (1 mL) were added to the mixture, which was agitated at room temperature for 24 hours. After the reaction, the product was isolated by column chromatography with ethyl acetate, whereby the title compound was obtained as white solid with a yield of 82% (101 mg).

*Example II(2): Synthesis of Tetrapeptide Fmoc-Ala-Ala-Ala-Ala-Ot-Bu Using Fused Ring Dipeptide —$Si(Ph)_2$-Ala-Ala-

[Chem. 64]

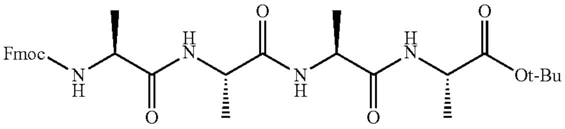

According to General Synthesis Procedure II(1), fused ring dipeptide compound —$Si(Ph)_2$-L-Ala-L-Ala-(85.0 mg, 0.250 mmol), Fmoc-alanine (85.6 mg, 0.275 mmol), TBAF (1 mol/L in THF) (375 μL, 0.375 mmol), wscHCl (95.9 mg·0.500 mmol), and HOBt (67.6 mg, 0.500 mmol) in THF were agitated under nitrogen atmosphere overnight at room temperature. Thereafter, alanine tert-butyl ester (109 mg, 0.750 mmol), wscHCl (95.9 mg·0.500 mmol), HOBt (67.6 mg, 0.500 mmol), triethyl amine (52.4 μL, 0.375 mmol), and DCM (1 mL) were added to the mixture, which was agitated at room temperature for 24 hours. After the reaction, the product was isolated by column chromatography with ethyl acetate, whereby the title compound was obtained as white solid with a yield of 81% (118 mg).

*Example II(3): Synthesis of Tetrapeptide Cbz-Ser(t-Bu)-Ala-Ala-Ala-Ot-Bu Using Fused Ring Dipeptide Compound —$Si(Ph)_2$-Ala-Ala-

[Chem. 65]

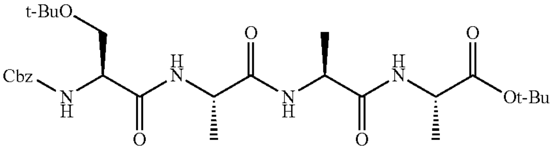

According to General Synthesis Procedure II(1), fused ring dipeptide compound —$Si(Ph)_2$-L-Ala-L-Ala-(85.0 mg, 0.250 mmol), Cbz-O-tert-butyl serine (81.2 mg, 0.275 mmol), TBAF (1 mol/L in THF) (375 μL, 0.375 mmol), wscHCl (95.9 mg·0.500 mmol), and HOBt (67.6 mg, 0.500 mmol) in THF were agitated under nitrogen atmosphere overnight at room temperature. Thereafter, alanine tert-butyl ester (109 mg, 0.750 mmol), wscHCl (95.9 mg·0.500 mmol), HOBt (67.6 mg, 0.500 mmol), triethyl amine (52.4 μL, 0.375 mmol), and DCM (1 mL) were added to the mixture, which was agitated at room temperature for 24 hours. After the reaction, the product was isolated by column chromatography with ethyl acetate/hexane (9/1), whereby the title compound was obtained as colorless solid with a yield of 77% (109 mg).

*Example II(4): Synthesis of Tetrapeptide Cbz-Met-Ala-Ala-Ala-Ot-Bu Using Fused Ring Dipeptide Compound —$Si(Ph)_2$-Ala-Ala-

[Chem. 66]

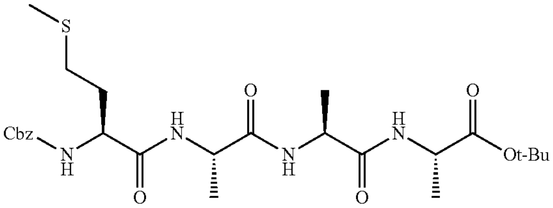

According to General Synthesis Procedure II(1), fused ring dipeptide compound —$Si(Ph)_2$-L-Ala-L-Ala-(85.0 mg, 0.250 mmol), Cbz-methionine (77.9 mg, 0.275 mmol), TBAF (1 mol/L in THF) (375 μL, 0.375 mmol), wscHCl (95.9 mg·0.500 mmol), and HOBt (67.6 mg, 0.500 mmol) in THF were agitated under nitrogen atmosphere overnight at room temperature. Thereafter, alanine tert-butyl ester (109 mg, 0.750 mmol), wscHCl (95.9 mg·0.500 mmol), HOBt (67.6 mg, 0.500 mmol), triethyl amine (52.4 μL, 0.375 mmol), and DCM (1 mL) were added to the mixture, which was agitated at room temperature for 24 hours. After the reaction, the product was isolated by column chromatography with ethyl acetate/hexane (9/1), whereby the title compound was obtained as colorless solid with a yield of 68% (93.9 mg).

*Example II(5): Synthesis of Tetrapeptide Cbz-Lys(Boc)-Ala-Ala-Ala-Ot-Bu Using Fused Ring Dipeptide Compound —$Si(Ph)_2$-Ala-Ala-

[Chem. 67]

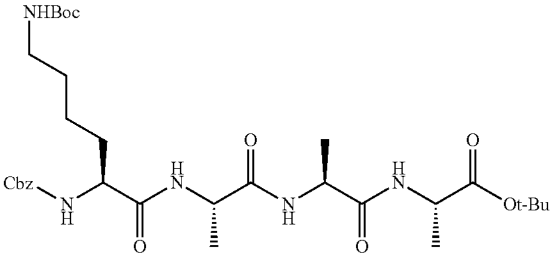

According to General Synthesis Procedure II(1), fused ring dipeptide compound —$Si(Ph)_2$-L-Ala-L-Ala-(85.0 mg, 0.250 mmol), $N^{\alpha}$-Cbz-$N^{\varepsilon}$-Boc-lysine (105 mg, 0.275 mmol), TBAF (1 mol/L in THF) (375 μL, 0.375 mmol), wscHCl (95.9 mg·0.500 mmol), and HOBt (67.6 mg, 0.500 mmol) in THF were agitated under nitrogen atmosphere overnight at room temperature. Thereafter, alanine tert-butyl ester (109 mg, 0.750 mmol), wscHCl (95.9 mg·0.500 mmol), HOBt (67.6 mg, 0.500 mmol), triethyl amine (52.4 μL, 0.375 mmol), and DCM (1 mL) were added to the mixture, which was agitated at room temperature for 24 hours. After the reaction, the product was isolated by column chromatography with ethyl acetate/hexane (9/1), whereby the title compound was obtained as colorless solid with a yield of 81% (131 mg).

*Example II(6): Synthesis of Tetrapeptide Cbz-Trp (Boc)-Ala-Ala-Ala-Ot-Bu Using Fused Ring Dipeptide Compound —$Si(Ph)_2$-Ala-Ala-

[Chem. 68]

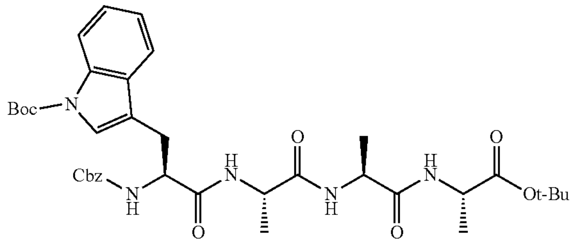

According to General Synthesis Procedure II(1), fused ring dipeptide compound —$Si(Ph)_2$-L-Ala-L-Ala-(85.0 mg, 0.250 mmol), $N^{\alpha}$-Cbz-$N^{in}$-Boc-tryptophan (171 mg, 0.275 mmol), TBAF (1 mol/L in THF) (375 μL, 0.375 mmol), wscHCl (95.9 mg·0.500 mmol), and HOBt (67.6 mg, 0.500 mmol) in THF were agitated under nitrogen atmosphere overnight at room temperature. Thereafter, alanine tert-butyl ester (109 mg, 0.750 mmol), wscHCl (95.9 mg·0.500 mmol), HOBt (67.6 mg, 0.500 mmol), triethyl amine (52.4 μL, 0.375 mmol), and DCM (1 mL) were added to the mixture, which was agitated at room temperature for 24 hours. After the reaction, the product was isolated by column chromatography with ethyl acetate/hexane (3/1), whereby the title compound was obtained as colorless solid with a yield of 68% (120 mg).

*Example II(7): Synthesis of Tetrapeptide Cbz-Ala-Ala-Ala-Met-Ot-Bu Using Fused Ring Dipeptide Compound —$Si(Ph)_2$-Ala-Ala-

[Chem. 69]

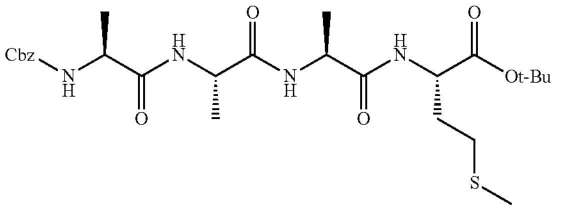

According to General Synthesis Procedure II(1), fused ring dipeptide compound —$Si(Ph)_2$-L-Ala-L-Ala- (85.0 mg, 0.250 mmol), Cbz-alanine (61.4 mg, 0.275 mmol), TBAF (1 mol/L in THF) (375 μL, 0.375 mmol), wscHCl (95.9 mg·0.500 mmol), and HOBt (67.6 mg, 0.500 mmol) in THF were agitated under nitrogen atmosphere overnight at room temperature. Thereafter, methionine tert-butyl ester (154 mg, 0.750 mmol), wscHCl (95.9 mg·0.500 mmol), HOBt (67.6 mg, 0.500 mmol), triethyl amine (52.4 μL, 0.375 mmol), and DCM (1 mL) were added to the mixture, which was agitated at room temperature for 24 hours. After the reaction, the product was isolated by column chromatography with ethyl acetate/hexane (17/3), whereby the title compound was obtained as colorless solid with a yield of 61% (84.2 mg).

*Example II(8): Synthesis of Tetrapeptide Cbz-Ala-Ala-Ala-Glu(t-Bu)-Ot-Bu Using Fused Ring Dipeptide Compound —$Si(Ph)_2$-Ala-Ala-

[Chem. 70]

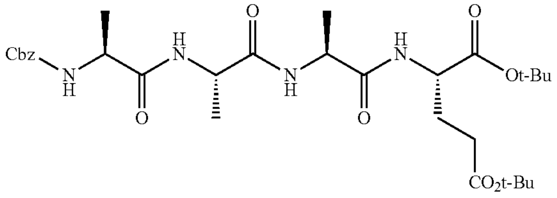

According to General Synthesis Procedure II(1), fused ring dipeptide compound —$Si(Ph)_2$-L-Ala-L-Ala-(85.0 mg, 0.250 mmol), Cbz-alanine (61.4 mg, 0.275 mmol), TBAF (1 mol/L in THF) (375 μL, 0.375 mmol), wscHCl (95.9 mg·0.500 mmol), and HOBt (67.6 mg, 0.500 mmol) in THF were agitated under nitrogen atmosphere overnight at room temperature. Thereafter, glutamic acid di tert-butyl ester (194 mg, 0.750 mmol), wscHCl (95.9 mg·0.500 mmol), HOBt (67.6 mg, 0.500 mmol), triethyl amine (52.4 μL, 0.375 mmol), and DCM (1 mL) were added to the mixture, which was agitated at room temperature for 24 hours. After the reaction, the product was isolated by column chromatography with ethyl acetate/hexane (9/1), whereby the title compound was obtained as colorless solid with a yield of 61% (92.5 mg).

*Example II(9): Synthesis of Pentapeptide Cbz-Aib-Gly-Ala-Ala-Ala-Ot-Bu Using Fused Ring Dipeptide Compound —$Si(Ph)_2$-Ala-Ala-

[Chem. 71]

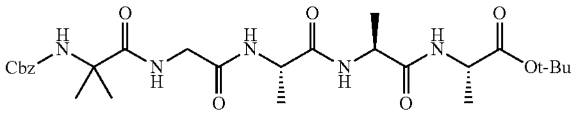

According to General Synthesis Procedure II(1), fused ring dipeptide compound —$Si(Ph)_2$-L-Ala-L-Ala-(85.0 mg, 0.250 mmol), Cbz-Aib-Gly-OH (80.8 mg, 0.275 mmol), TBAF (1 mol/L in THF) (375 μL, 0.375 mmol), wscHCl (95.9 mg·0.500 mmol), and HOBt (67.6 mg, 0.500 mmol) in THF were agitated under nitrogen atmosphere overnight at room temperature. Thereafter, alanine tert-butyl ester (109 mg, 0.750 mmol), wscHCl (95.9 mg·0.500 mmol), HOBt (67.6 mg, 0.500 mmol), triethyl amine (52.4 μL, 0.375 mmol), and DCM (1 mL) were added to the mixture, which was agitated at room temperature for 24 hours. After the reaction, the product was isolated by column chromatography with methanol/chloroform (1/10), whereby the title compound was obtained as colorless solid with a yield of 55% (77.5 mg).

*Example II(10): Synthesis of Tetrapeptide Fmoc-Ala-Ala-Ala-Ala-O-t-Bu Using Fused Ring Dipeptide Compound —Si(Me,Ph)-Ala-Ala-

[Chem. 72]

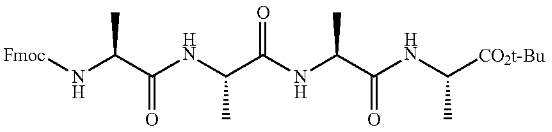

According to General Synthesis Procedure II(2), fused ring dipeptide compound —Si(Me,Ph)-L-Ala-L-Ala-(85.0 mg, 0.250 mmol), TMS-OTf) (1 mol/L in THF) (67.8 μL, 1.5 equivalents), hexane solution of MABR (12.5 μL, 10 mol %), and L-Ala-O-tBu (72.6 mg, 0.500 mmol) were mixed in acetonitrile (MeCN), and heated at 80° C. and agitated for 24 hours. Thereafter, Fmoc-L-Ala-CO—Cl (165 mg, 0.500 mmol) and TBAF (1 mol/L in THF) (500 μL, 2 equivalents) were added to the mixture in the test tube, and the mixture was agitated at room temperature overnight. After the reaction, the mixture was diluted with chloroform (4.50 mL), and the product isolated by silica gel column chromatography, whereby the title compound was obtained as colorless solid with a yield of 61% (88.5 mg).

*Example II(11): Synthesis of Tetrapeptide Fmoc-Val-Ala-Ala-Ala-O-t-Bu Using Fused Ring Dipeptide Compound —Si(Ph)$_2$-Ala-Ala-

[Chem. 72]

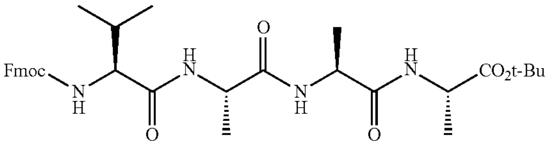

According to General Synthesis Procedure II(2), fused ring dipeptide compound —Si(Me,Ph)-L-Ala-L-Ala-(85.0 mg, 0.250 mmol), TMS-OTf) (1 mol/L in THF) (67.8 μL, 1.5 equivalents), hexane solution of MABR (12.5 μL, 10 mol %), and L-Ala-O-tBu (72.6 mg, 0.500 mmol) were mixed in acetonitrile (MeCN), and heated at 80° C. and agitated for 24 hours. Thereafter, Fmoc-L-Val-CO—Cl (179 mg, 0.500 mmol) and TBAF (1 mol/L in THF) (500 μL, 2 equivalents) were added to the test tube, and the mixture was agitated at room temperature overnight. After the reaction, the mixture was diluted with chloroform (4.50 mL), and the product isolated by silica gel column chromatography, whereby the title compound was obtained as colorless solid with a yield of 53% (80.6 mg).

*Example II(12): Synthesis of Tetrapeptide Fmoc-Met-Ala-Ala-Ala-O-t-Bu Using Fused Ring Dipeptide Compound —Si(Ph)$_2$-Ala-Ala-

[Chem. 74]

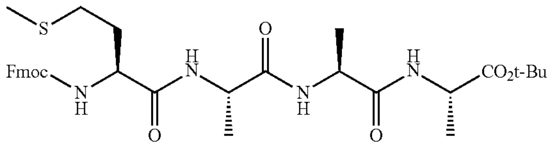

According to General Synthesis Procedure II(2), fused ring dipeptide compound —Si(Me,Ph)-L-Ala-L-Ala-(85.0 mg, 0.250 mmol), TMS-OTf) (1 mol/L in THF) (67.8 μL, 1.5 equivalents), hexane solution of MABR (12.5 μL, 10 mol %), and L-Ala-O-tBu (72.6 mg, 0.500 mmol) were mixed in acetonitrile (MeCN), and heated at 80° C. and agitated for 24 hours. Thereafter, Fmoc-L-Met-CO—Cl (195 mg, 0.500 mmol) and TBAF (1 mol/L in THF) (500 μL, 2 equivalents) were added to the test tube, and the mixture was agitated at room temperature overnight. After the reaction, the mixture was diluted with chloroform (4.50 mL), and the product isolated by silica gel column chromatography, whereby the title compound was obtained as colorless solid with a yield of 62% (99.2 mg).

*Example II(13): Synthesis of Tetrapeptide Cbz-Lys(Boc)-Ala-Ala-Ala-O-t-Bu Using Fused Ring Dipeptide Compound —Si(Ph)$_2$-Ala-Ala-

[Chem. 75]

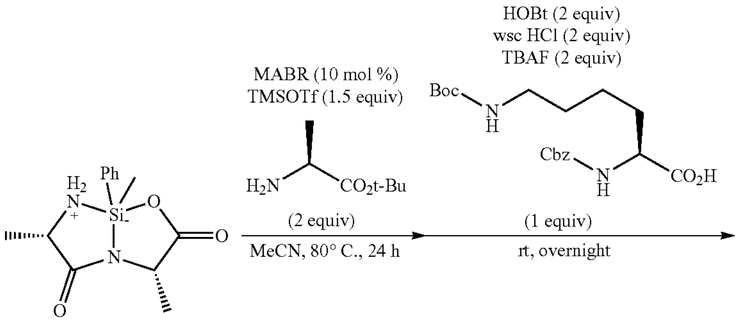

-continued

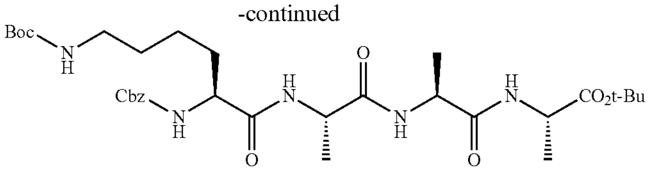

A test tube with a volume of 20 mL was charged with a stirrer bar, fused ring dipeptide compound —Si(Me,Ph)-L-Ala-L-Ala- (85.0 mg, 0.250 mmol), TMS-OTf) (1 mol/L in THF) (67.8 μL, 1.5 equivalents), hexane solution of MABR (12.5 μL, 10 mol %), and L-Ala-O-tBu (72.6 mg, 0.500 mmol) were mixed in acetonitrile (MeCN), and heated at 80° C. and agitated for 24 hours. Thereafter, Cbz-Lys(Boc)-OH (190 mg, 0.500 mmol), wscHCl (95.9 mg·0.500 mmol), HOBt (67.6 mg, 0.500 mmol), and TBAF (1 mol/L in THF) (500 μL, 0.500 mmol) were added to the test tube, and the mixture was agitated at room temperature overnight. After the reaction, the mixture was diluted with chloroform (4.50 mL), and the product isolated by silica gel column chromatography, whereby the title compound was obtained as colorless solid with a yield of 59% (95.8 mg).

*Example II(14): Synthesis of Hexapeptide Cbz-Ala-Met-Ala-Ser(t-Bu)-Ala-Ala-O-t-Bu Using Fused Ring Dipeptide Compounds —Si(Ph)$_2$-Met-Ala- and —Si(Ph)$_2$-Ser(t-Bu)-Ala- A two-pronged eggplant flask with a volume of 30 mL was charged with a stirrer bar, fused ring dipeptide compound —Si(Ph)$_2$-L-Met-L-Ala-(100 mg, 0.250 mmol), TBAF (1 mol/L in THF) (375 μL, 1.5 equivalents), wscHCl (95.9 mg, 2 equivalents), HOBt (67.6 mg, 2 equivalents) and Cbz-ALANINE (61.4 mg, 0.275 mmol), as well as DCM, and agitated at room temperature overnight. To the resulting solution, fused ring dipeptide compound —Si(Ph)$_2$-L-Ser(t-Bu)-L-Ala- (113 mg, 1.1 equivalents), TBAF (1 mol/L in THF) (375 μL, 1.5 equivalents), wscHCl (95.9 mg·2 equivalents), HOBt (67.6 mg, 2 equivalents) and DCM (1.00 mL) were added, and the mixture was agitated under nitrogen atmosphere at room temperature. After 24 hours, alanine tert-butyl ester (145 mg, 4 equivalents), wscHCl (95.9 mg·2 equivalents), HOBt (67.6 mg, 2 equivalents), triethyl amine (53 μL, 1.5 equivalents) and DCM (1 mL) were added to the flask, and agitated at room temperature for 24 hours. After the reaction, the mixture was diluted with chloroform (4.50 mL), and the product was isolated by silica gel column

[Chem. 76]

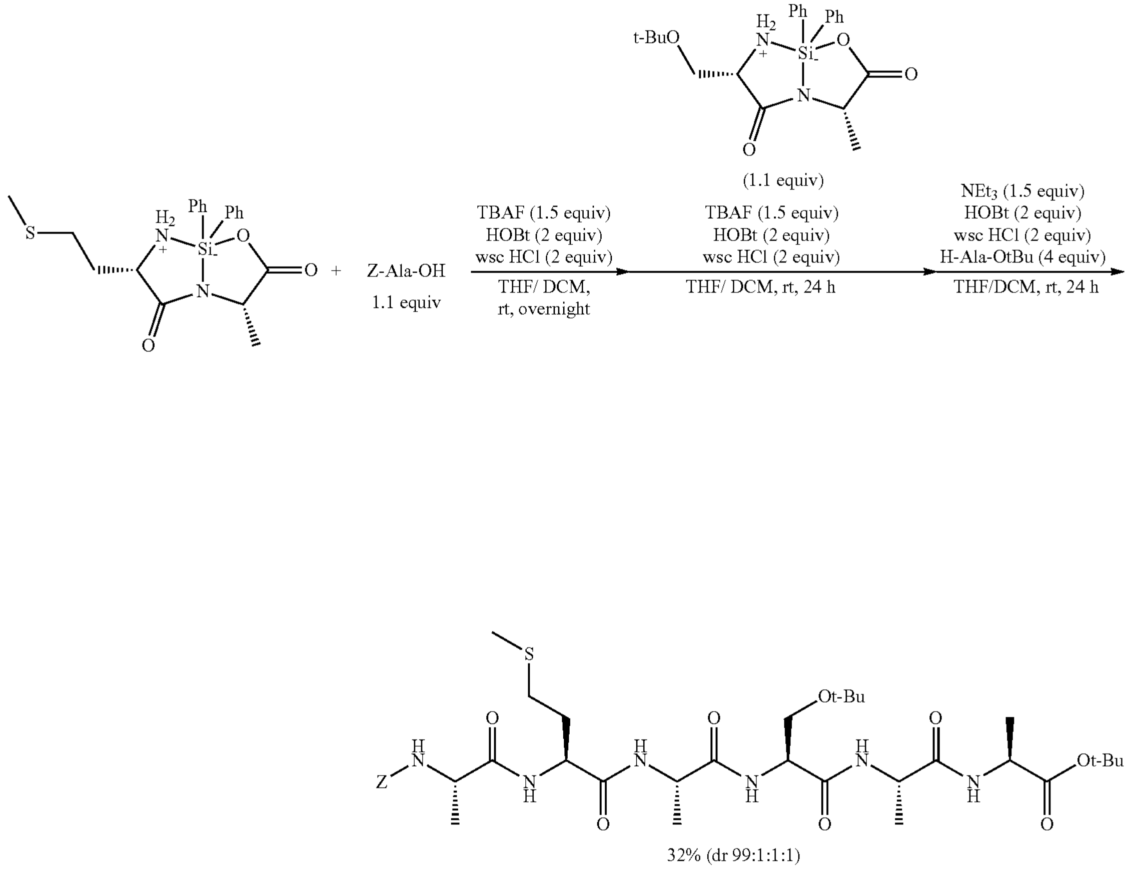

chromatography with methanol/chloroform (1/10), whereby the target hexapeptide was obtained with a yield of 32% (50.5 mg).

The invention claimed is:

1. A silane-containing fused ring dipeptide compound represented by formula (A)

(A)

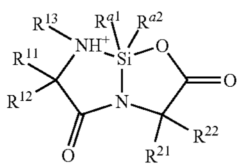

wherein, in formula (A), $R^{11}$, $R^{12}$, $R^{13}$, $R^{21}$, and $R^{22}$ represent, independently of each other, a hydrogen atom, halogen atom, hydroxyl group, carboxyl group, nitro group, cyano group, or thiol group, or a monovalent aliphatic hydrocarbon group, aromatic hydrocarbon group, or heterocyclic group that may have one or more substituents, and $R^{a1}$ and $R^{a2}$ represent, independently of each other, a monovalent aliphatic hydrocarbon group or aromatic hydrocarbon group that may have one or more substituents.

2. A method for producing a silane-containing fused ring dipeptide compound according to claim 1, comprising:

(i) causing a reaction between a first silane compound represented by formula (S1) and a second silane compound represented by formula (S2) in the presence of an amino acid represented by formula (R1); and (ii) adding an amino acid ester represented by formula (R2) to the reactant from step (i) to cause a further reaction, thereby preparing the a silane-containing fused ring dipeptide compound represented by formula (A);

(S1)

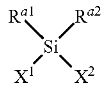

wherein, in formula (S1), $R^{a1}$ and $R^{a2}$ each represents the same definition as in formula (A), and $X^1$ and $X^2$ represent, independently of each other, a halogen atom;

(S2)

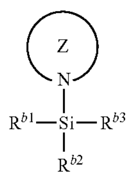

wherein, in formula (S2), $R^{b1}$, $R^{b2}$, and $R^{b3}$ represent, independently of each other, a hydrogen atom or halogen atom, or a monovalent aliphatic hydrocarbon group or aromatic hydrocarbon group that may have one or more substituents, and Z represents a 5- to 10-membered heterocyclic group that contain at least one nitrogen atom as a ring-constituting atom and that may have one or more substituents;

(R1)

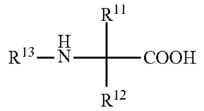

wherein, in formula (R1), $R^{11}$, $R^{12}$, and $R^{13}$ represent, independently of each other, the same definition as in formula (A);

(R2)

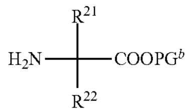

wherein, in formula (R2), $R^{21}$ and $R^{22}$, independently of each other, each represent the same definition as in formula (A), and $PG^b$ represents a protecting group for a carboxyl group.

3. The method according to claim 2, wherein the reaction system in step (i) also contains a base and/or wherein the reaction system in step (ii) also contains a Lewis acid catalyst.

4. A method for producing a polypeptide compound using a silane-containing fused ring dipeptide compound according to claim 1, comprising:

causing a reaction between a silane-containing fused ring dipeptide compound represented by formula (A), a protected amino acid or protected peptide compound represented by formula (R3), and an amino acid ester or peptide ester compound represented by formula (R4) to thereby produce a polypeptide compound represented by formula (P1);

(R3)

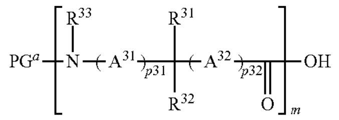

wherein, in formula (R3), $PG^a$ represents a protecting group for an amino group, $R^{31}$ and $R^{32}$ represent, independently of each other, a hydrogen atom, halogen atom, hydroxyl group, carboxyl group, nitro group, cyano group, or thiol group, or an amino group, monovalent aliphatic hydrocarbon group, monovalent aromatic hydrocarbon group, or monovalent heterocyclic group that may have one or more substituents, $R^{33}$ represents a hydrogen atom, carboxyl group, hydroxyl group, or a monovalent aliphatic hydrocarbon group, aromatic hydrocarbon group, or heterocyclic group that may have one or more substituents and that may be bound to the nitrogen atom via a linking group, or $R^{31}$ and $R^{33}$ may be bound to each other to form, together with the carbon atom to which $R^{31}$ binds and the nitrogen atom to which $R^{33}$ binds, a hetero ring that may have one or more substituents, $A^{31}$ and $A^{32}$ represent, independently of each other, a divalent aliphatic hydrocarbon group containing 1 to 3 carbon atoms that may have one or more substituents, p31 and p32 represent, independently of each other, 0 or 1, m represents an integer of equal to or greater than 1 corresponding to the number of the structure units parenthesized with [ ], provided that when m is equal to or greater than 2, then the two or more structure units in [ ] may be either identical to each other or different from each other;

(R4)

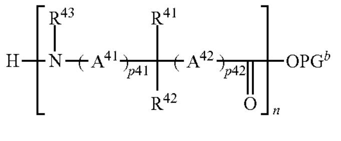

wherein, in formula (R4), $PG^b$ represents a protecting group for a carboxyl group, $R^{41}$ and $R^{42}$ represent, independently of each other, a hydrogen atom, halogen atom, hydroxyl group, carboxyl group, nitro group, cyano group, or thiol group, or an amino group, monovalent aliphatic hydrocarbon group, monovalent aromatic hydrocarbon group, or monovalent heterocyclic group that may have one or more substituents, $R^{43}$ represents a hydrogen atom, carboxyl group, hydroxyl group, or a monovalent aliphatic hydrocarbon group, aromatic hydrocarbon group, or heterocyclic group that may have one or more substituents and that may be bound to the nitrogen atom via a linking group, or $R^{41}$ and $R^{43}$ may be bound to each other to form, together with the carbon atom to which $R^{41}$ binds and the nitrogen atom to which $R^{43}$ binds, a hetero ring that may have one or more substituents, $A^{41}$ and $A^{42}$ represent, independently of each other, a divalent aliphatic hydrocarbon group containing 1 to 3 carbon atoms that may have one or more substituents, p41 and p42 represent, independently of each other, 0 or 1, n represents an integer of equal to or greater than 1 corresponding to the number of the structure units parenthesized with [ ], provided that when n is equal to or greater than 2, then the two or more structure units in [ ] may be either identical to each other or different from each other;

$PG^a$, $R^{31}$, $R^{32}$, $R^{33}$, $A^{31}$, $A^{32}$, p31, p32, and m each represent the same definition as in formula (R3), and $PG^b$, $R^{41}$, $R^{42}$, $R^{43}$, $A^{41}$, $A^{42}$, p41, p42, and n each represent the same definition as in formula (R4).

5. The method according to claim 4, comprising the steps of:

(i) causing a reaction between the silane-containing fused ring dipeptide compound represented by formula (A) and the protected amino acid or protected peptide compound represented by formula (R3); and (ii) causing a further reaction between the reactant from step (i) and the amino acid ester or peptide ester compound represented by formula (R4) to thereby prepare the polypeptide compound of formula (P1).

6. The method according to claim 4, comprising the steps of:

(i) causing a reaction between the silane-containing fused ring dipeptide compound represented by formula (A) and the amino acid ester or peptide ester compound represented by formula (R4); and (ii) causing a further reaction between the reactant from step (i) and the protected amino acid or protected peptide represented by formula (R3) to thereby prepare the polypeptide compound of formula (P1).

7. The method according to claim 5, wherein the reaction system in step (i) and/or (ii) contains a base and/or a condensing agent.

8. The method according to claim 4, further comprising the step of deprotecting the amino-protecting group $PG^a$ and/or the carboxyl-protecting group $PG^b$ in the polypeptide compound of formula (P1).

9. A method of producing a polypeptide compound using a silane-containing fused ring dipeptide compound according to claim 1, comprising:

causing reactions among a silane-containing fused ring dipeptide compound represented by formula (A1), a silane-containing fused ring dipeptide compound represented by formula (A2), a protected amino acid or protected peptide compound represented by formula (R3), and an amino acid ester or peptide ester compound represented by formula (R4) to thereby prepare a polypeptide compound represented by formula (P2);

(A1)

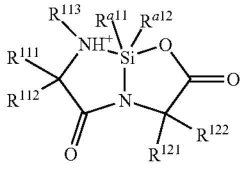

(P1)

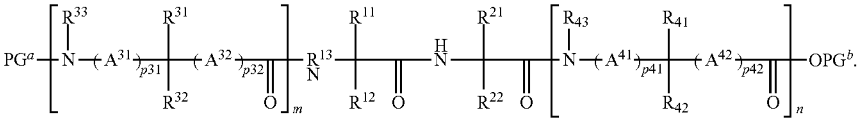

wherein, in formula (P1), $R^{11}$, $R^{12}$, $R^{13}$, $R^{21}$, and $R^{22}$ each represent the same definition as in formula (A), wherein, in formula (A1), $R^{111}$, $R^{112}$, $R^{113}$, $R^{121}$, and $R^{122}$ represent, independently of each other, a hydrogen atom, halogen atom, hydroxyl group, carboxyl group, nitro group, cyano group, or thiol group, or a monovalent aliphatic hydrocarbon group, aromatic hydrocarbon group, or heterocyclic group that may have one or more substituents, and $R^{a11}$ and $R^{a12}$ represent, independently of each other, a linear or cyclic aliphatic hydrocarbon group that may have one or more substituents;

(A2)

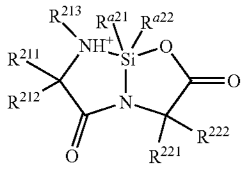

wherein, in formula (A2), $R^{211}$, $R^{212}$, $R^{213}$, $R^{221}$, and $R^{222}$ represent, independently of each other, a hydrogen atom, halogen atom, hydroxyl group, carboxyl group, nitro group, cyano group, or thiol group, or a monovalent aliphatic hydrocarbon group, aromatic hydrocarbon group, or heterocyclic group that may have one or more substituents, and $R^{a21}$ and $R^{a22}$ represent, independently of each other, a linear or cyclic aliphatic hydrocarbon group that may have one or more substituents;

(R3)

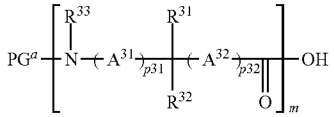

wherein, in formula (R3), $PG^a$ represents a protecting group for an amino group, $R^{31}$ and $R^{32}$ represent, independently of each other, a hydrogen atom, halogen atom, hydroxyl group, carboxyl group, nitro group, cyano group, or thiol group, or an amino group, monovalent aliphatic hydrocarbon group, monovalent aromatic hydrocarbon group, or monovalent heterocyclic group that may have one or more substituents, or $R^{31}$ and $R^{32}$ may be bound to each other to form, together with the carbon atom to which $R^{31}$ binds and the nitrogen atom to which $R^{32}$ binds, a hetero ring that may have one or more substituents, $A^{31}$ and $A^{32}$ represent, independently of each other, a divalent aliphatic hydrocarbon group containing 1 to 3 carbon atoms that may have one or more substituents, p31 and p32 represent, independently of each other, 0 or 1, and m represents an integer of equal to or greater than 1 and corresponds to the number of the structure units parenthesized with [ ], provided that when m is equal to or greater than 2, then the two or more structure units in [ ] may be either identical to each other or different from each other;

(R4)

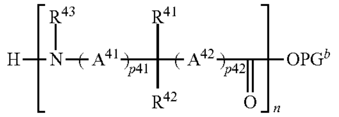

wherein, in formula (R4), $PG^b$ represents a protecting group for a carboxyl group, $R^{41}$ and $R^{42}$ represent, independently of each other, a hydrogen atom, halogen atom, hydroxyl group, carboxyl group, nitro group, cyano group, or thiol group, or an amino group, monovalent aliphatic hydrocarbon group, monovalent aromatic hydrocarbon group, or monovalent heterocyclic group that may have one or more substituents, or $R^{41}$ and $R^{42}$ may be bound to each other to form, together with the carbon atom to which $R^{41}$ binds and the nitrogen atom to which $R^{42}$ binds, a hetero ring that may have one or more substituents, $R^{43}$ represents a hydrogen atom, carboxyl group, hydroxyl group, or a monovalent aliphatic hydrocarbon group, aromatic hydrocarbon group, or heterocyclic group that may have one or more substituents and that may be bound to the nitrogen atom via a linking group, $A^{41}$ and $A^{42}$ represent, independently of each other, a divalent aliphatic hydrocarbon group containing 1 to 3 carbon atoms that may have one or more substituents, p41 and p42 represent, independently of each other, 0 or 1, and n represents an integer of equal to or greater than 1 corresponding to the number of the structure units parenthesized with [ ], provided that when n is equal to or greater than 2, then the two or more structure units in [ ] may be either identical to each other or different from each other;

(P2)

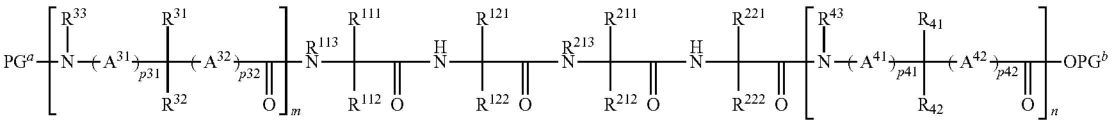

$R^{33}$ represents a hydrogen atom, carboxyl group, hydroxyl group, or a monovalent aliphatic hydrocarbon group, aromatic hydrocarbon group, or heterocyclic group that may have one or more substituents and that may be bound to the nitrogen atom via a linking group, wherein, in formula (P2), $R^{111}$, $R^{112}$, $R^{113}$, $R^{121}$, and $R^{122}$ each represents the same definition as in formula (A1), $R^{211}$, $R^{212}$, $R^{213}$, $R^{221}$, and $R^{222}$ each the formula (A2) represents the same definition as in the formula (A1), $PG^a$, $R^{31}$, $R^{32}$, $R^{33}$, $A^{31}$, $A^{32}$, p31, p32, and m each represent the same definition as in formula (R3), and $PG^b$, $R^{41}$, $R^{42}$, $R^{43}$, $A^{41}$, $A^{42}$, p41, p42, and n each represent the same definition as in formula (R4).

10. The method according to claim 9, comprising the steps of:

(i) causing a reaction between the silane-containing fused ring dipeptide compound represented by formula (A1) compound and the protected amino acid or protected peptide compound represented by formula (R3);

(ii) causing a further reaction between the reactant from step (i) and the silane-containing fused ring dipeptide compound represented by formula (A2); and (iii) causing a further reaction between the reactant from step (ii) and the amino acid ester or peptide ester compound represented by formula (R4) to thereby prepare the polypeptide compound of formula (P1).

11. The method according to claim 9, comprising the steps of:

(i) causing a reaction between the silane-containing fused ring dipeptide compound represented by formula (A2) and the amino acid ester or peptide ester compound represented by formula (R4);

(ii) causing a further reaction between the reactant from step (i) and the silane-containing fused ring dipeptide compound represented by formula (A1); and (iii) causing a further reaction between the reactant from step (ii) and the protected amino acid or protected peptide compound represented by formula (R3) to thereby prepare the polypeptide compound of formula (P1).

12. The method according to claim 10, wherein the reaction system in step (i) and/or (ii) and/or (iii) contains a base and/or a condensing agent.

13. The method according to claim 9, further comprising the step of deprotecting the amino-protecting group $PG^a$ and/or the carboxyl-protecting group $PG^b$ in the polypeptide compound of formula (P2).

14. The method according to claim 6, wherein the reaction system in step (i) and/or (ii) contains a base and/or a condensing agent.

15. The method according to claim 11, wherein the reaction system in step (i) and/or (ii) and/or (iii) contains a base and/or a condensing agent.

* * * * *